US009683025B2

(12) United States Patent
Zhang et al.

(10) Patent No.: US 9,683,025 B2
(45) Date of Patent: Jun. 20, 2017

(54) METHODS AND COMPOSITIONS FOR TREATING CANCER AND INFLAMMATORY DISEASES

(71) Applicant: The Regents of the University of Colorado, A Body Corporate, Denver, CO (US)

(72) Inventors: Qinghong Zhang, Englewood, CO (US); Rui Zhao, Englewood, CO (US); Xiao-Jing Wang, Greenwood Village, CO (US); Melanie Blevins, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 14/775,643

(22) PCT Filed: Mar. 13, 2014

(86) PCT No.: PCT/US2014/026874
§ 371 (c)(1),
(2) Date: Sep. 11, 2015

(87) PCT Pub. No.: WO2014/160508
PCT Pub. Date: Oct. 2, 2014

(65) Prior Publication Data
US 2016/0159872 A1  Jun. 9, 2016

Related U.S. Application Data

(60) Provisional application No. 61/780,901, filed on Mar. 13, 2013, provisional application No. 61/780,889, filed on Mar. 13, 2013.

(51) Int. Cl.
*C07K 14/47* (2006.01)
*A61K 38/00* (2006.01)

(52) U.S. Cl.
CPC .......... *C07K 14/4703* (2013.01); *A61K 38/00* (2013.01); *C07K 2319/10* (2013.01)

(58) Field of Classification Search
None
See application file for complete search history.

(56) References Cited

U.S. PATENT DOCUMENTS 6,716,964 B1 * 4/2004 Chinnadurai .......... C07K 14/47
435/69.1

FOREIGN PATENT DOCUMENTS

WO  WO 98/17806  *  4/1998
WO  2011103471 A1  8/2011

OTHER PUBLICATIONS

Schaeper et al. "Interaction between a Cellular Protein That Binds to the C-terminal Region of Adenovirus E1A (CtBP) and a Novel Cellular Protein Is Disrupted by E1A through a Conserved PLDLS Motif," J. Biol. Chem. (1998) vol. 273, No. 15, pp. 8549-8552.*
Schaeper et al. "Molecular cloning and characterization of a cellular phosphoprotein that interacts with a conserved C-terminal domain of adenovirus EIA involved in negative modulation of oncogenic transformation," Proc. Natl. Acad. Sci. USA (1995) vol. 92, pp. 10467-10471.*
Akhurst et al. "Targeting the TGFβ signalling pathway in disease," Nature Reviews Drug Discovery (2012) vol. 11, pp. 790-811.*
Wojcik et al. "Peptide-based inhibitors of protein—protein interactions" Bioorganic & Medicinal Chemistry Letters 26 (2016) 707-713.*
NIAMS "Understanding Autoimmune Diseases" downloaded from http://www.niams.nih.gov/health_info/Autoimmune/understanding_autoimmune.pdf.*
Rakoff-Nahoum "Why Cancer and Inflammation?" Yale Journal of Biology and Medicine 79 (2006), pp. 123-130.*
Birts, et al., "Expression of CtBP Family Protein Isoforms in Breast Cancer and Their Role in Chemoresistance", Biology of the Cell, vol. 103, No. 1, 2011, pp. 1-19.
Chinnadurai, "CtBP, an Unconventional Transcriptional Corepressor in Development and Oncogenesis", Molecular Cell, vol. 9, No. 2, 2002, pp. 213-224.
Chinnadurai, "The Transcriptional Corepressor CtBP: A Foe of Multiple Tumor Suppressors", Cancer Research, vol. 69, No. 3, 2009, pp. 731-734.
Deng, et al., "Transcriptional Down-Regulation of Brca1 and E-Cadherin by CtBP1 in Breast Cancer", Molecular Carcinogenesis, vol. 51, No. 6, 2012, pp. 500-507.
Johansson, et al., "Impact of the Interaction Between Adenovirus E1A and CtBP on Host Cell Gene Expression", Virus Research, vol. 113, No. 1, 2005, pp. 51-63.
Kuppuswamy, et al., "Role of the PLDLS-Binding Cleft Region of CtBP1 in Recruitment of Core and Auxiliary Components of the Corepressor Complex", Molecular and Cellular Biology, vol. 28, No. 1, 2008, pp. 269-281.
Quinlan, et al., "Role of the C-terminal Binding Protein PXDLS Motif Binding Cleft in Protein Interactions and Transcriptional Repression", Molecular and Cellular Biology, vol. 26, No. 21, 2006, pp. 8202-8213.
Saijo, et al., "An ADIOL-ER-CtBP Transrepression Pathway Negatively Regulates Microglia-Mediated Inflammation", Cell, vol. 145, No. 4, 2011, pp. 584-595.

(Continued)

*Primary Examiner* — Christina Bradley
(74) *Attorney, Agent, or Firm* — Saul Ewing LLP; Kathryn Doyle; Domingos J. Silva

(57) ABSTRACT

The invention provides a peptide construct comprising a cell penetrating peptide and an inhibitory peptide that interferes with the interaction between E1A and CtBP. The invention also provides related pharmaceutical composition comprising such a peptide construct. Also provided is a conjugate comprising such a peptide construct and a carrier molecule. The invention also provides related pharmaceutical compositions. Also provided are related methods of inhibiting cell proliferation in an individual and methods of treating cancer in by such pharmaceutical compositions. The present application also provides methods of treating an inflammatory disease and inhibiting inflammation in an individual comprising administering to the individual an effective amount of a therapeutic agent comprising an inhibitory peptide that interferes with the interaction between E1A and CtBP.

6 Claims, 15 Drawing Sheets

(56) References Cited

OTHER PUBLICATIONS

Straza, et al., "Therapeutic Targeting of C-Terminal Binding Protein in Human Cancer", Cell Cycle, vol. 9, No. 18, 2010, pp. 3764-3774.
Vocero-Akbani, et al., "Transduction of full-length Tat fusion proteins directly into mammalian cells: analysis of T cell receptor activation-induced cell death", Methods Enzymol., vol. 322, 2000, pp. 508-521.
Wang, et al., "Role of Transcriptional Corepressor CtBP1 in Prostate Cancer Progression", Neoplasia, vol. 14, No. 10, 2012, pp. 905-914.
zHang, et al., "Acetylation of Adenovirus E1A Regulates Binding of the Transcriptional Corepressor CtBP", PNAS, vol. 97, No. 26, 2000, pp. 14323-14328.
Zhao, et al., "Incapacitating CtBP to Kill Cancer", Cell Cycle, vol. 9, No. 18, 2010, pp. 3645-3646.
International Search Report dated Jul. 11, 2014, for PCT International Application No. PCT/US2014/026874.
Supplementary European Search Report dated Jul. 21, 2016 for European Application No. 14772587.3.

* cited by examiner

Figure 9

CONTROL PROTEIN E1A 243R [HUMAN ADENOVIRUS C]

NCBI Reference Sequence: NP_040508.1

```
  1 mrhiichggv iteemaasll dqlieevlad nlpppshfep ptlhelydld vtapedpnee
 61 avsqifpesv mlavqegidl ftfppapgsp epphlsrqpe qpeqralgpv smpnlvpevi
121 dltcheagfp psddedeegp vsepepepep epeparptrr pklvpailrr ptspvsrecn
181 sstdscdsgp sntppeihpv vplcpikpva vrvggrrqav eciedlines gqpldlsckr
241 prp  (SEQ ID NO:136)
```

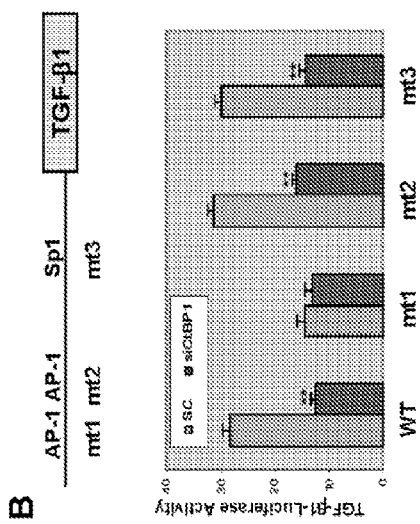
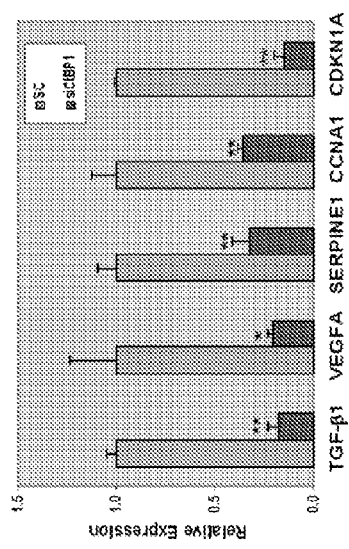
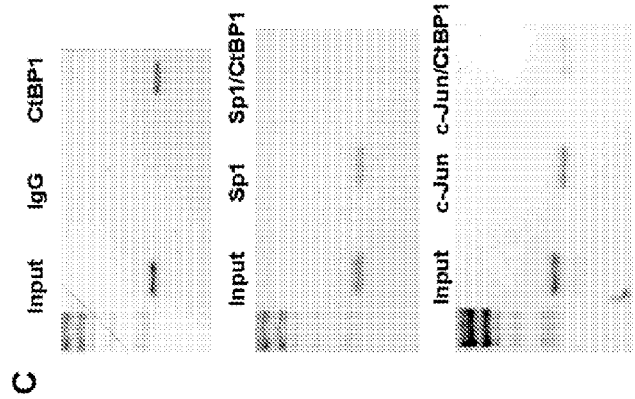
Figure 10

US 9,683,025 B2

METHODS AND COMPOSITIONS FOR TREATING CANCER AND INFLAMMATORY DISEASES

CROSS-REFERENCE TO RELATED APPLICATIONS

This application is a national phase filing under 35 U.S.C. §371 of International Application No. PCT/US2014/026874, having an international filing date of Mar. 13, 2014, which claims the priority benefit to U.S. Provisional Patent Application Ser. No. 61/780,889, filed Mar. 13, 2013, and U.S. Provisional Patent Application Ser. No. 61/780,901, filed Mar. 13, 2013, the entire content of each of which is incorporated herein by reference.

STATEMENT REGARDING FEDERALLY SPONSORED RESEARCH OR DEVELOPMENT

This invention was made with Government support awarded by the National Institutes of Health under grant (contract) number CA115468.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 277592000400SEQLIST.TXT, date recorded: Sep. 11, 2015, size: 65 KB).

FIELD OF THE INVENTION

The present invention relates to peptide constructs effective for inhibiting C-terminal Binding Protein (CtBP) activity, to pharmaceutical formulations of these peptide conjugates, to processes for their preparation, and to methods for their use in the treatment of proliferative diseases. The present invention also relates to therapeutic agents effective for inhibiting C-terminal Binding Protein (CtBP) activity, and methods for their use in the treatment of inflammatory diseases.

BACKGROUND OF THE INVENTION

Carboxyl-terminal binding protein (CtBP) was originally identified based on its ability to bind the carboxyl terminus of the E1A oncoprotein (Boyd et al., 1993; Schaeper et al., 1995). Subsequently, CtBP was found to be a transcriptional co-repressor interacting with DNA-binding transcription factors (Chinnadurai, 2002). Unlike most transcription factors with consensus DNA binding sites, CtBP indirectly binds DNA via various DNA binding partners at multiple DNA sequences, thus its transcriptional repression is context-specific. CtBP has remarkable amino acid homology with NADH-dependent dehydrogenases. Cancer cells typically have more NADH due to both hypoxia and pseudohypoxia (NADH production when oxygen concentration is not limited) (Sattler et al., 2007; Yeng et al., 2008; Zhang et al., 2007). The inventors have found NADH binds to CtBP with high affinity (Kd ~100 nM), which, without being tied to any particular theory, presumably causes a conformational change in CtBP that favors its binding to transcriptional factors (e.g., transcriptional repressors) (Zhang et al., 2002). The inventors have elucidated the major pathways controlled by CtBP in cancer cells and found CtBP directly represses epithelial genes and pro-apoptotic genes independently of p53, thus increasing cancer cell survival and migration.

CtBP interacts with E1A and many of its transcriptional factor partners through a conserved sequence motif, Pro-X-Asp-Leu-Ser (PXDLS) (Schaeper et al., 1995). A 14 mer E1A peptide (SEQ ID NO: 1) inhibited the CtBP/E1A interaction in vitro with an $IC_{50}$ of approximately 7 µM (Zhang et al. 2000).

All references cited herein, including patent applications and publications, are incorporated by reference in their entirety.

SUMMARY OF THE INVENTION

In one aspect, the present invention provides a peptide construct comprising a cell penetrating peptide and an inhibitory peptide that interferes with the interaction between E1A and CtBP. In certain embodiments, the peptide construct is a fusion peptide. In certain embodiments, the inhibitory peptide comprises $PX_1DLS$ (SEQ ID NO:2). In certain embodiments, the inhibitory peptide comprises $PX_1DLSX_2K$ (SEQ ID NO:6). In certain embodiments, the inhibitory peptide comprises SEQ ID NO:1. In certain embodiments, the binding affinity of the inhibitory peptide to CtBP is the same or higher than that of SEQ ID NO:1. In certain embodiments, the inhibitory peptide comprises the sequence EQTVPVDLSVARPR (SEQ ID NO:132). In certain embodiments, the inhibitory peptide comprises the sequence GGDGPLDLCCRKRP (SEQ ID NO:133). In certain embodiments, the inhibitory peptide comprises the sequence PTDEPLNLSLKRPR (SEQ ID NO:134). In certain embodiments, the inhibitory peptide comprises no more than about 25 amino acids. In certain embodiments, the inhibitory peptide comprises no more than about 15 amino acids. In certain embodiments, the peptide construct is modified for conjugation to a carrier molecule. In certain embodiments, the cell penetrating peptide is an amphipathic peptide or anionic peptide. In certain embodiments, the cell penetrating peptide is a cationic peptide. In certain embodiments, the cell penetrating peptide is selected from the group consisting of Tat, pAntp, Arg9, p1s1, and Pep1. In certain embodiments, the cell penetrating peptide is directly fused to the inhibitory peptide. In certain embodiments, the cell penetrating peptide is fused to the inhibitory peptide via a peptide linker. In certain embodiments, the cell penetrating peptide is fused to the N-terminus of the inhibitory peptide.

In a related aspect, the invention also provides a pharmaceutical composition comprising a peptide described herein. The invention also provides a conjugate comprising the peptide construct described herein and a carrier molecule. In certain embodiments, the carrier molecule is PEG.

The invention also provides a pharmaceutical composition comprising a conjugate described above.

In a related aspect, the invention provides a method of inhibiting cell proliferation in an individual comprising administering to the individual an effective amount of a pharmaceutical composition described herein. The invention also provides a method of treating cancer in an individual comprising administering to the individual an effective amount of a pharmaceutical composition described herein. In certain embodiments, the cancer is cancer having a p53 mutation. In certain embodiments, the pharmaceutical composition is administered intravenously, intratumorally, subcutaneously, orally, and topically.

The present invention in some embodiments provides a method of treating an inflammatory disease in an individual, comprising administering to the individual an effective amount of a therapeutic agent comprising an inhibitory peptide that interferes with the interaction between E1A and CtBP. The therapeutic agent may or may not further comprise a cell penetrating peptide such as any of the cell penetrating peptides described herein.

The present invention in some embodiments provides a method of inhibiting inflammation in an individual having an inflammatory disease, comprising administering to the individual an effective amount of a therapeutic agent comprising an inhibitory peptide that interferes with the interaction between E1A and CtBP. The therapeutic agent may or may not further comprise a cell penetrating peptide such as any of the cell penetrating peptides described herein.

In some embodiments according to (or as applied to) any of the embodiments above, the therapeutic agent is a peptide construct comprising a cell penetrating peptide and the inhibitory peptide.

In some embodiments according to (or as applied to) any of the embodiments above, the peptide construct is a fusion peptide.

In some embodiments according to (or as applied to) any of the embodiments above, the cell penetrating peptide is an amphipathic peptide or anionic peptide.

In some embodiments according to (or as applied to) any of the embodiments above, the cell penetrating peptide is a cationic peptide.

In some embodiments according to (or as applied to) any of the embodiments above, the cell penetrating peptide is selected from the group consisting of Tat, pAntp, Arg9, p1s1, and Pep1.

In some embodiments according to (or as applied to) any of the embodiments above, the cell penetrating peptide is directly fused to the inhibitory peptide.

In some embodiments according to (or as applied to) any of the embodiments above, the cell penetrating peptide is fused to the inhibitory peptide via a peptide linker.

In some embodiments according to (or as applied to) any of the embodiments above, the cell penetrating peptide is fused to the N-terminus of the inhibitory peptide.

In some embodiments according to (or as applied to) any of the embodiments above, the cell penetrating peptide is fused to the C-terminus of the inhibitory peptide.

In some embodiments according to (or as applied to) any of the embodiments above, the therapeutic agent comprises an inhibitory peptide not linked to a cell penetration peptide.

In some embodiments according to (or as applied to) any of the embodiments above, the inhibitory peptide comprises $PX_1DLS$ (SEQ ID NO:2), wherein $X_1$ is any amino acid.

In some embodiments according to (or as applied to) any of the embodiments above, the inhibitory peptide comprise $P X_1DLSX_2K$ (SEQ ID NO:6), wherein $X_1$ and $X_2$ are any amino acids.

In some embodiments according to (or as applied to) any of the embodiments above, the inhibitory peptide comprises EPGQPLDLSCKRPR (SEQ ID NO:1).

In some embodiments according to (or as applied to) any of the embodiments above, the inhibitory peptide comprises EQTVPVDLSVARPR (SEQ ID NO:132).

In some embodiments according to (or as applied to) any of the embodiments above, the inhibitory peptide comprises GGDGPLDLCCRKRP (SEQ ID NO:133).

In some embodiments according to (or as applied to) any of the embodiments above, the inhibitory peptide comprises PTDEPLNLSLKRPR (SEQ ID NO:134).

In some embodiments according to (or as applied to) any of the embodiments above, the binding affinity of the inhibitory peptide to CtBP is the same or higher than that of EPGQPLDLSCKRPR (SEQ ID NO:1).

In some embodiments according to (or as applied to) any of the embodiments above, the inhibitory peptide comprises no more than about 25 amino acids.

In some embodiments according to (or as applied to) any of the embodiments above, the inhibitory peptide comprises no more than about 15 amino acids.

In some embodiments according to (or as applied to) any of the embodiments above, the therapeutic agent is administered intravenously, intratumorally, subcutaneously, orally, and topically.

In some embodiments according to (or as applied to) any of the embodiments above, the inflammatory diseases is selected from the group consisting of psoriasis, mucositis, chronic wound, and trauma.

In some embodiments, the therapeutic agent has one or more biological activities in an individual selected from the group consisting of: reducing cancer cell proliferation, reducing EMT (epithelial-mesenchymal transition), increasing cancer cell apoptosis, reducing or eliminating TGF-β signaling, reducing or eliminating NF-κB signaling, reducing radiation-induced DNA damage, reducing inflammation, reducing angiogenesis, promoting healing in oral mucositis, promoting wound healing, and treating autoimmune disease when administered to an individual.

In some embodiments, a method provided herein for treating or preventing an inflammatory condition in an individual comprises administering to the individual a therapeutically effective amount of the pharmaceutical composition described herein. In some embodiments, the inflammatory condition may be one or more of a chronic wound, skin inflammation, psoriasis, or an autoimmune disease. In some embodiments, the composition may reduce inflammation through inhibition of TGF-β signaling and/or NF-κB signaling.

In some embodiments, a method provided herein for preventing or treating a disease or disorder in an individual comprises administering to the individual an effective amount of therapeutic agent described herein or a composition thereof. In some embodiments of the method described herein, the therapeutic agent increases cancer cell apoptosis, reduces cancer cell proliferation, reduces EMT, reduces or eliminates TGF-α signaling, reduces or eliminates NF-κB signaling, reduces radiation-induced DNA damage, reduces inflammation, and/or reduces angiogenesis in the individual. In some embodiments, the disease or disorder may include one or more of psoriasis, a chronic wound, an acute wound, or mucositis. In some embodiments, the chronic wound may include one or more of diabetic ulcers, pressure ulcers, venous ulcers, or oral ulcers. In some embodiments, the acute wound may include one or more of trauma-induced wounds, surgical wounds, or scarring. In some embodiments, the mucositis may include one or more of radiation-induced mucositis, chemotherapy-induced mucositis, oral mucositis, or gut mucositis.

BRIEF DESCRIPTION OF THE FIGURES

FIG. 1A-C) CtBP expression in hyperplasic and frankly malignant human head and neck squamous cell carcinoma is depicted in A-C. The dotted line indicates the epithelial/stromal junction; the scale bar is 20 μm. FIG. 1D-G) CtBP expression is shown in human poorly differentiated colon adenocarcinoma (D), moderately differentiated lung adenocarcinoma (E), ductal invasive breast carcinoma (F), and renal cell carcinoma (G).

FIG. 2A) Western blot analysis of CtBP in H1299 cells containing a tet-inducible siRNA-CtBP with or without Doxylcycline treatment for 3 days. FIG. 2B) Graph showing tumor growth of xenografts of H1299 cells containing a tet-inducible siRNA-CtBP with or without Doxylcycline treatment in SCID mice at the 8-week time point. FIG. 2C) Representative image of the tumor xenografts from the untreated (−) and Doxylcycline treated (+) mice.

FIG. 7A) H&E staining showing Pep1-E1A decreases the IMQ-induced epithelial hyperplasia and inflammatory cell infiltration in the stroma (bottom) compared to the PBS-treated skin (top). The scale bar is 100 μm. FIG. 7B) Immunostaining showing decreased BrdU (left panels) and CD45 (right panels) after Pep1-E1A treatment. Sections were counterstained with K14.

FIG. 9 shows the control protein E1A 243R [Human adenovirus C] NCBI Reference Sequence: NP_040508.1. Amino acid sequence is SEQ ID NO:136.

FIG. 10A-C shows transcriptional activation of TGF-β1 by CtBP1. FIG. 10A) Graph showing that CtBP1 knockdown downregulates the TGF-β1 signaling pathway. FIG. 10B) Graph showing that CtBP1 regulates TGF-β1 via the distal AP-1 site at the TGF-β1 promoter. FIG. 10C) ChIP analysis showing that CtBP1 is recruited by c-Jun to the promoter of TGF-β1. Top panel shows the single ChIP assay using control IgG (IgG) or an anti-CtBP1 (CtBP1) antibody. Middle panel shows the single ChIP using an anti-Sp1 antibody and the sequential ChIP using an anti-CtBP1 antibody following the first ChIP with an anti-Sp1 antibody (Sp1/CtBP1). Bottom panel shows the single ChIP using an anti-c-Jun antibody (c-Jun) and the sequential ChIP using an anti-CtBP1 antibody following the first ChIP with an anti-c-Jun antibody (c-Jun/CtBP1).

FIG. 11A) Generation of K5.CtBP1 mice. FIG. 11B) Graph showing elevated TGF-β1 mRNA in K5.CtBP1 transgenic mice skin. FIG. 11C) Immunofluorescence imaging of leukocyte subtypes (counterstained with K14 (red) antibody). FIG. 11D) Immunofluorescence imaging of the endothelial marker CD31 (counterstained with a red K14 antibody). The scale bar is 80 μm. FIG. 11E) Immunofluorescence imaging of CD31 (green) and ALK1 (red). K5.CtBP1 skin contained more ALK1-positive vessels (yellow) compared to WT tissue.

FIG. 12A) Immunohistochemistry pictures of CtBP1 in psoriasis lesions (bottom) and normal human skin (top). Sections were counterstained with hematoxylin. FIG. 12B) Western blot analysis showing the expression of CtBP1 in skins of nontransgenic mice (WT), K5.CtBP1 expressors (Tg), and wounded nontransgenic skin (Wound). Tubulin was used as a loading control. FIG. 12C) Immunofluorescence imaging of CtBP1 in wound (bottom) and non-wounded normal mouse skin (top). Sections were counterstained with K14.

FIG. 15A) Purification of synthesized Tat-E1A and FIG. 15B) Reduction of erythema, thickening and scaling (cumulative score) with Pep1-E1A (squares) or Tat-E1A (triangles) treatment in a psoriasis model. PBS (diamonds) indicates treatment with phosphate buffered saline.

DETAILED DESCRIPTION

Figure 1:
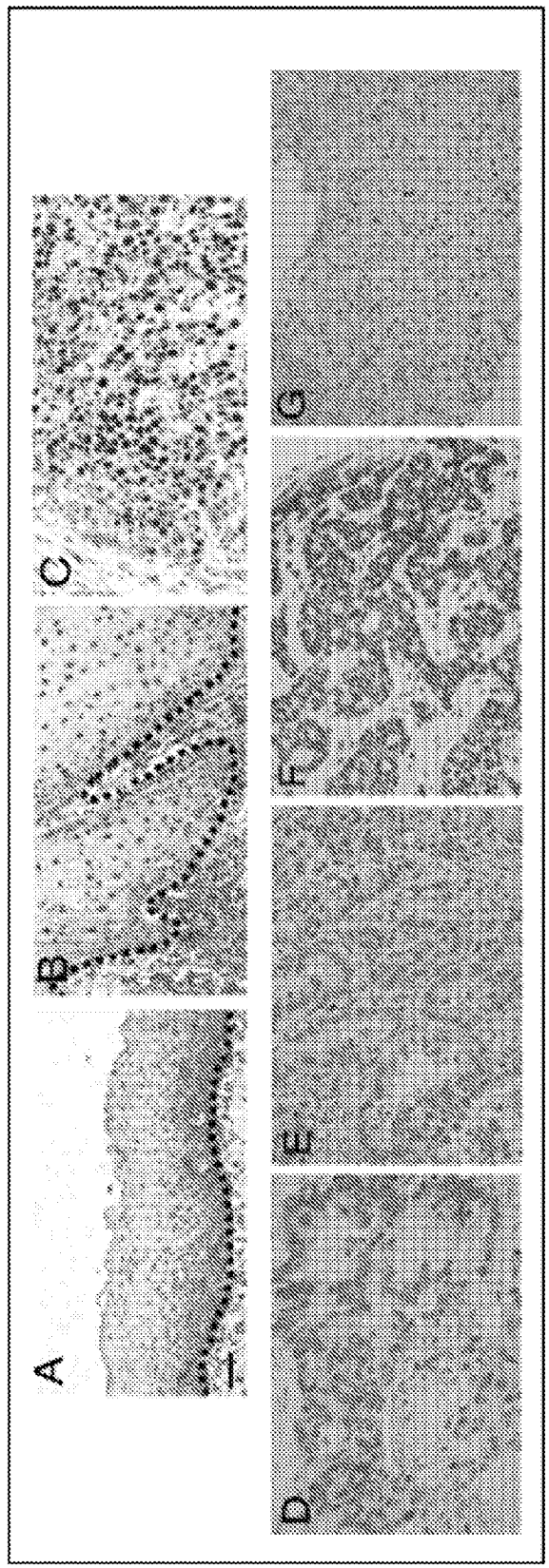
FIG. 1A-G shows CtBP expression in human carcinomas.

The present application in some aspects provides peptide constructs and uses thereof for treating cancer. The peptide constructs comprise a cell penetrating peptide and an inhibitory peptide that interferes with the interaction between E1A and CtBP. It was shown that peptide constructs comprising a cell-penetrating peptide and an inhibitory peptide that disrupts CtBP interactions with E1A, i.e., a fusion peptide containing a cell penetration peptide (CPP) and a 14-amino acid peptide derived from E1A (Tat-E1A), can enter the cytoplasm and nuclei of target cancer cells, e.g., A375 melanoma cells or H1299 non-small cell lung cancer cells, and reduce their viability. It was also shown that peptide constructs comprising a cell-penetrating peptide and an inhibitory peptide that disrupts CtBP interactions with E1A, i.e., a fusion peptide containing a cell penetration peptide (CPP) and a 14-amino acid peptide derived from E1A (Pep1-E1A or Tat-E1A), reduces over-proliferation and inflammation in a mouse model of psoriasis. These peptide constructs are therefore particularly useful for inhibiting CtBP function in vivo and for treating diseases such as cancer.

Thus, the present application in one aspect provides peptide constructs comprising a cell penetrating peptide and an inhibitory peptide that interferes with the interaction between E1A and CtBP.

In another aspect, there is provided a method of treating cancer in an individual, comprising administering to the individual an effective amount of a peptide construct comprising a cell penetrating peptide and an inhibitory peptide that interferes with the interaction between E1A and CtBP.

The present application also provides therapeutic agents and uses thereof for treating inflammatory diseases. The therapeutic agents comprises an inhibitory peptide that disrupts CtBP interaction with E1A, and in some embodiments comprises a peptide constructs comprising a cell penetrating peptide and an inhibitory peptide that interferes with the interaction between E1A and CtBP.

This aspect of the present invention is based on the unexpected finding of transactivation of TGF-β1 by CtBP and its functional impact on inflammation. Specifically, it was found that CtBP is a transcriptional activator of TGF-β1, and CtBP1 overexpression in transgenic mice causes inflammation and increases angiogenesis associated with enhanced TGF-β1 signaling. It was further found that CtBP1 is overexpressed in human psoriasis lesions and in the inflammatory phase of wound healing, in addition to oral mucositis. Furthermore, using a peptide construct comprising a cell-penetrating peptide and an inhibitory peptide that disrupts CtBP interactions with E1A, i.e., a fusion peptide containing a cell penetration peptide (CPP) and a 14-amino acid peptide derived from E1A (Pep1-E1A or Tat-E1A), it was further demonstrated that targeting CtBP reduces overproliferation and inflammation in a mouse model of psoriasis. Thus, targeting CtBP1 (either with or without the use of a cell penetrating peptide) can be useful as a therapeutic strategy against inflammatory diseases.

Thus, the present application in one aspect provides a method of treating an inflammatory disease comprising administering to the individual a therapeutic agent comprising an inhibitory peptide that interferes with the interaction between E1A and CtBP. In some embodiments, the therapeutic agent is a peptide construct comprising a cell penetrating peptide and an inhibitory peptide that interferes with the interaction between E1A and CtBP.

In another aspect, there is provided a method of inhibiting inflammation in an individual having an inflammatory disease, comprising administering to the individual a therapeutic agent comprising an inhibitory peptide that interferes with the interaction between E1A and CtBP. In some embodiments, the therapeutic agent is a peptide construct comprising a cell penetrating peptide and an inhibitory peptide that interferes with the interaction between E1A and CtBP. In some embodiments, the therapeutic agent does not comprise a cell penetrating peptide.

Also provided are kits, unit doses, pharmaceutical compositions, and articles of manufacture comprising the peptide constructs that are suitable for uses in methods described herein.

Peptide Constructs and Conjugates

The present application in one aspect provides peptide constructs comprising a cell penetrating peptide and an inhibitory peptide that interferes with the interaction between E1A and CtBP. In some embodiments, the cell penetrating peptide is linked to the N-terminus of the inhibitory peptide via its C-terminus. In some embodiments, the cell penetrating peptide is linked to the C-terminus of the inhibitory peptide via its N-terminus.

The therapeutic agents useful for methods described herein in some embodiments comprises peptide constructs comprising a cell penetrating peptide and an inhibitory peptide that interferes with the interaction between E1A and CtBP. In some embodiments, the cell penetrating peptide is linked to the N-terminus of the inhibitory peptide via its C-terminus. In some embodiments, the cell penetrating peptide is linked to the C-terminus of the inhibitory peptide via its N-terminus.

In some embodiments, the cell penetrating peptide and inhibitory peptide are directly linked. In some embodiments, the cell penetrating peptide and the inhibitory peptide are linked via a linker. The linker that links the cell penetrating peptide and the inhibitory peptide can be of different nature, so long as it does not interfere with the functions and/or binding properties of the cell penetrating peptide and the inhibitory peptide. In some embodiments, the cell penetrating peptide and the inhibitory peptide are linked via a peptide linker. In some embodiments, the peptide linker is no more than about 20 amino acids (for example no more than about any of 15, 10, 9, 8, 7, 6, 5, 4, 3, 2, or 1 amino acid long). In some embodiments, the peptide linker is no more than about 10 amino acids (for example, the peptide linker can be about any of 10, 9, 8, 7, 6, 5, 4, 3, 2, or 1 amino acid long). In some embodiments, the peptide linker is no more than about 5 amino acids (for example, about 2 amino acids). In some embodiments, the linker is a two-amino acid peptide linked having the sequence of LE (SEQ ID NO: 106).

In some embodiments, the cell penetrating peptide and the inhibitory peptide are linked via a non-peptide linker, e.g. a chemical coupling agent such gluteraldehyde. In some embodiments, the chemical coupling agent is a carbodiimide, e.g. EDC. In some embodiments, the chemical cross-linking agent is m-maleimidobenzoyl-n-hydroxysuccinimide ester or MBS. In some embodiments, heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[pazidosalicylamido]butylamine), and an amino group and a guanidinium group that is present in the side chain of arginine (e.g., p-azidophenyl glyoxal monohydrate.

In some embodiments, the cell penetration peptide is between about 5 to about 30 amino acids long, including for example about 10 to about 25 amino acids long. In some embodiments, the cell penetration peptide is no more than about 30 amino acids long (for example, no more than about any of 21, 20, 19, 18, 17, 16, 15, 14, 13, 12, 11, 10, 9, 8, 7, 6, 5, or 4 amino acids long).

In some embodiments, the inhibitory peptide is about 5 to about 70 amino acids long, including for example about 5 to about 10, about 10 to about 20, about 20 to about 30, about 30 to about 40, about 40 to about 50, about 50 to about 60, or about 60 to about 70 amino acids long. In some embodiments, the inhibitory peptide is about 10 to about 20 amino acids long, such as about 14 amino acids long. In some embodiments, the inhibitory peptide is no more than about 30, no more than about 25, or more than about 20, no more than about 15, or no more than about 10 amino acids long.

In some embodiments, the peptide construct is a fusion peptide. In some embodiments, the fusion peptide is about 10 to about 100 amino acids long, including for example about 10 to about 20, about 20 to about 30, about 30 to about 40, about 40 to about 50, about 50 to about 60, about 60 to about 70 amino acids long, about 70 to about 80, about 80 to about 90, or about 90 to about 100 amino acids long. In some embodiments, the inhibitory peptide is no more than about 50, no more than about 40, no more than about 30, no more than about 25, no more than about 20 amino acids, or no more than about 15 amino acids long.

In some embodiments, there is provided a peptide construct comprising a cell penetrating peptide and an inhibitory peptide that interferes with the interaction between E1A and CtBP, wherein the inhibitory peptide has an IC50 that is no more than the IC50 of the EPGQPLDLSCKRPR (SEQ ID NO:1). In some embodiments, there is provided a peptide construct comprising a cell penetrating peptide and an inhibitory peptide that interferes with the interaction between E1A and CtBP, wherein the inhibitory peptide competitively inhibits the binding of EPGQPLDLSCKRPR (SEQ ID NO:1) to CtBP. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, there is provided a peptide construct comprising a cell penetrating peptide and an inhibitory peptide that interferes with the interaction between E1A and CtBP, wherein the inhibitory peptide comprises the sequence $PX_1X_2X_3X_4$ (SEQ ID NO:129), wherein $X_1$ is L, V, I, M, Q, or E, $X_2$ is D or N, $X_3$ is L or I, and $X_4$ is S, C, T, V or A. In some embodiments, there is provided a peptide construct comprising a cell penetrating peptide and an inhibitory peptide that interferes with the interaction between E1A and CtBP, wherein the inhibitory peptide comprises the sequence PLDLS (SEQ ID NO:3). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $PX_1DLS$ (SEQ ID NO:2), wherein $X_1$ is any amino acid. In some embodiments, there is provided a peptide construct comprising a cell penetrating peptide and an inhibitory peptide that interferes with the interaction between E1A and CtBP, wherein the inhibitory peptide comprises the sequence PLDLS (SEQ ID NO:3). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $N_4PX_1X_2X_3X_4$ (SEQ ID NO:138), wherein $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, there is provided a peptide construct comprising a cell penetrating peptide and an inhibitory peptide that interferes with the interaction between E1A and CtBP, wherein the inhibitory peptide comprises the sequence $N_4PX_1X_2X_3X_4$ (SEQ ID NO:139), wherein $N_4$ is Q, V, E or G, and wherein $X_1$ is L, V, I, M, Q or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $N_3N_4PX_1X_2X_3X_4$ (SEQ ID NO:140), wherein $N_3$ is G, T, D, E or N, and $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, there is provided a peptide construct comprising a cell penetrating peptide and an inhibitory peptide that interferes with the interaction between E1A and CtBP, wherein the inhibitory peptide comprises the sequence $N_3N_4PX_1X_2X_3X_4$ (SEQ ID NO:141), wherein $N_3$ is G, T, D, E or N, and $N_4$ is Q, V, E or G, and wherein $X_1$ is L, V, I, M, Q or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $N_2N_3N_4PX_1X_2X_3X_4$ (SEQ ID NO:142), wherein $N_2$ is P, Q, G, S, T, V or M, $N_3$ is G, T, D, E or N, and $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, there is provided a peptide construct comprising a cell penetrating peptide and an inhibitory peptide that interferes with the interaction between E1A and CtBP, wherein the inhibitory peptide comprises the sequence $N_2N_3N_4PX_1X_2X_3X_4$ (SEQ ID NO:143), wherein $N_2$ is P, Q, G, S, T, V or M, $N_3$ is G, T, D, E or N, and $N_4$ is Q, V, E or G, and wherein $X_1$ is L, V, I, M, Q or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $N_1N_2N_3N_4PX_1X_2X_3X_4$ (SEQ ID NO:144), wherein $N_1$ is E, G, P, A or V, $N_2$ is P, Q, G, S, T, V or M, $N_3$ is G, T, D, E or N, and $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, there is provided a peptide construct comprising a cell penetrating peptide and an inhibitory peptide that interferes with the interaction between E1A and CtBP, wherein the inhibitory peptide comprises the sequence $N_1N_2N_3N_4PX_1X_2X_3X_4$ (SEQ ID NO:145), wherein $N_1$ is E, G, P, A or V, $N_2$ is P, Q, G, S, T, V or M, $N_3$ is G, T, D, E or N, $N_4$ is Q, V, E or G, and wherein $X_1$ is L, V, I, M, Q or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $PX_1X_2X_3X_4C_1$ (SEQ ID NO:146), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T. In some embodiments, there is provided a peptide construct comprising a cell penetrating peptide and an inhibitory peptide that interferes with the interaction between E1A and CtBP, wherein the inhibitory peptide comprises the sequence $PX_1X_2X_3X_4C_1$ (SEQ ID NO:147), wherein $X_1$ is L, V, I, M, Q or E, $X_2$ is D or N, $X_3$ is L or I, and $X_4$ is S, C, T, V or A, and wherein $C_1$ is C, M, L, K, V or T. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $PX_1X_2X_3X_4C_1C_2$ (SEQ ID NO:148), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T and $C_2$ is K, A or R. In some embodiments, there is provided a peptide construct comprising a cell penetrating peptide and an inhibitory peptide that interferes with the interaction between E1A and CtBP, wherein the inhibitory peptide comprises the sequence $PX_1X_2X_3X_4C_1C_2$ (SEQ ID NO:149), wherein $X_1$ is L, V, I, M, Q or E, $X_2$ is D or N, $X_3$ is L or I, and $X_4$ is S, C, T, V or A, and wherein $C_1$ is C, M, L, K, V or T and $C_2$ is K, A or R. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $PX_1X_2X_3X_4C_1C_2C_3$ (SEQ ID NO:150), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, and $C_3$ is R, T, H, P, K or C. In some embodiments, there is provided a peptide construct comprising a cell penetrating peptide and an inhibitory peptide that interferes with the interaction between E1A and CtBP, wherein the inhibitory peptide comprises the sequence $PX_1X_2X_3X_4C_1C_2C_3$ (SEQ ID NO:151), wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, and $C_3$ is R, T, H, P, K or C. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $PX_1X_2X_3X_4C_1C_2C_3C_4$ (SEQ ID NO:152), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, and $C_4$ is P, S, G, R or L. In some embodiments, there is provided a peptide construct comprising a cell penetrating peptide and an inhibitory peptide that interferes with the interaction between E1A and CtBP, wherein the inhibitory peptide comprises the sequence $PX_1X_2X_3X_4C_1C_2C_3C_4$ (SEQ ID NO:153), wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, and $C_4$ is P, S, G, R or L. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $PX_1X_2X_3X_4C_1C_2C_3C_4C_5$ (SEQ ID NO:154), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, there is provided a peptide construct comprising a cell penetrating peptide and an inhibitory peptide that interferes with the interaction between E1A and CtBP, wherein the inhibitory peptide comprises the sequence $PX_1X_2X_3X_4C_1C_2C_3C_4C_5$ (SEQ ID NO:155), wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $N_4PX_1X_2X_3X_4C_1$ (SEQ ID NO:156), wherein $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T. In some embodiments, there is provided a peptide construct comprising a cell penetrating peptide and an inhibitory peptide that interferes with the interaction between E1A and CtBP, wherein the inhibitory peptide comprises the sequence $N_4PX_1X_2X_3X_4C_1$ (SEQ ID NO:157), wherein $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $N_3N_4PX_1X_2X_3X_4C_1C_2$ (SEQ ID NO:158), wherein $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, and $C_2$ is K, A or R. In some embodiments, there is provided a peptide construct comprising a cell penetrating peptide and an inhibitory peptide that interferes with the interaction between E1A and CtBP, wherein the inhibitory peptide comprises the sequence $N_3N_4PX_1X_2X_3X_4C_1C_2$ (SEQ ID NO:159), wherein $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, and $C_2$ is K, A or R. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $N_2N_3N_4PX_1X_2X_3X_4C_1C_2C_3$ (SEQ ID NO:160), wherein $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, and $C_3$ is R, T, H, P, K or C. In some embodiments, there is provided a peptide construct comprising a cell penetrating peptide and an inhibitory peptide that interferes with the interaction between E1A and CtBP, wherein the inhibitory peptide comprises the sequence $N_2N_3N_4PX_1X_2X_3X_4C_1C_2C_3$ (SEQ ID NO:161), wherein $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, and $C_3$ is R, T, H, P, K or C. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $N_1N_2N_3N_4PX_1X_2X_3X_4C_1C_2C_3C_4$ (SEQ ID NO:162), wherein $N_1$ is E, G, P, A or V, $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, and $C_4$ is P, S, G, R or L. In some embodiments, there is provided a peptide construct comprising a cell penetrating peptide and an inhibitory peptide that interferes with the interaction between E1A and CtBP, wherein the inhibitory peptide comprises the sequence $N_1N_2N_3N_4PX_1X_2X_3X_4C_1C_2C_3C_4$ (SEQ ID NO:163), wherein $N_1$ is E, G, P, A or V, $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, and $C_4$ is P, S, G, R or L. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:128), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:128), wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, there is provided a peptide construct comprising a cell penetrating peptide and an inhibitory peptide that interferes with the interaction between E1A and CtBP, wherein the inhibitory peptide comprises $PX_1X_2X_3X_4$ (SEQ ID NO:129), wherein X1 is L, V, I, M, Q or E, $X_2$ is D or N, $X_3$ is L or I, and $X_4$ is 5, C, T, V or A, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:129), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:129), wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, there is provided a peptide construct comprising a cell penetrating peptide and an inhibitory peptide that interferes with the interaction between E1A and CtBP, wherein the inhibitory peptide comprises the sequence $N_1N_2N_3N_4PX_1X_2X_3X_4C_1C_2C_3C_4C_5$ (SEQ ID NO:130), wherein $N_1$ is E, G, P, A or V, $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, there is provided a peptide construct comprising a cell penetrating peptide and an inhibitory peptide that interferes with the interaction between E1A and CtBP, wherein the inhibitory peptide comprises the sequence $N_1N_2N_3N_4PX_1X_2X_3X_4C_1C_2C_3C_4C_5$ (SEQ ID NO:131), wherein $N_1$ is E, G, P, A or V, $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is 5, C, T, V or A, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, there is provided a peptide construct comprising a cell penetrating peptide and an inhibitory peptide that interferes with the interaction between E1A and CtBP, wherein the inhibitory peptide comprises the sequence EQTVPVDLSVARPR (SEQ ID NO:132). In some embodiments, there is provided a peptide construct comprising a cell penetrating peptide and an inhibitory peptide that interferes with the interaction between E1A and CtBP, wherein the inhibitory peptide comprises the sequence GGDGPLDLCCRKRP (SEQ ID NO:133). In some embodiments, there is provided a peptide construct comprising a cell penetrating peptide and an inhibitory peptide that interferes with the interaction between E1A and CtBP, wherein the inhibitory peptide comprises the sequence PTDEPLNLSLKRPR (SEQ ID NO:134). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $PX_1DLSX_2X_3$ (SEQ ID NO:4), wherein $X_1$ and $X_2$ are any amino acids, and $X_3$ is an amino acid having a bulky side chain. In some embodiments, there is provided a peptide construct comprising a cell penetrating peptide and an inhibitory peptide that interferes with the interaction between E1A and CtBP, wherein the inhibitory peptide comprises the sequence $PX_1DLSX_2X_3$ (SEQ ID NO:5), wherein $X_1$ and $X_2$ are any amino acids, and $X_3$ is R or K. In some embodiments, there is provided a peptide construct comprising a cell penetrating peptide and an inhibitory peptide that interferes with the interaction between E1A and CtBP, wherein the inhibitory peptide comprises the sequence $PX_1DLSX_2K$ (SEQ ID NO:6), wherein $X_1$ and $X_2$ are any amino acids. In some embodiments, there is provided a peptide construct comprising a cell penetrating peptide and an inhibitory peptide that interferes with the interaction between E1A and CtBP, wherein the inhibitory peptide comprises the sequence $PX_1DLSX_2Q$ (SEQ ID NO:7), wherein $X_1$ and $X_2$ are any amino acids. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence $PLDLSX_1X_2$ (SEQ ID NO:8), wherein $X_1$ is any amino acids, and $X_2$ is an amino acid having a bulky side chain. In some embodiments, there is provided a peptide construct comprising a cell penetrating peptide and an inhibitory peptide that interferes with the interaction between E1A and CtBP, wherein the inhibitory peptide comprises the sequence $PLDLSX_1X_2$ (SEQ ID NO:9), wherein $X_1$ is any amino acids, and $X_2$ is R or K. In some embodiments, there is provided a peptide construct comprising a cell penetrating peptide and an inhibitory peptide that interferes with the interaction between E1A and CtBP, wherein the inhibitory peptide comprises the sequence $PLDLSX_1K$ (SEQ ID NO:10), wherein $X_1$ is any amino acid. In some embodiments, there is provided a peptide construct comprising a cell penetrating peptide and an inhibitory peptide that interferes with the interaction between E1A and CtBP, wherein the inhibitory peptide comprises the sequence $PLDLSX_1Q$ (SEQ ID NO:11), wherein $X_1$ is any amino acid. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence PLDLSCK (SEQ ID NO:12). In some embodiments, there is provided a peptide construct comprising a cell penetrating peptide and an inhibitory peptide that interferes with the interaction between E1A and CtBP, wherein the inhibitory peptide comprises the sequence PLDLSCR (SEQ ID NO:13). In some embodiments, there is provided a peptide construct comprising a cell penetrating peptide and an inhibitory peptide that interferes with the interaction between E1A and CtBP, wherein the inhibitory peptide comprises the sequence PLDLSCQ (SEQ ID NO:14). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises the sequence PLDLSCKRPR (SEQ ID NO:15). In some embodiments, there is provided a peptide construct comprising a cell penetrating peptide and an inhibitory peptide that interferes with the interaction between E1A and CtBP, wherein the inhibitory peptide comprises the sequence PLDLSCRPR (SEQ ID NO:16). In some embodiments, there is provided a peptide construct comprising a cell penetrating peptide and an inhibitory peptide that interferes with the interaction between E1A and CtBP, wherein the inhibitory peptide comprises the sequence PLDLSCQRPR (SEQ ID NO:17). n some embodiments, there is provided a peptide construct comprising a cell penetrating peptide and an inhibitory peptide that interferes with the interaction between E1A and CtBP, wherein the inhibitory peptide comprises the sequence PLDLSCRRPR (SEQ ID NO:122). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the inhibitory peptide comprises (e.g., is) the sequence EPGQPLDLSCKRPR (SEQ ID NO:1). In some embodiments, there is provided a peptide construct comprising a cell penetrating peptide and an inhibitory peptide that interferes with the interaction between E1A and CtBP, wherein the inhibitory peptide comprises (e.g., is) the sequence EPGQPLDLSCRPRP (SEQ ID NO:18). In some embodiments, there is provided a peptide construct comprising a cell penetrating peptide and an inhibitory peptide that interferes with the interaction between E1A and CtBP, wherein the inhibitory peptide comprises (e.g., is) the sequence EPGQPLDLSCQRPR (SEQ ID NO:19). In some embodiments, there is provided a peptide construct comprising a cell penetrating peptide and an inhibitory peptide that interferes with the interaction between E1A and CtBP, wherein the inhibitory peptide comprises (e.g., is) the sequence EPGQPLDLSCRRPR (SEQ ID NO:123). In some embodiments, there is provided a peptide construct comprising a cell penetrating peptide and an inhibitory peptide that interferes with the interaction between E1A and CtBP, wherein the inhibitory peptide comprises (e.g., is) the sequence EQTVPVDLSVARPR (SEQ ID NO:132). In some embodiments, there is provided a peptide construct comprising a cell penetrating peptide and an inhibitory peptide that interferes with the interaction between E1A and CtBP, wherein the inhibitory peptide comprises (e.g., is) the sequence GGDGPLDLCCRKRP (SEQ ID NO:133). In some embodiments, there is provided a peptide construct comprising a cell penetrating peptide and an inhibitory peptide that interferes with the interaction between E1A and CtBP, wherein the inhibitory peptide comprises (e.g., is) the sequence PTDEPLNLSLKRPR (SEQ ID NO:134). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a peptide construct comprising a cell penetrating peptide and an inhibitory peptide that interferes with the interaction between E1A and CtBP, wherein the peptide construct comprises (e.g., is) SEQ ID NO:20. Table 1 provides the amino acid sequences for these and several peptide constructs referred to throughout the specification. In some embodiments, there is provided a peptide construct comprising a cell penetrating peptide and an inhibitory peptide that interferes with the interaction between E1A and CtBP, wherein the peptide construct comprises (e.g., is) SEQ ID NO:22. In some embodiments, there is provided a peptide construct comprising a cell penetrating peptide and an inhibitory peptide that interferes with the interaction between E1A and CtBP, wherein the peptide construct comprises (e.g., is) SEQ ID NO:26. In some embodiments, there is provided a peptide construct comprising a cell penetrating peptide and an inhibitory peptide that interferes with the interaction between E1A and CtBP, wherein the peptide construct comprises (e.g., is) SEQ ID NO:28.

TABLE 1

Peptide Constructs

| Peptide Name | SEQ ID NO: | Amino Acid Sequence |
|---|---|---|
| Tat-E1A | 20 | GRKKRRQRRRPPQLEEPGQ PLDLSCKRPR |
| Tat-E1A (LS-EL) | 21 | GRKKRRQRRRPPQLEEPGQ PLDELCKRPR |
| Tat-E1A (K239Q) | 22 | GRKKRRQRRRPPQLEEPGQ PLDLSCQRPR |
| Pep1-E1A | 23 | KETWWETWWTEWSQPKKKR KVLEEPGQPLDLSCKRPR |
| Pep1-E1A (LS-EL) | 24 | KETWWETWWTEWSQPKKKR KVLEEPGQPLDELCKRPR |
| Pep1-E1A (K239Q) | 25 | KETWWETWWTEWSQPKKKR KVLEEPGQPLDELCQRPR |
| Tat-E1A GSHM | 26 | GSHMGRKKRRQRRRPPQLE EPGQPLDLSCKRPR |
| Tat-E1A (LS-EL) GSHM | 27 | GSHMGRKKRRQRRRPPQLE EPGQPLDELCKRPR |
| Tat-E1A (K239Q) GSHM | 28 | GSHMGRKKRRQRRRPPQLE EPGQPLDLSCQRPR |
| Pep1-E1A GSHM | 29 | GSHMKETWWETWWTEWSQP KKKRKVLEEPGQPLDLSCK RPR |
| Pep1-E1A (LS-EL) GSHM | 30 | GSHMKETWWETWWTEWSQP KKKRKVLEEPGQPLDELCK RPR |

TABLE 1-continued

Peptide Constructs

| Peptide Name | SEQ ID NO: | Amino Acid Sequence |
|---|---|---|
| Pep1-E1A (K239Q) GSHM | 31 | GSHMKETWWETWWTEWSQP KKKRKVLEEPGQPLDELCQ RPR |
| Pep1-E1A (K239Q) v.1 | 124 | KETWWETWWTEWSQPKKKR KVLEEPGQPLDLSCQRPR |
| Pep1-E1A (K239Q) GSHM v.1 | 125 | GSHMKETWWETWWTEWSQP KKKRKVLEEPGQPLDLSCQ RPR |

In some embodiments, the peptide constructs described herein are modified for increased in vivo stability, bioavailability, and/or biological activity. Such modifications include, but are not limited to, amidation of the N or C-termini or acetylation of one or more of peptide residues, so long as such modification does not interfere with the functionalities of the peptide constructs (Cho et al., Science 261:1303-1305 (1993).

In some embodiments, the peptide constructs described herein are modified for the purpose of conjugating to a larger carrier molecule (such as PEG). For example, in some embodiments, the peptide constructs are modified for conjugation through the addition of one or more cysteine residues to the peptide construct for use in PEGylating the peptide construct. In some embodiments, the one or more cysteine residues are added to the N-terminus of the peptide construct. In some embodiments, the one or more cysteine residues are added to the C-terminus of the peptide construct. In some embodiments, the one or more cysteine residues are added to the N-terminus of the inhibitory peptide. In some embodiments, a 3xGly linker (i.e., Gly-Gly-Gly; SEQ ID NO:107) is added in addition to the cysteine residue. In some embodiments, the peptide construct further comprises a serine or threonine at the N-terminus of the cell penetrating peptide, for example, for use in placing a single PEG chain at a defined site on the cell penetrating peptide. In some embodiments, the serine or threonine is added at the C-terminus of the cell penetrating peptide. In some embodiments, the serine or threonine is added at the N-terminus of the inhibitory peptide. In some embodiments, the serine or threonine is added at the C-terminus of the inhibitory peptide. The present application thus encompasses any of the modified peptide constructs described herein.

In some embodiments, the peptide constructs described herein are modified for the purpose of conjugating to a larger carrier molecule (such as PEG). For example, in some embodiments, the peptide constructs are modified for conjugation through the addition of one or more cysteine residues to the peptide construct for use in PEGylating the peptide construct. In some embodiments, a 3XGly linker (i.e., Gly-Gly-Gly; SEQ ID NO:107) is added in addition to the cysteine. In some embodiments, the one or more cysteine residues are added to the N-terminus of the peptide construct. In some embodiments, the one or more cysteine residues are added to the C-terminus of the peptide construct. In some embodiments, the one or more cysteine residues are added to the N-terminus of the inhibitory peptide. In some embodiments, a 3xGly linker (i.e., Gly-Gly-Gly; SEQ ID NO:107) is added in addition to the cysteine residue. In some embodiments, the peptide construct further comprises a serine or threonine at the N-terminus of the cell penetrating peptide, for example, for use in placing a single PEG chain at a defined site on the cell penetrating peptide. In some embodiments, the serine or threonine is added at the C-terminus of the cell penetrating peptide. In some embodiments, the serine or threonine is added at the N-terminus of the inhibitory peptide. In some embodiments, the serine or threonine is added at the C-terminus of the inhibitory peptide. The present application thus encompasses any of the modified peptide constructs described herein.

The present application in some embodiments also provides conjugates comprising any of the peptide constructs described herein and a carrier molecule. Suitable carrier molecules include, but are not limited to: polyethylene glycols, lipids, carbohydrates, immunoglobulins, and albumin. In some embodiments, the carrier molecule is a polyethylene glycol or a derivative thereof. The peptide construct described herein can be PEGylated as described in, e.g., Lee et al. (1999) Bioconjug. Chem. 10(6): 973-8; Kinstler et al. (2002) Advanced Drug Deliveries Reviews 54:477-485; and Roberts et al. (2002) Advanced Drug Delivery Reviews 54:459-476. In some embodiments, the PEG carrier can improve the stability, or retention of, said peptide construct by at least 50 (e.g., at least 2, 5, 10, 15, 20, 25, 30, 40, or 50 or more) fold. In some embodiments, the carrier molecule is selected from the group consisting of PEG-malemimide, PEG-vinylsulfone, PEG-iodoacetamide, PEG orthopyridyl disulfide, and thiol-reactive PEG created to PEGylate free cysteine residues (Liu, 2011: http://www.pharmtech.com/pharmtech/Drug+Delivery/Peptide-PEGylation-The-Next-Generation/ArticleStandard/Article/detail/718859, accessed on Mar. 7, 2013.

In some embodiments, the modified peptide constructs described herein are PEGylated with branched PEGs, thus enabling a larger and purer PEG to be linked with only one reactive group; consequently, this bulkier branched PEG assists in repelling approaching macromolecules from a peptide's active site and protecting the peptide construct and/or conjugate from proteases. In some embodiments, the modified peptide constructs described herein are PEGylated in a number of different ways and tested for in vitro and in vivo activity to determine which method of PEGylation is most effective (e.g., by comparing the number of chains attached to the peptide construct, the molecular weight and structure of the chains, and the specific attachment site/s of the PEG).

Thus, in some embodiments, there is provided a conjugate comprising a peptide construct and a carrier molecule, wherein the peptide construct comprises a cell penetrating peptide and an inhibitory peptide that interferes with the interaction between E1A and CtBP. In some embodiments, the inhibitory peptide comprises the sequence $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $PX_1X_2X_3X_4$ (SEQ ID NO:129), wherein $X_1$ is L, V, I, M, Q, or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

Thus, in some embodiments, there is provided a conjugate comprising a peptide construct and a carrier molecule, wherein the peptide construct comprises a cell penetrating peptide and an inhibitory peptide that interferes with the interaction between E1A and CtBP. In some embodiments, the inhibitory peptide comprises the sequence PX$_1$DLS (SEQ ID NO:2), wherein X$_1$ is any amino acid. In some embodiments, the inhibitory peptide comprises the sequence PLDLS (SEQ ID NO:3). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

Thus, in some embodiments, the therapeutic agents useful for methods described herein comprise a conjugate comprising a peptide construct and a carrier molecule, wherein the peptide construct comprises a cell penetrating peptide and an inhibitory peptide that interferes with the interaction between E1A and CtBP. In some embodiments, the inhibitory peptide comprises the sequence PX$_1$DLS (SEQ ID NO:2), wherein X$_1$ is any amino acid. In some embodiments, the inhibitory peptide comprises the sequence PLDLS (SEQ ID NO:3). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence N$_4$PX$_1$X$_2$X$_3$X$_4$ (SEQ ID NO:138), wherein N$_4$ is Q, V, E or G, and wherein X$_1$ is a hydrophobic residue, X$_2$ is a residue that preserves hydrogen bonding with CtBP, X$_3$ is a hydrophobic residue, and X$_4$ is a residue that preserves hydrogen bonding with CtBP. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence N$_4$PX$_1$X$_2$X$_3$X$_4$ (SEQ ID NO:139), wherein N$_4$ is Q, V, E or G, and wherein X$_1$ is L, V, I, M, Q or E, X2 is D or N, X$_3$ is L or I, and X$_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence N$_3$N$_4$PX$_1$X$_2$X$_3$X$_4$ (SEQ ID NO:140), wherein N$_3$ is G, T, D, E or N, and N$_4$ is Q, V, E or G, and wherein X$_1$ is a hydrophobic residue, X$_2$ is a residue that preserves hydrogen bonding with CtBP, X$_3$ is a hydrophobic residue, and X$_4$ is a residue that preserves hydrogen bonding with CtBP. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence N$_3$N$_4$PX$_1$X$_2$X$_3$X$_4$ (SEQ ID NO:141), wherein N$_3$ is G, T, D, E or N, and N$_4$ is Q, V, E or G, and wherein X$_1$ is L, V, I, M, Q or E, X$_2$ is D or N, X$_3$ is L or I, and X$_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence N2N3N4PX1X2X3X4 (SEQ ID NO:142), wherein N2 is P, Q, G, S, T, V or M, N3 is G, T, D, E or N, and N4 is Q, V, E or G, and wherein X1 is a hydrophobic residue, X2 is a residue that preserves hydrogen bonding with CtBP, X3 is a hydrophobic residue, and X4 is a residue that preserves hydrogen bonding with CtBP. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence N2N3N4PX1X2X3X4

(SEQ ID NO:143), wherein N2 is P, Q, G, S, T, V or M, N3 is G, T, D, E or N, and N4 is Q, V, E or G, and wherein X1 is L, V, I, M, Q or E, X2 is D or N, X3 is L or I, and X4 is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $N_1N_2N_3N_4PX_1X_2X_3X_4$ (SEQ ID NO:144), wherein $N_1$ is E, G, P, A or V, $N_2$ is P, Q, G, S, T, V or M, $N_3$ is G, T, D, E or N, and $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $N_1N_2N_3N_4PX_1X_2X_3X_4$ (SEQ ID NO:145), wherein $N_1$ is E, G, P, A or V, $N_2$ is P, Q, G, S, T, V or M, $N_3$ is G, T, D, E or N, $N_4$ is Q, V, E or G, and wherein $X_1$ is L, V, I, M, Q or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $PX_1X_2X_3X_4C_1$ (SEQ ID NO:146), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $PX_1X_2X_3X_4C_1$ (SEQ ID NO:147), wherein $X_1$ is L, V, I, M, Q or E, $X_2$ is D or N, $X_3$ is L or I, and $X_4$ is S, C, T, V or A, and wherein $C_1$ is C, M, L, K, V or T. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $PX_1X_2X_3X_4C_1C_2$ (SEQ ID NO:148), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T and $C_2$ is K, A or R. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $PX_1X_2X_3X_4C_1C_2$ (SEQ ID NO:149), wherein $X_1$ is L, V, I, M, Q or E, $X_2$ is D or N, $X_3$ is L or I, and $X_4$ is S, C, T, V or A, and wherein $C_1$ is C, M, L, K, V or T and $C_2$ is K, A or R. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $PX_1X_2X_3X_4C_1C_2C_3$ (SEQ ID NO:150), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, and $C_3$ is R, T, H, P, K or C. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $PX_1X_2X_3X_4C_1C_2C_3$ (SEQ ID NO:151), wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, and $C_3$ is R, T, H, P, K or C. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $PX_1X_2X_3X_4C_1C_2C_3C_4$ (SEQ ID NO:152), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, and $C_4$ is P, S, G, R or L. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $PX_1X_2X_3X_4C_1C_2C_3C_4$ (SEQ ID NO:153), wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, and $C_4$ is P, S, G, R or L. In some embodiments, the cell penetrating peptide is an amphipathic peptide. In some embodiments, the cell penetrating peptide is a cationic peptide. In some embodiments, the cell penetration peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $PX_1X_2X_3X_4C_1C_2C_3C_4C_5$ (SEQ ID NO:154), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $PX_1X_2X_3X_4C_1C_2C_3C_4C_5$ (SEQ ID NO:155), wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $N_4PX_1X_2X_3X_4C_1$ (SEQ ID NO:156), wherein $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $N_4PX_1X_2X_3X_4C_1$ (SEQ ID NO:157), wherein $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $N_3N_4PX_1X_2X_3X_4C_1C_2$ (SEQ ID NO:158), wherein $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, and $C_2$ is K, A or R. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $N_3N_4PX_1X_2X_3X_4C_1C_2$ (SEQ ID NO:159), wherein $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, and $C_2$ is K, A or R. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $N_2N_3N_4PX_1X_2X_3X_4C_1C_2C_3$ (SEQ ID NO:160), wherein $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, and $C_3$ is R, T, H, P, K or C. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $N_2N_3N_4PX_1X_2X_3X_4C_1C_2C_3$ (SEQ ID NO:161), wherein $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, and $C_3$ is R, T, H, P, K or C. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $N_1N_2N_3N_4PX_1X_2X_3X_4C_1C_2C_3C_4$ (SEQ ID NO:162), wherein $N_1$ is E, G, P, A or V, $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, and $C_4$ is P, S, G, R or L. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $N_1N_2N_3N_4PX_1X_2X_3X_4C_1C_2C_3C_4$ (SEQ ID NO:163), wherein $N_1$ is E, G, P, A or V, $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, and $C_4$ is P, S, G, R or L. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:128), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:128), wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $PX_1X_2X_3X_4$ (SEQ ID NO:129), wherein $X_1$ is L, V, I, M, Q or E, $X_2$ is D or N, $X_3$ is L or I, and $X_4$ is 5, C, T, V or A, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:129), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:129), wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $N_1N_2N_3N_4PX_1X_2X_3X_4C_1C_2C_3C_4C_5$ (SEQ ID NO:130), wherein $N_1$ is E, G, P, A or V, $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $N_1N_2N_3N_4PX_1X_2X_3X_4C_1C_2C_3C_4C_5$ (SEQ ID NO:131), wherein $N_1$ is E, G, P, A or V, $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is 5, C, T, V or A, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence EQTVPVDLSVARPR (SEQ ID NO:132). In some embodiments, the inhibitory peptide comprises the sequence GGDGPLDLCCRKRP (SEQ ID NO:133). In some embodiments, the inhibitory peptide comprises the sequence PTDEPLNLSLKRPR (SEQ ID NO:134). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $PX_1DLSX_2X_3$ (SEQ ID NO:4), wherein $X_1$ and $X_2$ are any amino acids, and $X_3$ is an amino acid having a bulky side chain (such as R or K). In some embodiments, the inhibitory peptide comprises the sequence $PX_1DLSX_2K$ (SEQ ID NO:6), wherein $X_1$ and $X_2$ are any amino acids. In some embodiments, the inhibitory peptide comprises the sequence $PLDLSX_1K$ (SEQ ID NO:10), wherein $X_1$ is any amino acid. In some embodiments, the inhibitory peptide comprises the sequence PLDLSCK (SEQ ID NO:12). In some embodiments, the inhibitory peptide comprises the sequence PLDLSCKRPR (SEQ ID NO:15). In some embodiments, the inhibitory peptide comprises (e.g., is) the sequence EPGQPLDLSCKRPR (SEQ ID NO:1). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a conjugate comprising a peptide construct and a carrier molecule, wherein the peptide construct comprises a cell penetrating peptide and an inhibitory peptide that interferes with the interaction between E1A and CtBP, wherein the peptide construct comprises (e.g., is) SEQ ID NO:20. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the peptide construct comprises (e.g., is) SEQ ID NO:22. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the peptide construct comprises (e.g., is) SEQ ID NO:26. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the peptide construct comprises (e.g., is) SEQ ID NO:28.

Cell Penetration Peptides

The peptide constructs of the present application comprises cell penetrating peptides. Cell penetrating peptides, also called cell-permeable peptides, protein-transduction domains (PTD) or membrane-translocation sequences (MTS), are known to have the ability to translocate in vitro and/or in vivo mammalian cell membranes and enter into cells. CPPs are capable of directing a conjugated compound of interest to a desired cellular destination, e.g. into the cytoplasm or the nucleus. Accordingly, CPPs can direct or facilitate penetration of a compound of interest across a phospholipid, mitochondrial, endosomal or nuclear membrane. A CPP can also direct a compound of interest from outside the cell through the plasma membrane, and into the cytoplasm or to a desired location within the cell, e.g., the nucleus, the ribosome, the mitochondria, the endoplasmic reticulum, a lysosome, or a peroxisome. In addition, the CPP can direct a compound of interest across the blood-brain, trans-mucosal, hematoretinal, skin, gastrointestinal and/or pulmonary barriers.

CPPs are typically short peptides (for example about 10 to 30 amino acids in length). They can efficiently penetrate the cell membrane and enter almost all cell types together with its covalently conjugated molecular cargo. Sebbage, 2009, Cell Penetrating Pepetides and Their Therapeutic Applications. Bioscience Horizons, 2, 64-72.

In some embodiments, the CPP is a amphipathic peptide. In some embodiments, the CPP is a cationic peptide. For example, in some embodiments, at least about 30% (including for example at least about 40%, about 50%, about 60%, about 70%, about 80%, about 90%, or 100%) of amino acids in the CPP are positively charged. In some embodiments, the CPP comprises a nuclear localization signal.

In some embodiments, the CPP is derived from a naturally occurring protein, including for example HIV-1, Antennapedia protein (e.g., its homeodomain), VP22, Herpes Simplex Virus, Calcitonin, antimicrobial to toxin peptides. In some embodiments, the CPP is a chimeric peptide. For example, in some embodiments, the CPP is a chimeric peptide composed of a portion from galanin and a portion from the wasp venom peptide mastoparan. In some embodiments, the CPP is a non-naturally occurring peptide (for example a peptide that has been altered from a naturally occurring peptide). Heitz et al., British J. of Pharmacology 157 (2009) 195-2-6 provide additional examples of CPPs that may be suitable for the peptide constructs described herein.

In some embodiments, the CPP is selected from the group consisting of Tat, Pep1, Pep7, pAntp, MPG, DPV, Buforin II, Haptotactic peptides, Cβ, preCγ, CαE, hCT(9-32), HN-1, Influenza virus nucleoprotein, KALA, K-FGF, Ku70, MAP, MPM (IP/K-FGF), N50 (NLS of NF-κB P50), Penetratin, Poly Arginine, pISL, Prion mouse PrPcl-28, pVEC, SAP, SV-40 (NLS), SynB, Tat, Transportan, VP22, VT5, and functionally equivalent variants thereof. In some embodiments, the CPP is selected from the group consisting of Tat, Pep1, pAntp, Arge9, pIsL, and functionally equivalent variants thereof. In some embodiments, the CPP comprises (e.g., is) Tat. In some embodiments, the CPP comprises (e.g., is) Pep1. In some embodiments, the CPP comprises (e.g., is) pAntp. In some embodiments, the CPP is any one of the cell penetration peptides listed in Table 2 (SEQ ID Nos: 33-83). In some embodiments, the CPP is a functional variant of any one of the cell penetration peptides listed in Table 2 (SEQ ID Nos: 33-83).

TABLE 2

Exemplary Cell Penetrating Peptides

| SEQ ID NO: | Cell Penetrating Peptides | Amino acid sequences (N-terminus to C-terminus) |
|---|---|---|
| 32 | Buforin II | TRSSRAGLQFPVGRVHRLLRK |
| 33 | DPV3 | RKKRRRESRKKRRRES |
| 34 | DPV6 | GRPRESGKKRKRKRLKP |
| 35 | DPV7 | GKRKKKGKLGKKRDP |
| 36 | DPV7b | GKRKKKGKLGKKRPRSR |
| 37 | DPV3/10 | RKKRRRESRRARRSPRHL |
| 38 | DPV10/6 | SRRARRSPRESGKKRKRKR |
| 39 | DPV1047 | VKRGLKLRHVRPRVTRMDV |
| 40 | DPV1048 | VKRGLKLRHVRPRVTRDV |
| 41 | DPV10 | SRRARRSPRHLGSG |
| 42 | DPV15 | LRRERQSRLRRERQSR |
| 43 | DPV15b | GAYDLRRRERQSRLRRRERQSR |
| 44 | GALA | WEAALAEALAEALAEHLAEALAEALE ALAA |
| 45 | Haptotactic peptides | |
| 46 | Cβ | KGSWYSMRKMSMKIRPFFPQQ |
| 47 | preCγ | KTRYYSMKKTTMKIIPFNRL |
| 48 | CαE | RGADYSLRAVRMKIRPLVTQ |
| 49 | hCT(9-32) | LGTYTQDFNKFHTFPQTAIGVGAP |
| 50 | HN-1 | TSPLNIHNGQKL |
| 51 | Influenza virus nucleoprotein (NLS) | NSAAFEDLRVLS |
| 52 | KALA | WEAKLAKALAKALAKHLAKALAKALK ACEA |
| 53 | K-FGF | AAVALLPAVLLALLAP |
| 54 | Ku70 | VPMLKPMLKE |
| 55 | MAP | KLALKLALKALKAALKLA |
| 56 | MPG | GALFLGFLGAAGSTMGAWSQPKKKRK V |
| 57 | MPM (IP/K-FGF) | AAVALLPAVLLALLAP |
| 58 | N50 (NLS of NF-κB P50) | VQRKRQKLM |
| 59 | p-Antp | RQIKIWFQNRRMKWKK |
| 60 | Pep-1 | KETWWETWWTEWSQPKKKRKV |
| 61 | Pep-7 | SDLWEMMMVSLACQY |
| 62 | Penetratin | RQIKIWFQNRRMKWKK |
| 63 | Short Penetratin | RRMKWKK |
| 64 | Poly Arginine- $R_7$ | RRRRRRR |
| 65 | Poly Arginine- $R_9$ | RRRRRRRRR |
| 66 | pISL | RVIRVWFQNKRCKDKK |
| 67 | Prion mouse $PrPc_{1-28}$ | MANLGYWLLALFVTMWTDVGLCKKRP KP |
| 68 | pVEC | LLIILRRRIRKQAHAHSK |
| 69 | SAP | VRLPPPVRLPPPVRLPPP |
| 70 | SV-40 (NLS) | PKKKRKV |
| 71 | SynB1 | RGGRLSYSRRRFSTSTGR |
| 72 | SynB3 | RRLSYSRRRF |
| 73 | SynB4 | AWSFRVSYRGISYRRSR |
| 74 | $Tat_{47-60}$ | YGRKKRRQRRRPPQ |
| 75 | $Tat_{48-60}$ | GRKKRRQRRRPPQ |
| 76 | $Tat_{48-61}$ | GRKKRRQRRRPPQQ |
| 77 | $Tat_{47-57}$ | YGRKKRRQRRR |
| 78 | $Tat_{49-57}$ | RKKRRQRRR |
| 79 | Transportan | GWTLNSAGYLLGKINLKALAALAKKI L |
| 80 | Transportan 10 | AGYLLGKINLKALAALAKKIL |
| 81 | Transportan derivative 1: | GWTLNSAGYLLG |
| 82 | VP22 | DAATATRGRSAASRPTERPRAPARSA SRPRRPVD |
| 83 | VT5 | DPKGDPKGVTVTVTVTGKGDPKPD |

A "variant" of a CPP described herein refers to a peptide that is at least about 50%, preferably at least about 70%, more preferably at least about 80%-85%, preferably at least about 90%, and most preferably at least about 95%-99% identical to the original CPP upon which it is based. For example, CPPs can have substitutions at 1, 2, 3, 4 or more residues. The CPP can be used in a monomeric form or in a polymeric form such as a dimer or a trimer. A "functionally equivalent variant of a CPP" refers to a variant that has a similar cell penetration property as the original CPP. In some embodiments, the functionally equivalent variant of the CPP has an enhanced function than the original CPP. In some embodiments, the functional equivalent variant of the CPP has a diminished function as compared to the original CPP. Methods of making functionally equivalent variants are known in the art.

Additional CPP can be obtained or identified, for example, by using the mRNA display technology. In one exemplary method, a DNA library encoding random peptides is transcribed in vitro and linked to puromycin through a DNA linker, which enables the generation of an mRNA-puromycin-peptide fusion upon in vitro translation. This mRNA-peptide fusion can incubate with specific cell lines, extensively washed, and cell-penetrating peptides are recovered through RT-PCR and sequencing of the mRNAs. Multiple rounds of selection generate cell penetrating peptides that enter cells with high efficiency.

Inhibitory Peptides

The therapeutic agents used in the methods described herein comprises an inhibitory peptide that interferes with the interaction between E1A and CtBP.

The present application in some embodiments also provides inhibitory peptides described herein.

Also provided herein are compositions (such as pharmaceutical compositions) comprising any of the peptide constructs and/or conjugates described herein.

Also provided are methods of treating cancer and/or inflammatory disease comprising administering a therapeutic agent comprising an inhibitory peptide.

The inhibitory peptides described in the section above ("Peptide Constructs and Conjugates") are all encompassed in the scope of the present application, regardless of whether they are linked or associated with a cell penetrating peptide. Solely for the sake of brevity, the paragraphs below provide a non-exclusive list of these inhibitory peptides.

In one aspect, the peptide constructs and/or conjugates described herein are used to interfere with the interaction between E1A and CtBP such that their binding is reduced, and in some cases, inhibited. The reduction of E1A and CtBP binding can be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% from the amount of binding that would have occurred had the peptide constructs and/or conjugates of the present invention not been used. Assays to measure protein-protein interactions are routine and well-known in the art.

The peptide constructs described herein comprise an inhibitory peptide that interferes with the interaction between E1A and CtBP. In some embodiments, the inhibitory peptide has an IC50 of no more than about 30 µM (such as no more than about any of 20 µM, 15 µM, or 10 µM) in an in vitro binding assay. In some embodiments, the inhibitory peptide has an IC50 that is no more than the IC50 of the E1A 14mer EPGQPLDLSCKRPR (SEQ ID NO:1). In some embodiments, the inhibitor peptide binds to the same binding site on CtBP as the E1A 14mer EPGQPLDLSCKRPR (SEQ ID NO:1). In some embodiments, the inhibitor peptide competitively inhibits the binding of the E1A 14mer EPGQPLDLSCKRPR (SEQ ID NO:1) to CtBP. In some embodiments, the inhibitory peptide comprises (e.g., is) the sequence EQTVPVDLSVARPR (SEQ ID NO:132). In some embodiments, the inhibitory peptide comprises (e.g., is) the sequence GGDGPLDLCCRKRP (SEQ ID NO:133). In some embodiments, the inhibitory peptide comprises (e.g., is) the sequence PTDEPLNLSLKRPR (SEQ ID NO:134).

The peptide constructs described herein comprise an inhibitory peptide that interferes with the interaction between E1A and CtBP. In some embodiments, the inhibitory peptide has a Kd of no more than about 20 µM (such as no more than about any of 15 µM, 10 µM, 7.5 µM, 5.0 µM, or 2.5 µM) in an in vitro binding assay. In some embodiments, the inhibitory peptide has a Kd that is no more than the Kd of the E1A 14mer EPGQPLDLSCKRPR (SEQ ID NO:1). In some embodiments, the inhibitor peptide binds to the same binding site on CtBP as the E1A 14mer EPGQPLDLSCKRPR (SEQ ID NO:1). In some embodiments, the inhibitor peptide competitively inhibits the binding of the E1A 14mer EPGQPLDLSCKRPR (SEQ ID NO:1) to CtBP. In some embodiments, the inhibitory peptide comprises (e.g., is) the sequence EQTVPVDLSVARPR (SEQ ID NO:132). In some embodiments, the inhibitory peptide comprises (e.g., is) the sequence GGDGPLDLCCRKRP (SEQ ID NO:133). In some embodiments, the inhibitory peptide comprises (e.g., is) the sequence PTDEPLNLSLKRPR (SEQ ID NO:134).

In some embodiments, the inhibitory peptide comprises the sequence $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $PX_1X_2X_3X_4$ (SEQ ID NO:129), wherein $X_1$ is L, V, I, M, Q, or E, $X_2$ is D or N, $X_3$ is L or I, and $X_4$ is S, C, T, V or A.

In some embodiments, the inhibitory peptide comprises the sequence $PX_1DLS$ (SEQ ID NO:2), wherein $X_1$ is any amino acid. In some embodiments, the inhibitory peptide comprises the sequence $PX_1DLS$ (SEQ ID NO:84), wherein $X_1$ is selected from the group consisting of L, M, Q, or I. In some embodiments, the inhibitory peptide comprises the sequence PLDLS (SEQ ID NO:3).

In some embodiments, the inhibitory peptide comprises the sequence $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:128), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:128), wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $PX_1X_2X_3X_4$ (SEQ ID NO:129), wherein X1 is L, V, I, M, Q or E, $X_2$ is D or N, $X_3$ is L or I, and $X_4$ is 5, C, T, V or A, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:129), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:129), wherein $C_1$ is C, M, L, K, V or T, $C_2$ is K, A or R, $C_3$ is R, T, H, P, K or C, $C_4$ is P, 5, G, R or L, and $C_5$ is R, K, P, T, L or S. In some embodiments, the inhibitory peptide comprises the sequence $N_1N_2N_3N_4PX_1X_2X_3X_4C_1C_2C_3C_4C_5$ (SEQ ID NO:130), wherein $N_1$ is E, G, P, A or V, $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $N_1N_2N_3N_4PX_1X_2X_3X_4C_1C_2C_3C_4C_5$ (SEQ ID NO:131), wherein $N_1$ is E, G, P, A or V, $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence EQTVPVDLSVARPR (SEQ ID NO:132). In some embodiments, the inhibitory peptide comprises the sequence GGDGPLDLCCRKRP (SEQ ID NO:133). In some embodiments, the inhibitory peptide comprises the sequence PTDEPLNLSLKRPR (SEQ ID NO:134).

In some embodiments, the inhibitory peptide comprises the sequence $PX_1DLSX_2X_3$ (SEQ ID NO:4), wherein $X_1$ and $X_2$ are any amino acids, and $X_3$ is an amino acid having a bulky side chain. Amino acids having a bulky side chain include, e.g., F, W, Y, M, K, R, H and Q. In some embodiments, the inhibitory peptide comprises the sequence $PX_1DLSX_2X_3$ (SEQ ID NO:5), wherein $X_1$ and $X_2$ are any amino acids, and $X_3$ is R or K. In some embodiments, the inhibitory peptide comprises the sequence $PX_1DLSX_2K$ (SEQ ID NO:6), wherein $X_1$ and $X_2$ are any amino acids. In some embodiments, the inhibitory peptide comprises the sequence $PX_1DLSX_2Q$ (SEQ ID NO:7), wherein $X_1$ and $X_2$ are any amino acids.

In some embodiments, the inhibitory peptide comprises the sequence $PX_1DLSX_2X_3$ (SEQ ID NO:85), wherein $X_1$ is selected from the group consisting of L, M, Q, or I, $X_2$ is any amino acid, and $X_3$ is an amino acid having a bulky side chain. In some embodiments, the inhibitory peptide comprises the sequence $PX_1DLSX_2X_3$ (SEQ ID NO:86), wherein $X_1$ is selected from the group consisting of L, M, Q or I, $X_2$ is any amino acid, and $X_3$ is R or K. In some embodiments, the inhibitory peptide comprises the sequence $PX_1DLSX_2K$ (SEQ ID NO:87), wherein $X_1$ is selected from the group consisting of L, M, Q, or I, and $X_2$ is any amino acid. In some embodiments, the inhibitory peptide comprises the sequence $PX_1DLSX_2Q$ (SEQ ID NO:88), wherein $X_1$ is selected from the group consisting of L, M, Q, or I, and $X_2$ is any amino acid.

In some embodiments, the inhibitory peptide comprises the sequence $PX_1DLSX_2X_3$ (SEQ ID NO:89), wherein $X_1$ is any amino acids, $X_2$ is selected from the group consisting of C, M, L, or K, and $X_3$ is an amino acid having a bulky side chain. In some embodiments, the inhibitory peptide comprises the sequence $PX_1DLSX_2X_3$ (SEQ ID NO:90), wherein $X_1$ is any amino acids, $X_2$ is selected from the group consisting of C, M, L, or K, and $X_3$ is R or K. In some embodiments, the inhibitory peptide comprises the sequence $PX_1DLSX_2K$ (SEQ ID NO:91), wherein $X_1$ is any amino acids, $X_2$ is selected from the group consisting of C, M, L, or K. In some embodiments, the inhibitory peptide comprises the sequence $PX1DLSX2Q$ (SEQ ID NO:92), wherein $X_1$ is any amino acids, $X_2$ is selected from the group consisting of C, M, L, or K.

In some embodiments, the inhibitory peptide comprises the sequence $PX_1DLSX_2X_3$ (SEQ ID NO:93), wherein $X_1$ is selected from the group consisting of L, M, Q, or I, $X_2$ is selected from the group consisting of C, M, L, or K, and $X_3$ is an amino acid having a bulky side chain. In some embodiments, the inhibitory peptide comprises the sequence $PX_1DLSX_2X_3$ (SEQ ID NO:94), wherein $X_1$ is selected from the group consisting of L, M, Q, or I, $X_2$ is selected from the group consisting of C, M, L, or K, and $X_3$ is R or K. In some embodiments, the inhibitory peptide comprises the sequence $PX_1DLSX_2K$ (SEQ ID NO:95), wherein $X_1$ is selected from the group consisting of L, M, Q, or I, $X_2$ is selected from the group consisting of C, M, L, or K. In some embodiments, the inhibitory peptide comprises the sequence $PX_1DLSX_2Q$ (SEQ ID NO:96), wherein $X_1$ is selected from the group consisting of L, M, Q, or I, $X_2$ is selected from the group consisting of C, M, L, or K.

In some embodiments, the inhibitory peptide comprises the sequence $PLDLSX_1X_2$ (SEQ ID NO:97), wherein $X_1$ is any amino acids, and $X_2$ is an amino acid having a bulky side chain. In some embodiments, the inhibitory peptide comprises the sequence $PLDLSX_1X_2$ (SEQ ID NO:98), wherein $X_1$ is any amino acids, and $X_2$ is R or K. In some embodiments, the inhibitory peptide comprises the sequence $PLDLSX_1K$ (SEQ ID NO:99), wherein $X_1$ is any amino acid. In some embodiments, the inhibitory peptide comprises the sequence $PLDLSX_1Q$ (SEQ ID NO:100), wherein $X_1$ is any amino acid.

In some embodiments, the inhibitory peptide comprises the sequence $PLDLSX_1X_2$ (SEQ ID NO:101), wherein $X_1$ is selected from the group consisting of C, M, L, or K, and $X_2$ is an amino acid having a bulky side chain. In some embodiments, the inhibitory peptide comprises the sequence $PLDLSX_1X_2$ (SEQ ID NO:102), wherein $X_1$ is selected from the group consisting of C, M, L, or K, and $X_2$ is R or K. In some embodiments, the inhibitory peptide comprises the sequence $PLDLSX_1K$ (SEQ ID NO:103), wherein $X_1$ is selected from the group consisting of C, M, L, or K. In some embodiments, the inhibitory peptide comprises the sequence $PLDLSX_1Q$ (SEQ ID NO:104), wherein $X_1$ is selected from the group consisting of C, M, L, or K.

In some embodiments, the inhibitory peptide comprises the sequence PLDLSCK (SEQ ID NO:12). In some embodiments, the inhibitory peptide comprises the sequence PLDLSCR (SEQ ID NO:13). In some embodiments, the inhibitory peptide comprises the sequence PLDLSCQ (SEQ ID NO:14).

In some embodiments, the inhibitory peptide comprises the sequence PLDLSCKRPR (SEQ ID NO:15). In some embodiments, the inhibitory peptide comprises the sequence PLDLSCRPR (SEQ ID NO:16). In some embodiments, the inhibitory peptide comprises the sequence PLDLSCQRPR (SEQ ID NO:17). In some embodiments, the inhibitory peptide comprises the sequence PLDLSCRRPR (SEQ ID NO:122).

In some embodiments, the inhibitory peptide comprises (e.g., is) the sequence EPGQPLDLSCKRPR (SEQ ID NO:1). In some embodiments, the inhibitory peptide comprises (e.g., is) the sequence EPGQPLDLSCRPR (SEQ ID NO:105). In some embodiments, the inhibitory peptide comprises (e.g., is) the sequence EPGQPLDLSCQRPR (SEQ ID NO:19). In some embodiments, the inhibitory peptide comprises (e.g., is) the sequence EPGQPLDLSCRRPR (SEQ ID NO:123).

In some embodiments, the inhibitory peptide comprises at least 5 contiguous (such as at least about any of 10, 15, 20, 25, 30, 35, 40, 45, 50, 55, 60, or 65) amino acids of the E1A N-terminal domain (amino acids 1-67 of E1A). In some embodiments, the inhibitory peptide is at least about 80%, 85%, 90%, 95%, 98%, or 99% homologous to a portion of the E1A N-terminal domain (such as a peptides sequence having at least 5 contiguous (such as at least about any of 10, 15, 20, 25, 30, 35, 40, 45, 50, 55, 60, or 65) amino acids of the E1A N-terminal domain.

In some embodiments, the inhibitory peptide is a functionally equivalent variant of a portion of the E1A N-terminal domain (such as a peptides sequence having at least 5 contiguous (such as at least about any of 10, 15, 20, 25, 30, 35, 40, 45, 50, 55, 60, or 65) amino acids of the E1A N-terminal domain (also referred to as the "E1A inhibitory peptides").

In some embodiments, the inhibitory peptide comprises at least 5 contiguous amino acids (such as at least about any of 10, 15, 20, 25, 30, 35, 40, 45, 50, 55, 60, or 65 amino acids) of the E1A C-terminal domain (e.g., amino acids 177-243 of E1A amino acid sequence in FIG. 9). In some embodiments, the inhibitory peptide comprises an amino acid sequence that is at least about 80%, 85%, 90%, 95%, 98%, or 99% homologous to an amino acid sequence of the E1A C-terminal domain. In some embodiments, the inhibitory peptide comprises an amino acid sequence that is at least about 80%, 85%, 90%, 95%, 98%, or 99% homologous to an amino acid sequence of the E1A C-terminal domain and has at least 5 contiguous amino acids (such as at least about any of 10, 15, 20, 25, 30, 35, 40, 45, 50, 55, 60, or 65 amino acids) of the E1A C-terminal domain. In some embodiments, the inhibitory peptide is a functionally equivalent variant of a portion of the E1A C-terminal domain such as a peptide sequence having at least 5 contiguous amino acids (such as at least about any of 10, 15, 20, 25, 30, 35, 40, 45, 50, 55, 60, or 65 amino acids of the E1A C-terminal domain) of the E1A C-terminal domain. Inhibitory peptides of the embodiments herein are also referred to as "E1A inhibitory peptides".

A "variant" of an inhibitory peptide described herein refers to a peptide that is at least about 50%, preferably at least about 70%, more preferably at least about 80%-85%, preferably at least about 90%, and most preferably at least about 95%-99% identical to the original E1A inhibitory peptide upon which it is based. For example, the variant can have substitutions at 1, 2, 3, 4 or more residues. A "functionally equivalent variant" of an inhibitory peptide refers to a variant that has a similar inhibitory activity as the original inhibitory peptide. In some embodiments, the functionally equivalent variant of the inhibitory peptide has lower IC50 in inhibiting the E1A/CtBP binding than the inhibitory peptide. In some embodiments, the functionally equivalent variant of the inhibitory peptide has higher IC50 in inhibiting the E1A/CtBP binding than the inhibitory peptide. Methods of making functionally equivalent variants are described further herein. The present application thus also encompasses methods of screening for inhibitory peptides that are functionally equivalent to any one of the inhibitory peptides described herein.

Peptide Production Methods

Also provided herein are methods of making any one of the peptide constructs and conjugates described herein. The peptide construct described herein can be produced using a variety of techniques known in the art of molecular biology and protein chemistry. For example, a nucleic acid encoding a peptide construct described herein can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of peptide constructs from nucleic acids in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA* 78:2072) or Tn5 neo (Southern and Berg (1982) *Mol Appl Genet* 1:327). The selectable marker gene can be either linked to the DNA gene sequences to be expressed, or introduced into the same cell by co-transfection (Wigler et al. (1979) Cell 16:77). A second class of vectors utilizes DNA elements which confer autonomously replicating capabilities to an extrachromosomal plasmid. These vectors can be derived from animal viruses, such as bovine papillomavirus (Sarver et al. (1982) Proc Natl Acad Sci USA, 79: 7147), polyoma virus (Deans et al. (1984) *Proc Natl A cad Sci USA* 81: 1292), or SV 40 virus (Lusky and Botchan (1981) *Nature* 293:79).

The expression vectors can be introduced into cells in a manner suitable for subsequent expression of the nucleic acid. The method of introduction is largely dictated by the targeted cell type, discussed below. Exemplary methods include CaPO$_4$ precipitation, liposome fusion, lipofectin, electroporation, viral infection, dextran-mediated transfection, polybrene-mediated transfection, protoplast fusion, and direct microinjection.

Appropriate host cells for the expression of the peptide constructs include yeast, bacteria, insect, plant, and, as described above, mammalian cells. Of interest are bacteria such as *E. coli*, fungi such as *Saccharomyces cerevisiae* and *Pichia pastoris*, insect cells such as SF9, mammalian cell lines (e.g., human cell lines), as well as primary cell lines (e.g., primary mammalian cells). In some embodiments, the peptide constructs can be expressed in Chinese hamster ovary (CHO) cells or in a suitable myeloma cell line such as (NSO). Suitable cell lines also include, for example, BHK-21 (baby hamster kidney) cells; 293 (human embryonic kidney) cells; HMEpC (Human Mammary Epithelial cells; 3T3 (mouse embryonic fibroblast) cells.

The inhibitory peptide and the cell penetrating peptide may optionally be directly joined to each other, or may optionally be joined via a linker Where the inhibitory peptide and the cell penetrating peptide are directly joined, the hybrid vector is made where the DNA encoding the inhibitory peptide and the cell penetrating peptide are themselves directly ligated to each other using known scientific methods. Where a linker is used, the hybrid vector is made where the DNA encoding the inhibitory peptide is ligated to DNA encoding one end of the linker; and the DNA encoding the cell penetrating peptide is ligated to the other end of the linker Methods are known for performing such ligations in proper orientation. Such ligation may be performed either in series, or as a three way ligation. Examples of sequences which may serve as the linker sequence in the present invention include short peptides of about 2 to about 16 amino acids in length. Among the peptide sequences useful as linkers in the present invention are, e.g., (Leu-Glu)n, where n=1 to 10, Gly-Ser, and Gly.

As will be recognized by the skilled artisan, many active moieties which may be used in the present invention occur in nature as secreted proteins in conjunction with a signal or leader peptide and/or as a pro-peptide which undergoes further intra- or extra-cellular processing. In such cases, the hybrid vectors of the present invention may include one or more DNA sequences encoding such signal or leader peptides and/or one or more DNA sequences encoding such propeptide sequence, depending upon whether such secretion and/or processing is desired. Alternatively, the hybrid vectors of the present disclosure may include DNA sequences encoding a different signal or leader peptide and/or pro-peptide sequence chosen to optimize the expression and localization of the peptide construct. In most cases, the signal peptide may be omitted, as the targeting moiety will supply sufficient information for targeting of the active moiety to the desired tissue and cells within the subject's body.

In some embodiments, a peptide construct described herein can be expressed in, and purified from, transgenic animals (e.g., transgenic mammals). For example, a peptide construct described herein can be produced in transgenic non-human mammals (e.g., rodents, sheep or goats) and isolated from milk as described in, e.g., Houdebine (2002) *Curr Opin Biotechnol* 13(6):625-629; van Kuik-Romeijn et al. (2000) *Transgenic Res* 9(2): 155-159; and Pollock et al. (1999) *I Immunol Methods* 231(1-2):147-157. Additional methods for producing proteins in mammalian milk products are described in, e.g., U.S. patent application publication nos. 200600105347 and 20040006776 and U.S. Pat. No. 7,045,676.

The peptide constructs described herein can be produced from cells by culturing a host cell transformed with the expression vector containing nucleic acid encoding the peptide construct, under conditions, and for an amount of time, sufficient to allow expression of the peptide construct. Such conditions for protein expression will vary with the choice of the expression vector and the host cell, and will be easily ascertained by one skilled in the art through routine experimentation. For example, polypeptides expressed in *E. coli* can be refolded from inclusion bodies (see, e.g., Hou et al. (1998) *Cytokine* 10:319-30). Bacterial expression systems and methods for their use are well known in the art (see Current Protocols in Molecular Biology, Wiley & Sons, and Molecular Cloning-A Laboratory Manual-3rd Ed., Cold Spring Harbor Laboratory Press, New York (2001)). The choice of codons, suitable expression vectors and suitable host cells will vary depending on a number of factors, and may be easily optimized as needed. A peptide construct described herein can be expressed in mammalian cells or in other expression systems including but not limited to yeast, baculovirus, and in vitro expression systems (see, e.g., Kaszubska et al. (2000) *Protein Expression and Purification* 18:213-220).

Following expression, the peptide construct can be isolated. The term "purified" or "isolated" as applied to any of the proteins described herein (e.g., a peptide construct, a targeting moiety, and/or an active moiety) refers to a polypeptide that has been separated or purified from components (e.g., proteins or other naturally-occurring biological or organic molecules) which naturally accompany it, e.g., other proteins, lipids, and nucleic acid in a prokaryote expressing the proteins.

A peptide construct described herein can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. Ultrafiltration and diafiltration techniques, in conjunction with protein concentration, are also useful. See, e.g., Scopes (1994) "Protein Purification, 3rd edition," Springer-Verlag, New York City, N.Y. The degree of purification necessary will vary depending on the desired use. In some instances, no purification of the expressed polypeptide thereof will be necessary.

Methods for determining the yield or purity of a purified peptide construct are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

In some embodiments, a peptide construct described herein can be synthesized de novo in whole or in part, using chemical methods well known in the art. For example, the component amino acid sequences can be synthesized by solid phase techniques, cleaved from the resin, and purified by preparative high performance liquid chromatography followed by chemical linkage to form a desired peptide construct. The composition of the synthetic peptide construct may be confirmed by amino acid analysis or sequences.

In some embodiments, the peptides used in the invention can be prepared by chemical or biological methods known in the art, including solid phase peptide synthesis, solution phase peptide synthesis, and fragment condensation (either in solution phase or on solid phase).

In one embodiment, the peptides are synthesized by solid phase peptide synthesis (see Stewart and Young, Solid-Phase Peptide Synthesis, $2^{nd}$ Ed., Pierce Chemical Co. (Rockford, Ill.), 1984; Merrifield, R. B., 1963, J. Am. Chem. Soc. 85:2149-2154; Fmoc Solid Phase Peptide Synthesis: A Practical Approach (Eds. Chan and White), Oxford University Press (New York), 2000). In some embodiments, the peptide is synthesized with an L-amino acid(s) and/or a D-amino acid(s). The peptide can be synthesized and purified separately, and the peptide can be associated after synthesis and purification of both peptides have been completed. Alternatively, the peptides are synthesized either sequentially or simultaneously by synthesis on a linker which aids in maintaining the association of the peptide. For example, a branched molecule of the form $H2N_\beta$—(CH2)-CH($N_\alpha H_2$)—COOH can be attached via its carboxyl group to a solid-phase synthesis resin, such as a crosslinked benzhydrylamine or methylbenzhydrylamine resin. The $\alpha$ and $\beta$ nitrogens can be orthogonally protected (such as with a Mtt group and an Fmoc group, an ivDde group and an Fmoc group, or with an Alloc group and Fmoc group), and one chain is synthesized to the desired length, followed by synthesis of the other chain to its desired length. The covalently linked peptide construct is then cleaved from the solid phase resin and purified. The peptides can have routine modifications, such as acetylation of the N-terminal residue, amidation of the C-terminal residue, or both acetylation of the N-terminal residue and amidation of the C-terminal residue.

Once expressed and/or purified, a peptide construct described herein can be assayed for any one of a numbered of desired properties using in vitro or in vivo assays such as any of those described herein. For example, a peptide construct described herein can be assayed for its ability to inhibit E1A binding as described in Zhang et al., 2000, Acetylation of adenovirus E1A regulates binding of the transcriptional corepressor CtBP, PNAS vol. 97, no. 26: 14323-14328.

In some embodiments, endotoxin can be removed from the peptide construct preparations. Methods for removing endotoxin from a protein sample are known in the art. For example, endotoxin can be removed from a protein sample using a variety of commercially available reagents including, without limitation, the ProteoSpin™ Endotoxin Removal Kits (Norgen Biotek Corporation), Detoxi-Gel Endotoxin Removal Gel (Thermo Scientific; Pierce Protein Research Products), MiraCLEAN® Endotoxin Removal Kit (Minis), or Acrodisc™-Mustang® E membrane (Pall Corporation).

Methods for detecting and/or measuring the amount of endotoxin present in a sample (both before and after purification) are known in the art and commercial kits are available. For example, the concentration of endotoxin in a protein sample can be determined using the QCL-1000 Chromogenic kit (BioWhittaker), the limulus amebocyte lysate (LAL)-based kits such as the Pyrotell®, Pyrotell®-T, Pyrochrome®, Chromo-LAL, and CSE kits available from the Associates of Cape Cod Incorporated. Following expression and purification, the peptide constructs described herein can be modified. The modifications can be covalent or non-covalent modifications. Such modifications can be introduced into the peptide constructs by, e.g., reacting targeted amino acid residues in the targeting moiety and/or the active moiety with an organic derivatizing agent that is capable of reacting with selected side chains or terminal residues. Suitable sites for modification can be chosen using any of a variety of criteria including, e.g., structural analysis or amino acid sequence analysis of the peptide constructs described herein.

In some embodiments, the peptide constructs described herein can be modified. Following expression and purification, the peptide constructs described herein can be modified. The modifications can be covalent or non-covalent modifications. Such modifications can be introduced into the peptide constructs by, e.g., reacting targeted amino acid residues in the targeting moiety and/or the active moiety with an organic derivatizing agent that is capable of reacting with selected side chains or terminal residues. Suitable sites for modification can be chosen using any of a variety of criteria including, e.g., structural analysis or amino acid sequence analysis of the peptide constructs described herein.

In some embodiments, the peptide construct is conjugated to a carrier molecule. The carrier and the peptide construct may optionally be directly joined to each other, or may optionally be joined via a linker. Where the carrier and peptide construct are directly joined, the hybrid vector is made where the DNA encoding the carrier and peptide construct are themselves directly ligated to each other using known scientific methods. Where a linker is used, the hybrid vector is made where the DNA encoding the carrier is ligated to DNA encoding one end of the linker; and the DNA encoding the peptide construct is ligated to the other end of the linker Methods are known for performing such ligations in proper orientation. Such ligation may be performed either in series, or as a three way ligation.

Compositions and Pharmaceutical Formulations

The therapeutic agents useful for methods described herein can be provided in pharmaceutical compositions. The therapeutic agent may or may not further comprise a cell penetrating peptide such as any of the cell penetrating peptides described herein.

Also provided herein are compositions (such as pharmaceutical compositions) comprising any of the peptide constructs and/or conjugates described herein. Peptide-based therapeutics, such as the peptide constructs and/or conjugates described herein, are usually challenging to formulate. Selection of a suitable surfactant for preparing sufficiently stable emulsions for a particular application is not a predictable or routine exercise. For peptide-based therapeutics, the reduction of drug crystallization and precipitation need to be considered. Lipid-based compositions such as emulsions appear as a promising vehicle system for delivering poorly water-soluble drugs. Emulsions are an intimate mixture of two incompletely miscible liquids, such as oil and water, in which one of the liquids in the form of fine droplets is dispersed in the other liquid, usually with the aid of an emulsifier or surfactant.

In addition to the other carriers described herein, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Suitable agents which are known to enhance absorption of drugs through skin are described in Sloan, Use of Solubility Parameters from—Regular Solution Theory to Describe Partitioning-Driven Processes, Ch. 5, "Prodrugs: Topical and Ocular Drug Delivery" (Marcel Dekker, 1992), and at places elsewhere in the text. In addition, preservatives and other additives may also be present such as, for example, antimicrobials, antioxidants, chelating agents, and inert gases and the like. The peptide construct and/or conjugate may also be lyophilized using means well known in the art, for subsequent reconstitution and use according to the invention.

Thus, in some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $PX_1X_2X_3X_4$ (SEQ ID NO:129), wherein $X_1$ is L, V, I, M, Q, or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $N_4PX_1X_2X_3X_4$ (SEQ ID NO:138), wherein $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $N_4PX_1X_2X_3X_4$ (SEQ ID NO:139), wherein $N_4$ is Q, V, E or G, and wherein $X_1$ is L, V, I, M, Q or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $N_3N_4PX_1X_2X_3X_4$ (SEQ ID NO:140), wherein $N_3$ is G, T, D, E or N, and $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $N_3N_4PX_1X_2X_3X_4$ (SEQ ID NO:141), wherein $N_3$ is G, T, D, E or N, and $N_4$ is Q, V, E or G, and wherein $X_1$ is L, V, I, M, Q or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $N_2N_3N_4PX_1X_2X_3X_4$ (SEQ ID NO:142), wherein $N_2$ is P, Q, G, S, T, V or M, $N_3$ is G, T, D, E or N, and $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $N_2N_3N_4PX_1X_2X_3X_4$ (SEQ ID NO:143), wherein $N_2$ is P, Q, G, S, T, V or M, $N_3$ is G, T, D, E or N, and $N_4$ is Q, V, E or G, and wherein $X_1$ is L, V, I, M, Q or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $N_1N_2N_3N_4PX_1X_2X_3X_4$ (SEQ ID NO:144), wherein $N_1$ is E, G, P, A or V, $N_2$ is P, Q, G, S, T, V or M, $N_3$ is G, T, D, E or N, and $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $N_1N_2N_3N_4PX_1X_2X_3X_4$ (SEQ ID NO:145), wherein $N_1$ is E, G, P, A or V, $N_2$ is P, Q, G, S, T, V or M, $N_3$ is G, T, D, E or N, $N_4$ is Q, V, E or G, and wherein $X_1$ is L, V, I, M, Q or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1X_2X_3X_4C_1$ (SEQ ID NO:146), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T. In some embodiments, the inhibitory peptide comprises the sequence $PX_1X_2X_3X_4C_1$ (SEQ ID NO:147), wherein $X_1$ is L, V, I, M, Q or E, $X_2$ is D or N, $X_3$ is L or I, and $X_4$ is S, C, T, V or A, and wherein $C_1$ is C, M, L, K, V or T. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1X_2X_3X_4C_1C_2$ (SEQ ID NO:148), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T and $C_2$ is K, A or R. In some embodiments, the inhibitory peptide comprises the sequence $PX_1X_2X_3X_4C_1C_2$ (SEQ ID NO:149), wherein $X_1$ is L, V, I, M, Q or E, $X_2$ is D or N, $X_3$ is L or I, and $X_4$ is S, C, T, V or A, and wherein $C_1$ is C, M, L, K, V or T and $C_2$ is K, A or R. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1X_2X_3X_4C_1C_2C_3$ (SEQ ID NO:150), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, and $C_3$ is R, T, H, P, K or C. In some embodiments, the inhibitory peptide comprises the sequence $PX_1X_2X_3X_4C_1C_2C_3$ (SEQ ID NO:151), wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, and $C_3$ is R, T, H, P, K or C. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1X_2X_3X_4C_1C_2C_3C_4$ (SEQ ID NO:152), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, and $C_4$ is P, S, G, R or L. In some embodiments, the inhibitory peptide comprises the sequence $PX_1X_2X_3X_4C_1C_2C_3C_4$ (SEQ ID NO:153), wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, and $C_4$ is P, S, G, R or L. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1X_2X_3X_4C_1C_2C_3C_4C_5$ (SEQ ID NO:154), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $PX_1X_2X_3X_4C_1C_2C_3C_4C_5$ (SEQ ID NO:155), wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $N_4PX_1X_2X_3X_4C_1$ (SEQ ID NO:156), wherein $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T. In some embodiments, the inhibitory peptide comprises the sequence $N_4PX_1X_2X_3X_4C_1$ (SEQ ID NO:157), wherein $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $N_3N_4PX_1X_2X_3X_4C_1C_2$ (SEQ ID NO:158), wherein $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, and $C_2$ is K, A or R. In some embodiments, the inhibitory peptide comprises the sequence $N_3N_4PX_1X_2X_3X_4C_1C_2$ (SEQ ID NO:159), wherein $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, and $C_2$ is K, A or R. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $N_2N_3N_4PX_1X_2X_3X_4C_1C_2C_3$ (SEQ ID NO:160), wherein $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, and $C_3$ is R, T, H, P, K or C. In some embodiments, the inhibitory peptide comprises the sequence $N_2N_3N_4PX_1X_2X_3X_4C_1C_2C_3$ (SEQ ID NO:161), wherein $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, and $C_3$ is R, T, H, P, K or C. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $N_1N_2N_3N_4PX_1X_2X_3X_4C_1C_2C_3C_4$ (SEQ ID NO:162), wherein $N_1$ is E, G, P, A or V, $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, and $C_4$ is P, S, G, R or L. In some embodiments, the inhibitory peptide comprises the sequence $N_1N_2N_3N_4PX_1X_2X_3X_4C_1C_2C_3C_4$(SEQ ID NO:163), wherein $N_1$ is E, G, P, A or V, $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, and $C_4$ is P, S, G, R or L. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:128), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:128), wherein $C_1$ is C, M, L, K, V or T, $C_2$ is K, A or R, $C_3$ is R, T, H, P, K or C, $C_4$ is P, 5, G, R or L, and $C_5$ is R, K, P, T, L or S. In some embodiments, the inhibitory peptide comprises $PX_1X_2X_3X_4$ (SEQ ID NO:129), wherein X1 is L, V, I, M, Q or E, $X_2$ is D or N, $X_3$ is L or I, and $X_4$ is 5, C, T, V or A, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:129), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:129), wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $N_1N_2N_3N_4PX_1X_2X_3X_4C_1C_2C_3C_4C_5$ (SEQ ID NO:130), wherein $N_1$ is E, G, P, A or V, $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, $C_4$ is P, 5, G, R or L, and $C_5$ is R, K, P, T, L or S. In some embodiments, the inhibitory peptide comprises the sequence $N_1N_2N_3N_4PX_1X_2X_3X_4C_1C_2C_3C_4C_5$ (SEQ ID NO:131), wherein $N_1$ is E, G, P, A or V, $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence EQTVPVDLS-VARPR (SEQ ID NO:132). In some embodiments, the inhibitory peptide comprises the sequence GGDGPLDLC-CRKRP (SEQ ID NO:133). In some embodiments, the inhibitory peptide comprises the sequence PTDEPLN-LSLKRPR (SEQ ID NO:134). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

Thus, in some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1DLS$ (SEQ ID NO:2), wherein $X_1$ is any amino acid. In some embodiments, the inhibitory peptide comprises the sequence PLDLS (SEQ ID NO:3). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP, wherein the inhibitory peptide comprises the sequence $PX_1DLSX_2X_3$ (SEQ ID NO:4), wherein $X_1$ and $X_2$ are any amino acids, and $X_3$ is an amino acid having a bulky side chain (such as R or K). In some embodiments, the inhibitory peptide comprises the sequence $PX_1DLSX_2K$ (SEQ ID NO:6), wherein $X_1$ and $X_2$ are any amino acids. In some embodiments, the inhibitory peptide comprises the sequence $PLDLSX_1K$ (SEQ ID NO:10), wherein $X_1$ is any amino acid. In some embodiments, the inhibitory peptide comprises the sequence PLDLSCK (SEQ ID NO:12). In some embodiments, the inhibitory peptide comprises the sequence PLDLSCKRPR (SEQ ID NO:15). In some embodiments, the inhibitory peptide comprises (e.g., is) the sequence EPGQPLDLSCK-RPR (SEQ ID NO:1). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO:20. In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO:22. In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO:26. In some embodiments, there is provided a composition (such as a pharmaceutical composition) comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO:28.

A variety of excipients usually utilized in the pharmaceutical arts can be added to the pharmaceutical compositions of the invention. These pharmaceutically acceptable excipients may be preserving agents, emollients, antifoaming agents, antioxidants, buffers, pigments, coloring agents, sweetening agents, flavoring agents, coating agents, granulating agents, disintegrants, glidants, lubricants, conventional matrix materials, complexing agents, absorbents, and fillers. Suitable excipients include, but are not limited to metilparaben, propilparaben, cyclodextrin, liquid paraffin, dimethicone, Abil EM 90 (silicone). In some embodiments, the excipient is any of: liquid paraffin, methylparaben, propylparaben, cetrimide and cetostearyl alcohol.

Methods of Treating Cancer

The peptide constructs, conjugates, and compositions (such as pharmaceutical compositions) described herein are useful for treatment of diseases such as cancer. The peptide constructs can be delivered to an individual via a variety of routes, including, but not limited to, intravenous, intratumoral, subcutaneously, oral, transmucosal, transdermal, and topical administrations. The present application thus also encompasses methods of delivering any of the peptide constructs or conjugates described herein to an individual (such as an individual having cancer).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $PX_1X_2X_3X_4$ (SEQ ID NO:129), wherein $X_1$ is L, V, I, M, Q, or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1DLS$ (SEQ ID NO:2), wherein $X_1$ is any amino acid. In some embodiments, the inhibitory peptide comprises the sequence PLDLS (SEQ ID NO:3). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $N_4PX_1X_2X_3X_4$ (SEQ ID NO:138), wherein $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $N_4PX_1X_2X_3X_4$ (SEQ ID NO:139), wherein $N_4$ is Q, V, E or G, and wherein $X_1$ is L, V, I, M, Q or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $N_3N_4PX_1X_2X_3X_4$ (SEQ ID NO:140), wherein $N_3$ is G, T, D, E or N, and $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $N_3N_4PX_1X_2X_3X_4$ (SEQ ID NO:141), wherein $N_3$ is G, T, D, E or N, and $N_4$ is Q, V, E or G, and wherein $X_1$ is L, V, I, M, Q or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $N_2N_3N_4PX_1X_2X_3X_4$ (SEQ ID NO:142), wherein $N_2$ is P, Q, G, S, T, V or M, $N_3$ is G, T, D, E or N, and $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, there is provided a conjugate comprising a peptide construct and a carrier molecule, wherein the peptide construct comprises a cell penetrating peptide and an inhibitory peptide that interferes with the interaction between E1A and CtBP, wherein the inhibitory peptide comprises the sequence $N_2N_3N_4PX_1X_2X_3X_4$ (SEQ ID NO:143), wherein $N_2$ is P, Q, G, S, T, V or M, $N_3$ is G, T, D, E or N, and $N_4$ is Q, V, E or G, and wherein $X_1$ is L, V, I, M, Q or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $N_1N_2N_3N_4PX_1X_2X_3X_4$ (SEQ ID NO:144), wherein $N_1$ is E, G, P, A or V, $N_2$ is P, Q, G, S, T, V or M, $N_3$ is G, T, D, E or N, and $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $N_1N_2N_3N_4PX_1X_2X_3X_4$ (SEQ ID NO:145), wherein $N_1$ is E, G, P, A or V, $N_2$ is P, Q, G, S, T, V or M, $N_3$ is G, T, D, E or N, $N_4$ is Q, V, E or G, and wherein $X_1$ is L, V, I, M, Q or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1X_2X_3X_4C_1$ (SEQ ID NO:146), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T. In some embodiments, the inhibitory peptide comprises the sequence $PX_1X_2X_3X_4C_1$ (SEQ ID NO:147), wherein $X_1$ is L, V, I, M, Q or E, $X_2$ is D or N, $X_3$ is L or I, and $X_4$ is S, C, T, V or A, and wherein $C_1$ is C, M, L, K, V or T. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1X_2X_3X_4C_1C_2$ (SEQ ID NO:148), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T and $C_2$ is K, A or R. In some embodiments, the inhibitory peptide comprises the sequence $PX_1X_2X_3X_4C_1C_2$ (SEQ ID NO:149), wherein $X_1$ is L, V, I, M, Q or E, $X_2$ is D or N, $X_3$ is L or I, and $X_4$ is S, C, T, V or A, and wherein $C_1$ is C, M, L, K, V or T and $C_2$ is K, A or R. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1X_2X_3X_4C_1C_2C_3$ (SEQ ID NO:150), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, and $C_3$ is R, T, H, P, K or C. In some embodiments, the inhibitory peptide comprises the sequence $PX_1X_2X_3X_4C_1C_2C_3$ (SEQ ID NO:151), wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, and $C_3$ is R, T, H, P, K or C. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1X_2X_3X_4C_1C_2C_3C_4$ (SEQ ID NO:152), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, and $C_4$ is P, S, G, R or L. In some embodiments, the inhibitory peptide comprises the sequence $PX_1X_2X_3X_4C_1C_2C_3C_4$ (SEQ ID NO:153), wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, and $C_4$ is P, S, G, R or L. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1X_2X_3X_4C_1C_2C_3C_4C_5$ (SEQ ID NO:154), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $PX_1X_2X_3X_4C_1C_2C_3C_4C_5$ (SEQ ID NO:155), wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $N_4PX_1X_2X_3X_4C_1$ (SEQ ID NO:156), wherein $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T. In some embodiments, the inhibitory peptide comprises the sequence $N_4PX_1X_2X_3X_4C_1$ (SEQ ID NO:157), wherein $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $N_3N_4PX_1X_2X_3X_4C_1C_2$ (SEQ ID NO:158), wherein $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, and $C_2$ is K, A or R. In some embodiments, the inhibitory peptide comprises the sequence $N_3N_4PX_1X_2X_3X_4C_1C_2$ (SEQ ID NO:159), wherein $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, and $C_2$ is K, A or R. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $N_2N_3N_4PX_1X_2X_3X_4C_1C_2C_3$ (SEQ ID NO:160), wherein $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, and $C_3$ is R, T, H, P, K or C. In some embodiments, the inhibitory peptide comprises the sequence $N_2N_3N_4PX_1X_2X_3X_4C_1C_2C_3$ (SEQ ID NO:161), wherein $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, and $C_3$ is R, T, H, P, K or C. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $N_1N_2N_3N_4PX_1X_2X_3X_4C_1C_2C_3C_4$ (SEQ ID NO:162), wherein $N_1$ is E, G, P, A or V, $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, and $C_4$ is P, S, G, R or L. In some embodiments, the inhibitory peptide comprises the sequence $N_1N_2N_3N_4PX_1X_2X_3X_4C_1C_2C_3C_4$ (SEQ ID NO:163), wherein N1 is E, G, P, A or V, $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, and $C_4$ is P, S, G, R or L. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:128), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:128), wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $PX_1X_2X_3X_4$ (SEQ ID NO:129), wherein X1 is L, V, I, M, Q or E, $X_2$ is D or N, $X_3$ is L or I, and $X_4$ is 5, C, T, V or A, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:129), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:129), wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $N_1N_2N_3N_4PX_1X_2X_3X_4C_1C_2C_3C_4C_5$ (SEQ ID NO:130), wherein $N_1$ is E, G, P, A or V, $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, $C_4$ is P, 5, G, R or L, and $C_5$ is R, K, P, T, L or S. In some embodiments, the inhibitory peptide comprises the sequence $N_1N_2N_3N_4PX_1X_2X_3X_4C_1C_2C_3C_4C_5$ (SEQ ID NO:131), wherein $N_1$ is E, G, P, A or V, $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is 5, C, T, V or A, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence EQTVPVDLSVARPR (SEQ ID NO:132). In some embodiments, the inhibitory peptide comprises the sequence GGDGPLDLCCRKRP (SEQ ID NO:133). In some embodiments, the inhibitory peptide comprises the sequence PTDEPLNLSLKRPR (SEQ ID NO:134). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the inhibitory peptide comprises the sequence $PX_1DLSX_2X_3$ (SEQ ID NO:4), wherein $X_1$ and $X_2$ are any amino acids, and $X_3$ is an amino acid having a bulky side chain (such as R or K). In some embodiments, the inhibitory peptide comprises the sequence $PX_1DLSX_2K$ (SEQ ID NO:6), wherein $X_1$ and $X_2$ are any amino acids. In some embodiments, the inhibitory peptide comprises the sequence $PLDLSX_1K$ (SEQ ID NO:10), wherein $X_1$ is any amino acid. In some embodiments, the inhibitory peptide comprises the sequence PLDLSCK (SEQ ID NO:12). In some embodiments, the inhibitory peptide comprises the sequence PLDLSCKRPR (SEQ ID NO:15). In some embodiments, the inhibitory peptide comprises (e.g., is) the sequence EPGQPLDLSCKRPR (SEQ ID NO:1). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO:20. In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO:22. In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO:26. In some embodiments, there is provided a method of treating cancer in an individual comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO:28.

In some embodiments, there is provided a method of inhibiting cell proliferation, cell migration, or angiogenesis in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $PX_1X_2X_3X_4$ (SEQ ID NO:129), wherein $X_1$ is L, V, I, M, Q, or E, $X_2$ is D or N, $X_3$ is L or I, and $X_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of inhibiting cell proliferation, cell migration, or angiogenesis in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence $PX_1DLS$ (SEQ ID NO:2), wherein $X_1$ is any amino acid. In some embodiments, the inhibitory peptide comprises the sequence PLDLS (SEQ ID NO:3). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of inhibiting cell proliferation, cell migration, or angiogenesis in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the inhibitory peptide comprises the sequence $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:128), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:128), wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $PX_1X_2X_3X_4$ (SEQ ID NO:129), wherein X1 is L, V, I, M, Q or E, $X_2$ is D or N, $X_3$ is L or I, and $X_4$ is 5, C, T, V or A, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:129), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:129), wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $N_1N_2N_3N_4PX_1X_2X_3X_4C_1C_2C_3C_4C_5$ (SEQ ID NO:130), wherein $N_1$ is E, G, P, A or V, $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $N_1N_2N_3N_4PX_1X_2X_3X_4C_1C_2C_3C_4C_5$ (SEQ ID NO:131), wherein $N_1$ is E, G, P, A or V, $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is 5, C, T, V or A, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence EQTVPVDLS-VARPR (SEQ ID NO:132). In some embodiments, the inhibitory peptide comprises the sequence GGDGPLDLC-CRKRP (SEQ ID NO:133). In some embodiments, the inhibitory peptide comprises the sequence PTDEPLN-LSLKRPR (SEQ ID NO:134). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of inhibiting cell proliferation, cell migration, or angiogenesis in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the inhibitory peptide comprises the sequence PX$_1$DLSX$_2$X$_3$ (SEQ ID NO:4), wherein X$_1$ and X$_2$ are any amino acids, and X$_3$ is an amino acid having a bulky side chain (such as R or K). In some embodiments, the inhibitory peptide comprises the sequence PX$_1$DLSX$_2$K (SEQ ID NO:6), wherein X$_1$ and X$_2$ are any amino acids. In some embodiments, the inhibitory peptide comprises the sequence PLDLSX$_1$K (SEQ ID NO:10), wherein X$_1$ is any amino acid. In some embodiments, the inhibitory peptide comprises the sequence PLDLSCK (SEQ ID NO:12). In some embodiments, the inhibitory peptide comprises the sequence PLDLSCKRPR (SEQ ID NO:15). In some embodiments, the inhibitory peptide comprises (e.g., is) the sequence EPGQPLDLSCKRPR (SEQ ID NO:1). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of inhibiting cell proliferation, cell migration, or angiogenesis in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO:20. In some embodiments, there is provided a method of inhibiting cell proliferation, cell migration, or angiogenesis in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO:22. In some embodiments, there is provided a method of inhibiting cell proliferation, cell migration, or angiogenesis in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO:26. In some embodiments, there is provided a method of inhibiting cell proliferation, cell migration, or angiogenesis in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO:28.

In some embodiments, there is provided a method of decreasing resistance to radiation and chemotherapy in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence PX$_1$X$_2$X$_3$X$_4$ (SEQ ID NO:128), wherein X$_1$ is a hydrophobic residue, X$_2$ is a residue that preserves hydrogen bonding with CtBP, X$_3$ is a hydrophobic residue, and X$_4$ is a residue that preserves hydrogen bonding with CtBP. In some embodiments, the inhibitory peptide comprises the sequence PX$_1$X$_2$X$_3$X$_4$ (SEQ ID NO:129), wherein X$_1$ is L, V, I, M, Q, or E, X$_2$ is D or N, X$_3$ is L or I, and X$_4$ is S, C, T, V or A. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of decreasing resistance to radiation and chemotherapy in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP. In some embodiments, the inhibitory peptide comprises the sequence PX$_1$DLS (SEQ ID NO:2), wherein X$_1$ is any amino acid. In some embodiments, the inhibitory peptide comprises the sequence PLDLS (SEQ ID NO:3). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of decreasing resistance to radiation and chemotherapy in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the inhibitory peptide comprises the sequence PX$_1$X$_2$X$_3$X$_4$ (SEQ ID NO:128), wherein X$_1$ is a hydrophobic residue, X$_2$ is a residue that preserves hydrogen bonding with CtBP, X$_3$ is a hydrophobic residue, and X$_4$ is a residue that preserves hydrogen bonding with CtBP, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:128), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:128), wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $PX_1X_2X_3X_4$ (SEQ ID NO:129), wherein X1 is L, V, I, M, Q or E, $X_2$ is D or N, $X_3$ is L or I, and $X_4$ is 5, C, T, V or A, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:129), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:129), wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $N_1N_2N_3N_4PX_1X_2X_3X_4C_1C_2C_3C_4C_5$ (SEQ ID NO:130), wherein $N_1$ is E, G, P, A or V, $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $N_1N_2N_3N_4PX_1X_2X_3X_4C_1C_2C_3C_4C_5$ (SEQ ID NO:131), wherein $N_1$ is E, G, P, A or V, $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is 5, C, T, V or A, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence EQTVPVDLSVARPR (SEQ ID NO:132). In some embodiments, the inhibitory peptide comprises the sequence GGDGPLDLCCRKRP (SEQ ID NO:133). In some embodiments, the inhibitory peptide comprises the sequence PTDEPLNLSLKRPR (SEQ ID NO:134). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of decreasing resistance to radiation and chemotherapy in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the inhibitory peptide comprises the sequence $PX_1DLSX_2X_3$ (SEQ ID NO:4), wherein $X_1$ and $X_2$ are any amino acids, and $X_3$ is an amino acid having a bulky side chain (such as R or K). In some embodiments, the inhibitory peptide comprises the sequence $PX_1DLSX_2K$ (SEQ ID NO:6), wherein $X_1$ and $X_2$ are any amino acids. In some embodiments, the inhibitory peptide comprises the sequence $PLDLSX_1K$ (SEQ ID NO:10), wherein $X_1$ is any amino acid. In some embodiments, the inhibitory peptide comprises the sequence PLDLSCK (SEQ ID NO:12). In some embodiments, the inhibitory peptide comprises the sequence PLDLSCKRPR (SEQ ID NO:15). In some embodiments, the inhibitory peptide comprises (e.g., is) the sequence EPGQPLDLSCKRPR (SEQ ID NO:1). In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of decreasing resistance to radiation and chemotherapy in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO:20. In some embodiments, there is provided a method of decreasing resistance to radiation and chemotherapy in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO:22. In some embodiments, there is provided a method of decreasing resistance to radiation and chemotherapy in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO:26. In some embodiments, there is provided a method of decreasing resistance to radiation and chemotherapy in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO:28. In some embodiments, there is provided a method of decreasing resistance to radiation and chemotherapy in an individual having cancer, comprising administering to the individual an effective amount of a pharmaceutical composition comprising a peptide construct (or a conjugate comprising the peptide construct), wherein the peptide construct comprises a cell penetrating peptide and an inhibitory peptide that interferes with the interaction between E1A and CtBP, wherein the peptide construct comprises (e.g., is) SEQ ID NO: 26.

In some embodiments, the cancer is breast cancer. In some embodiments, the cancer is ovarian cancer. In some embodiments, the cancer is gastric cancer. In some embodiments, the cancer is glioma. In some embodiments, the cancer is skin cancer. In some embodiments, the cancer is melanoma. In some embodiments, the cancer is colon cancer. In some embodiments, the cancer is poorly differentiated colon adenocarcinoma. In some embodiments, the cancer is lung cancer. In some embodiments, the cancer is non-small cell lung cancer. In some embodiments, the lung cancer is moderately differentiated lung adenocarcinoma. In some embodiments, the cancer is ductal invasive breast carcinoma. In some embodiments, the cancer is renal cell carcinoma.

Methods of Treating Inflammatory Diseases

The present application in some embodiments provide methods of treating inflammatory diseases in an individual by administering to the individual an effective amount of a therapeutic agent comprising an inhibitory peptide that interferes with the interaction between E1A and CtBP. The therapeutic agents can be delivered to an individual via a variery of routes, including, but not limited to, intravenous, intratumoral, subcutaneously, oral, transmucosal, transdermal, and topical administrations. The present application thus also encompasses methods of delivering any of the therapeutic agents described herein to an individual (such as an individual having an inflammatory disease).

The therapeutic agent in some embodiments comprisings a peptide construct comprising a cell penetration peptide and an inhibitory peptide that interferes with the interaction between E1A and CtBP. In some embodiments, the therapeutic agent comprises an inhibitory peptide not linked to a cell penetration peptide.

In some embodiments, there is provided a method of treating an inflammatory disease (such as psoriasis) in an individual comprising administering to the indivudal an effective amount of a therapeutic agent comprising inhibitory peptide that interferes with the interaction between E1A and CtBP. In some embodiments, the inhibitory peptide comprises the sequence $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $PX_1X_2X_3X_4$ (SEQ ID NO:129), wherein $X_1$ is L, V, I, M, Q, or E, $X_2$ is D or N, $X_3$ is L or I, and $X_4$ is S, C, T, V or A. In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the indivudal an effective amount of a therapeutic agent comprising inhibitory peptide that interferes with the interaction between E1A and CtBP. In some embodiments, the inhibitory peptide comprises the sequence $P X_1 DLS$ (SEQ ID NO:2), wherien $X_1$ is any amino acid. In some embodiments, the inhibitory peptide comprises the sequence PLDLS (SEQ ID NO:3). In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the indivudal an effective amount of a therapeutic agent comprising an inhibitory peptide that interferes with the interaction between E1A and CtBP, wherein the inhibitory peptide comprises the sequence $N_4PX_1X_2X_3X_4$ (SEQ ID NO:138), wherein $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $N_4PX_1X_2X_3X_4$ (SEQ ID NO:139), wherein $N_4$ is Q, V, E or G, and wherein $X_1$ is L, V, I, M, Q or E, $X_2$ is D or N, $X_3$ is L or I, and $X_4$ is S, C, T, V or A. In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the indivudal an effective amount of a therapeutic agent comprising an inhibitory peptide that interferes with the interaction between E1A and CtBP, wherein the inhibitory peptide comprises the sequence $N_3N_4PX_1X_2X_3X_4$ (SEQ ID NO:140), wherein $N_3$ is G, T, D, E or N, and $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $N_3N_4PX_1X_2X_3X_4$ (SEQ ID NO:141), wherein $N_3$ is G, T, D, E or N, and $N_4$ is Q, V, E or G, and wherein $X_1$ is L, V, I, M, Q or E, $X_2$ is D or N, $X_3$ is L or I, and $X_4$ is S, C, T, V or A. In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the indivudal an effective amount of a therapeutic agent comprising an inhibitory peptide that interferes with the interaction between E1A and CtBP, wherein the inhibitory peptide comprises the sequence $N_2N_3N_4PX_1X_2X_3X_4$ (SEQ ID NO:142), wherein $N_2$ is P, Q, G, S, T, V or M, $N_3$ is G, T, D, E or N, and $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $N_2N_3N_4PX_1X_2X_3X_4$ (SEQ ID NO:143), wherein $N_2$ is P, Q, G, S, T, V or M, $N_3$ is G, T, D, E or N, and $N_4$ is Q, V, E or G, and wherein $X_1$ is L, V, I, M, Q or E, X2 is D or N, $X_3$ is L or I, and $X_4$ is S, C, T, V or A. In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the indivudal an effective amount of a therapeutic agent comprising an inhibitory peptide that interferes with the interaction between E1A and CtBP, wherein the inhibitory peptide comprises the sequence $N_1N_2N_3N_4PX_1X_2X_3X_4$ (SEQ ID NO:144), wherein $N_1$ is E, G, P, A or V, $N_2$ is P, Q, G, S, T, V or M, $N_3$ is G, T, D, E or N, and $N_4$ is Q, V, E or G, and wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $N_1N_2N_3N_4PX_1X_2X_3X_4$ (SEQ ID NO:145), wherein $N_1$ is E, G, P, A or V, $N_2$ is P, Q, G, S, T, V or M, $N_3$ is G, T, D, E or N, $N_4$ is Q, V, E or G, and wherein $X_1$ is L, V, I, M, Q or E, $X_2$ is D or N, $X_3$ is L or I, and $X_4$ is S, C, T, V or A. In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the indivudal an effective amount of a therapeutic agent comprising an inhibitory peptide that interferes with the interaction between E1A and CtBP, wherein the inhibitory peptide comprises the sequence $PX_1X_2X_3X_4C_1$ (SEQ ID NO:146), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T. In some embodiments, the inhibitory peptide comprises the sequence $PX_1X_2X_3X_4C_1$ (SEQ ID NO:147), wherein $X_1$ is L, V, I, M, Q or E, $X_2$ is D or N, $X_3$ is L or I, and $X_4$ is S, C, T, V or A, and wherein $C_1$ is C, M, L, K, V or T. In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the indivudal an effective amount of a therapeutic agent comprising an inhibitory peptide that interferes with the interaction between E1A and CtBP, wherein the inhibitory peptide comprises the sequence $PX_1X_2X_3X_4C_1C_2$ (SEQ ID NO:148), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T and $C_2$ is K, A or R. In some embodiments, the inhibitory peptide comprises the sequence $PX_1X_2X_3X_4C_1C_2$ (SEQ ID NO:149), wherein $X_1$ is L, V, I, M, Q or E, $X_2$ is D or N, $X_3$ is L or I, and $X_4$ is S, C, T, V or A, and wherein $C_1$ is C, M, L, K, V or T and $C_2$ is K, A or R. In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the indivudal an effective amount of a therapeutic agent comprising an inhibitory peptide that interferes with the interaction between E1A and CtBP, wherein the inhibitory peptide comprises the sequence $PX_1X_2X_3X_4C_1C_2C_3$ (SEQ ID NO:150), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, and $C_3$ is R, T, H, P, K or C. In some embodiments, the inhibitory peptide comprises the sequence $PX_1X_2X_3X_4C_1C_2C_3$ (SEQ ID NO:151), wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, and $C_3$ is R, T, H, P, K or C. In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the indivudal an effective amount of a therapeutic agent comprising an inhibitory peptide that interferes with the interaction between E1A and CtBP, wherein the inhibitory peptide comprises the sequence $PX_1X_2X_3X_4C_1C_2C_3C_4$ (SEQ ID NO:152), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, and $C_4$ is P, S, G, R or L. In some embodiments, the inhibitory peptide comprises the sequence $PX_1X_2X_3X_4C_1C_2C_3C_4$ (SEQ ID NO:153), wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, and $C_4$ is P, S, G, R or L. In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the indivudal an effective amount of a therapeutic agent comprising an inhibitory peptide that interferes with the interaction between E1A and CtBP, wherein the inhibitory peptide comprises the sequence $PX_1X_2X_3X_4C_1C_2C_3C_4C_5$ (SEQ ID NO:154), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $PX_1X_2X_3X_4C_1C_2C_3C_4C_5$ (SEQ ID NO:155), wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the indivudal an effective amount of a therapeutic agent comprising an inhibitory peptide that interferes with the interaction between E1A and CtBP, wherein the inhibitory peptide comprises the sequence $N_4PX_1X_2X_3X_4C_1$ (SEQ ID NO:156), wherein $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T. In some embodiments, the inhibitory peptide comprises the sequence $N_4PX_1X_2X_3X_4C_1$ (SEQ ID NO:157), wherein $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T. In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the indivudal an effective amount of a therapeutic agent comprising an inhibitory peptide that interferes with the interaction between E1A and CtBP, wherein the inhibitory peptide comprises the sequence $N_3N_4PX_1X_2X_3X_4C_1C_2$ (SEQ ID NO:158), wherein $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, and $C_2$ is K, A or R. In some embodiments, the inhibitory peptide comprises the sequence $N_3N_4PX_1X_2X_3X_4C_1C_2$ (SEQ ID NO:159), wherein $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, and $C_2$ is K, A or R. In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the indivudal an effective amount of a therapeutic agent comprising an inhibitory peptide that interferes with the interaction between E1A and CtBP, wherein the inhibitory peptide comprises the sequence $N_2N_3N_4PX_1X_2X_3X_4C_1C_2C_3$ (SEQ ID NO:160), wherein $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, and $C_3$ is R, T, H, P, K or C. In some embodiments, the inhibitory peptide comprises the sequence $N_2N_3N_4PX_1X_2X_3X_4C_1C_2C_3$ (SEQ ID NO:161), wherein $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, and $C_3$ is R, T, H, P, K or C. In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the indivudal an effective amount of a therapeutic agent comprising an inhibitory peptide that interferes with the interaction between E1A and CtBP, wherein the inhibitory peptide comprises the sequence $N_1N_2N_3N_4PX_1X_2X_3X_4C_1C_2C_3C_4$ (SEQ ID NO:162), wherein $N_1$ is E, G, P, A or V, $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, and $C_4$ is P, S, G, R or L. In some embodiments, the inhibitory peptide comprises the sequence $N_1N_2N_3N_4PX_1X_2X_3X_4C_1C_2C_3C_4$ (SEQ ID NO:163), wherein $N_1$ is E, G, P, A or V, $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is S, C, T, V or A, and wherein $C_1$ is C, M, L, K, V or T, $C_2$ is K, A or R, $C_3$ is R, T, H, P, K or C, and $C_4$ is P, S, G, R or L. In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the individual an effective amount of a therapeutic agent comprising an inhibitory peptide that interferes with the interaction between E1A and CtBP, wherein the inhibitory peptide comprises the sequence $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and further comprises one of $N_4$, $N_3N_4$, $N_2N_3N_4$, or $N_1N_2N_3N_4$ (SEQ ID NO:164) at the N-terminus of PX$_1$X$_2$X$_3$X$_4$ (SEQ ID NO:128), wherein N$_1$ is E, G, P, A or V, N$_2$ is P, Q, G, S, T, V or M, N$_3$ is G, T, D, E or N, and N$_4$ is Q, V, E or G, and/or further comprises one of C$_1$, C$_1$C$_2$, C$_1$C$_2$C$_3$, C$_1$C$_2$C$_3$C$_4$ (SEQ ID NO:165), or C$_1$C$_2$C$_3$C$_4$C$_5$ (SEQ ID NO:166) at the C-terminus of PX$_1$X$_2$X$_3$X$_4$ (SEQ ID NO:128), wherein C$_1$ is C, M, L, K, V or T, C$_2$ is K, A or R, C$_3$ is R, T, H, P, K or C, C$_4$ is P, S, G, R or L, and C$_5$ is R, K, P, T, L or S. In some embodiments, the inhibitory peptide comprises PX$_1$X$_2$X$_3$X$_4$ (SEQ ID NO:129), wherein X1 is L, V, I, M, Q or E, X$_2$ is D or N, X$_3$ is L or I, and X$_4$ is 5, C, T, V or A, and further comprises one of N$_4$, N$_3$N$_4$, N$_2$N$_3$N$_4$, or N$_1$N$_2$N$_3$N$_4$ (SEQ ID NO:164) at the N-terminus of PX$_1$X$_2$X$_3$X$_4$ (SEQ ID NO:129), wherein N$_1$ is E, G, P, A or V, N$_2$ is P, Q, G, S, T, V or M, N$_3$ is G, T, D, E or N, and N$_4$ is Q, V, E or G, and/or further comprises one of C$_1$, C$_1$C$_2$, C$_1$C$_2$C$_3$, C$_1$C$_2$C$_3$C$_4$ (SEQ ID NO:165), or C$_1$C$_2$C$_3$C$_4$C$_5$ (SEQ ID NO:166) at the C-terminus of PX$_1$X$_2$X$_3$X$_4$ (SEQ ID NO:129), wherein C$_1$ is C, M, L, K, V or T, C$_2$ is K, A or R, C$_3$ is R, T, H, P, K or C, C$_4$ is P, S, G, R or L, and C$_5$ is R, K, P, T, L or S. In some embodiments, the inhibitory peptide comprises the sequence N$_1$N$_2$N$_3$N$_4$PX$_1$X$_2$X$_3$X$_4$C$_1$C$_2$C$_3$C$_4$C$_5$ (SEQ ID NO:130), wherein N$_1$ is E, G, P, A or V, N$_2$ is P, Q, G, S, T, V or M, N$_3$ is G, T, D, E or N, and N$_4$ is Q, V, E or G, wherein X$_1$ is a hydrophobic residue, X$_2$ is a residue that preserves hydrogen bonding with CtBP, X$_3$ is a hydrophobic residue, and X$_4$ is a residue that preserves hydrogen bonding with CtBP, and wherein C$_1$ is C, M, L, K, V or T, C$_2$ is K, A or R, C$_3$ is R, T, H, P, K or C, C$_4$ is P, S, G, R or L, and C$_5$ is R, K, P, T, L or S. In some embodiments, the inhibitory peptide comprises the sequence N$_1$N$_2$N$_3$N$_4$PX$_1$X$_2$X$_3$X$_4$C$_1$C$_2$C$_3$C$_4$C$_5$ (SEQ ID NO:131), wherein N$_1$ is E, G, P, A or V, N$_2$ is P, Q, G, S, T, V or M, N$_3$ is G, T, D, E or N, and N$_4$ is Q, V, E or G, wherein X$_1$ is L, V, I, M, Q or E, X$_2$ is D or N, X$_3$ is L or I, and X$_4$ is 5, C, T, V or A, and wherein C$_1$ is C, M, L, K, V or T, C$_2$ is K, A or R, C$_3$ is R, T, H, P, K or C, C$_4$ is P, S, G, R or L, and C$_5$ is R, K, P, T, L or S. In some embodiments, the inhibitory peptide comprises the sequence EQTVPVDLSVARPR (SEQ ID NO:132). In some embodiments, the inhibitory peptide comprises the sequence GGDGPLDLCCRKRP (SEQ ID NO:133). In some embodiments, the inhibitory peptide comprises the sequence PTDEPLNLSLKRPR (SEQ ID NO:134). In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the indivudal an effective amount of a therapeutic agent comprising an inhibitory peptide that interferes with the interaction between E1A and CtBP, wherein the inhibitory peptide comprises the sequence PX$_1$DLSX$_2$X$_3$ (SEQ ID NO:4), wherien X$_1$ and X$_2$ are any amino acids, and X$_3$ is an amino acid having a bulky side chain. In some embodiments, the inhibitory peptide comprises the sequence PX$_1$DLSX$_2$K (SEQ ID NO:6), wherien X$_1$ and X$_2$ are any amino acids. In some embodiments, the inhibitory peptide comprises the sequence PLDLSX$_1$K (SEQ ID NO:10), wherein X$_1$ is any amino acid. In some embodiments, the inhibitory peptide comprises the sequence PLDLSCK (SEQ ID NO:12). In some embodiments, the inhibitory peptide comprises the sequence PLDLSCKRPR (SEQ ID NO:15). In some embodiments, the inhibitory peptide comprises (e.g., is) the sequence EPGQPLDLSCKRPR (SEQ ID NO:1). In some embodiments, the therapeutic agent comprises a peptide construct comprising the inhibitory peptide and a cell penetration peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of treating an inflammatory disease (such as psoriasis) in an individual comprising administering to the indivudal an effective amount of a therapeutic agent comprising a peptide construct comprising (e.g., is) SEQ ID NO 20. In some embodiments, there is provided a method of treating an inflammatory disease (such as psoriasis) in an individual comprising administering to the indivudal an effective amount of a therapeutic agent comprising a peptide construct comprising (e.g., is) SEQ ID NO 22. In some embodiments, there is provided a method of treating an inflammatory disease (such as psoriasis) in an individual comprising administering to the indivudal an effective amount of a therapeutic agent comprising a peptide construct comprising (e.g., is) SEQ ID NO 26. In some embodiments, there is provided a method of treating an inflammatory disease (such as psoriasis) in an individual comprising administering to the indivudal an effective amount of a therapeutic agent comprising a peptide construct comprising (e.g., is) SEQ ID NO 28.

In some embodiments, there is provided a method of inhibiting inflammation in an individual, comprising administering to the indivudal an effective amount of a therapeutic agent comprising inhibitory peptide that interferes with the interaction between E1A and CtBP. In some embodiments, the inhibitory peptide comprises the sequence PX$_1$X$_2$X$_3$X$_4$ (SEQ ID NO:128), wherein X$_1$ is a hydrophobic residue, X$_2$ is a residue that preserves hydrogen bonding with CtBP, X$_3$ is a hydrophobic residue, and X$_4$ is a residue that preserves hydrogen bonding with CtBP. In some embodiments, the inhibitory peptide comprises the sequence PX$_1$X$_2$X$_3$X$_4$ (SEQ ID NO:129), wherein X$_1$ is L, V, I, M, Q, or E, X$_2$ is D or N, X$_3$ is L or I, and X$_4$ is S, C, T, V or A. In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of inhibiting inflammation in an individual, comprising administering to the indivudal an effective amount of a therapeutic agent comprising inhibitory peptide that interferes with the interaction between E1A and CtBP. In some embodiments, the inhibitory peptide comprises the sequence $PX_1DLS$ (SEQ ID NO:2), wherien $X_1$ is any amino acid. In some embodiments, the inhibitory peptide comprises the sequence PLDLS (SEQ ID NO:3). In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of inhibiting inflammation in an individual, comprising administering to the individual an effective amount of a therapeutic agent comprising inhibitory peptide that interferes with the interaction between E1A and CtBP. In some embodiments, the inhibitory peptide comprises the sequence $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:128), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:128), wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises $PX_1X_2X_3X_4$ (SEQ ID NO:129), wherein X1 is L, V, I, M, Q or E, $X_2$ is D or N, $X_3$ is L or I, and $X_4$ is 5, C, T, V or A, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:129), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:129), wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $N_1N_2N_3N_4PX_1X_2X_3X_4C_1C_2C_3C_4C_5$ (SEQ ID NO:130), wherein $N_1$ is E, G, P, A or V, $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $N_1N_2N_3N_4PX_1X_2X_3X_4C_1C_2C_3C_4C_5$ (SEQ ID NO:131), wherein $N_1$ is E, G, P, A or V, $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is 5, C, T, V or A, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence GGDGPLDLC-CRKRP (SEQ ID NO:133). In some embodiments, the inhibitory peptide comprises the sequence PTDEPLN-LSLKRPR (SEQ ID NO:134). In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of inhibiting inflammation in an individual, comprising administering to the indivudal an effective amount of a therapeutic agent comprising an inhibitory peptide that interferes with the interaction between E1A and CtBP, wherein the inhibitory peptide comprises the sequence $PX_1DLSX_2X_3$ (SEQ ID NO:4), wherien $X_1$ and $X_2$ are any amino acids, and $X_3$ is an amino acid having a bulky side chain. In some embodiments, the inhibitory peptide comprises the sequence $PX_1DLSX_2K$ (SEQ ID NO:6), wherien $X_1$ and $X_2$ are any amino acids. In some embodiments, the inhibitory peptide comprises the sequence $PLDLSX_1K$ (SEQ ID NO:10), wherein $X_1$ is any amino acid. In some embodiments, the inhibitory peptide comprises the sequence PLDLSCK (SEQ ID NO:12). In some embodiments, the inhibitory peptide comprises the sequence PLDLSCKRPR (SEQ ID NO:15). In some embodiments, the inhibitory peptide comprises (e.g., is) the sequence EPGQPLDLSCKRPR (SEQ ID NO:1). In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids).

In some embodiments, there is provided a method of inhibiting inflammation in an individual, comprising administering to the indivudal an effective amount of a therapeutic agent comprising a peptide construct comprising (e.g., is) SEQ ID NO: 20. In some embodiments, there is provided a method of inhibiting inflammation in an individual, comprising administering to the indivudal an effective amount of a therapeutic agent comprising a peptide construct comprising (e.g., is) SEQ ID NO: 22. In some embodiments, there is provided a method of inhibiting inflammation in an individual, comprising administering to the indivudal an effective amount of a therapeutic agent comprising a peptide construct comprising (e.g., is) SEQ ID NO: 26. In some embodiments, there is provided a method of inhibiting inflammation in an individual, comprising administering to the indivudal an effective amount of a therapeutic agent comprising a peptide construct comprising (e.g., is) SEQ ID NO:28.

In some embodiments, the inflammatory disease is selected from the group consisting of psoriasis, mucositis, chronic wound and trauma. In some embodiments, the inflammatory disease is selected from the group consisting of psoriatic arthritis, osteoarthritis, rheumatoid arthritis, and inflammatory bowel disease (e.g., Crohn's disease and ulcerative colitis), sepsis, atopic dermatitis, contact dermatitis, chronic obstructive pulmonary disease and chronic inflammatory pulmonary disease.

In some embodiments, the inflammatory disease is psoriasis. Psoriasis is a common inflammatory skin disease seen in dermatology clinics. The most frequently seen form of psoriasis is psoriasis vulgaris, occurring in 90% of all cases and characterized by scaly papulosquemous plaque lesions. Less common types of psoriasis, including psoriatic erythroderma, pustular psoriasis, and psoriatic arthritis, are usually thought to be more severe entities of psoriasis. Griffiths et al., 2007. *Lancet*, vol. 370: 263-271.

Thus, in some embodiments, there is provided a method of treating psoriasis (such as psoriasis volgaris) in an individual comprising administering to the indivudal an effective amount of a therapeutic agent comprising inhibitory peptide that interferes with the interaction between E1A and CtBP. In some embodiments, the inhibitory peptide comprises the sequence $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP. In some embodiments, the inhibitory peptide comprises the sequence $PX_1X_2X_3X_4$ (SEQ ID NO:129), wherein $X_1$ is L, V, I, M, Q, or E, $X_2$ is D or N, $X_3$ is L or I, and $X_4$ is S, C, T, V or A. In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids). In some embodiments, the therapeutic agent is administered topically.

Thus, in some embodiments, there is provided a method of treating psoriasis (such as psoriasis volgaris) in an individual comprising administering to the indivudal an effective amount of a therapeutic agent comprising inhibitory peptide that interferes with the interaction between E1A and CtBP. In some embodiments, the inhibitory peptide comprises the sequence $PX_1DLS$ (SEQ ID NO:2), wherien $X_1$ is any amino acid. In some embodiments, the inhibitory peptide comprises the sequence PLDLS (SEQ ID NO:3). In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids). In some embodiments, the therapeutic agent is administered topically.

In some embodiments, there is provided a method of treating psoriasis (such as psoriasis volgaris) in an individual comprising administering to the individual an effective amount of a therapeutic agent comprising an inhibitory peptide that interferes with the interaction between E1A and CtBP, wherein the inhibitory peptide comprises the sequence $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:128), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:128), wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises $PX_1X_2X_3X_4$ (SEQ ID NO:129), wherein X1 is L, V, I, M, Q or E, $X_2$ is D or N, $X_3$ is L or I, and $X_4$ is 5, C, T, V or A, and further comprises one of $N_4$, $N_3N_4$, $N_2N_3N_4$, or $N_1N_2N_3N_4$ (SEQ ID NO:164) at the N-terminus of $PX_1X_2X_3X_4$ (SEQ ID NO:129), wherein $N_1$ is E, G, P, A or V, $N_2$ is P, Q, G, S, T, V or M, $N_3$ is G, T, D, E or N, and $N_4$ is Q, V, E or G, and/or further comprises one of $C_1$, $C_1C_2$, $C_1C_2C_3$, $C_1C_2C_3C_4$ (SEQ ID NO:165), or $C_1C_2C_3C_4C_5$ (SEQ ID NO:166) at the C-terminus of $PX_1X_2X_3X_4$ (SEQ ID NO:129), wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $N_1N_2N_3N_4PX_1X_2X_3X_4C_1C_2C_3C_4C_5$ (SEQ ID NO:130), wherein $N_1$ is E, G, P, A or V, $N_2$ is P, Q, G, S, T, V or M, $N_3$ is G, T, D, E or N, and $N_4$ is Q, V, E or G, wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence $N_1N_2N_3N_4PX_1X_2X_3X_4C_1C_2C_3C_4C_5$ (SEQ ID NO:131), wherein $N_1$ is E, G, P, A or V, $N_2$ is P, Q, G, S, T, V or M, $N_3$ is G, T, D, E or N, and $N_4$ is Q, V, E or G, wherein $X_1$ is L, V, I, M, Q or E, $X_2$ is D or N, $X_3$ is L or I, and $X_4$ is 5, C, T, V or A, and wherein $C_1$ is C, M, L, K, V or T, $C_2$ is K, A or R, $C_3$ is R, T, H, P, K or C, $C_4$ is P, S, G, R or L, and $C_5$ is R, K, P, T, L or S. In some embodiments, the inhibitory peptide comprises the sequence EQTVPVDLS-VARPR (SEQ ID NO:132). In some embodiments, the inhibitory peptide comprises the sequence GGDGPLDLC-CRKRP (SEQ ID NO:133). In some embodiments, the inhibitory peptide comprises the sequence PTDEPLN-LSLKRPR (SEQ ID NO:134). In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids). In some embodiments, the therapeutic agent is administered topically.

In some embodiments, there is provided a method of treating psoriasis (such as psoriasis volgaris) in an individual comprising administering to the indivudal an effective amount of a therapeutic agent comprising an inhibitory peptide that interferes with the interaction between E1A and CtBP, wherein the inhibitory peptide comprises the sequence $PX_1DLSX_2X_3$ (SEQ ID NO:4), wherien $X_1$ and $X_2$ are any amino acids, and $X_3$ is an amino acid having a bulky side chain (such as R or K). In some embodiments, the inhibitory peptide comprises the sequence $PX_1DLSX_2K$ (SEQ ID NO:6), wherien $X_1$ and $X_2$ are any amino acids. In some embodiments, the inhibitory peptide comprises the sequence $PLDLSX_1K$ (SEQ ID NO:10), wherein $X_1$ is any amino acid. In some embodiments, the inhibitory peptide comprises the sequence PLDLSCK (SEQ ID NO:12). In some embodiments, the inhibitory peptide comprises the sequence PLDLSCKRPR (SEQ ID NO:15). In some embodiments, the inhibitory peptide comprises (e.g., is) the sequence EPGQPLDLSCKRPR (SEQ ID NO:1). In some embodiments, the therapeutic agent comprises a peptide construct comprising the inhibitory peptide and a cell penetration peptide. In some embodiments, the cell penetrating peptide is an amphipathic peptide. In some embodiments, the cell penetrating peptide is a cationic peptide. In some embodiments, the cell penetrating peptide is selected from the group consisting of Tat, Pep1, pAntp, Arg9, p1s1, and functionally equivalent variants thereof. In some embodiments, the cell penetration peptide comprises Tat. In some embodiments, the cell penetration peptide comprises Pep1. In some embodiments, the peptide construct is a fusion peptide, for example a fusion peptide that is no more than about 50 amino acids long. In some embodiments, the peptide construct may comprise a peptide linker (for example a peptide linker of less than about 5 amino acids, such as about 2 amino acids). In some embodiments, the therapeutic agent is administered topically.

In some embodiments, there is provided a method of treating psoriasis (such as psoriasis volgaris) in an individual comprising administering to the indivudal an effective amount of a therapeutic agent comprising a peptide construct comprising (e.g., is) SEQ ID NO 20. In some embodiments, there is provided a method of treating psoriasis (such as psoriasis volgaris) in an individual comprising administering to the indivudal an effective amount of a therapeutic agent comprising a peptide construct comprising (e.g., is) SEQ ID NO 22. In some embodiments, there is provided a method of treating psoriasis (such as psoriasis volgaris) in an individual comprising administering to the indivudal an effective amount of a therapeutic agent comprising a peptide construct comprising (e.g., is) SEQ ID NO 26. In some embodiments, there is provided a method of treating an inflammatory disease (such as psoriasis) in an individual comprising administering to the indivudal an effective amount of a therapeutic agent comprising a peptide construct comprising (e.g., is) SEQ ID NO 28. In some embodiments, the therapeutic agent is administered topically.

Methods of Administration and Dosage

The compounds described for use in the present invention can be administered to an individual via any route known in the art, including, but not limited to, those disclosed herein. The peptide constructs and/or conjugates of the present invention may be administered: intravenously, subcutaneously, topically, transdermally, intraperitoneally, orally, via intramuscular injection, intra-arterially, via inhalation (e.g. as mists or sprays), via nasal mucosa, gastrointestinally, and directly to a specific or affected organ. Topical administration is a preferred route of administration. The compounds described for use herein can be administered in the form of injectables, creams, solutions, emulsions, dispersions, suppositories, food premixes, tablets, pills, powder mixtures, capsules, granules, and in other suitable forms.

In some embodiments, the peptide constructs and/or conjugates may be formulated to extend their half-lives in vivo, such as by forming conjugates with a biocompatible polymer (e.g., polyethylene glycol (PEG)). In some embodiments, the peptide constructs and/or conjugates provided herein may be delivered using liposomes, microparticles, and nanoparticles for peptide drug delivery, as is known in the art. See, e.g., Tan, M. L. et al., 2010. Peptides, vol. 31: 184-193, incorporated herein in its entirety.

The amount of the peptide construct and/or conjugate administered to an individual in need thereof can be determined by various factors, such as the type of cancer, the biological and/or physiological response from the individual receiving the peptide therapeutic and other factors known to one of skill in the art. As such, the amount of the peptide construct and/or conjugate to be administered can be adjusted accordingly to achieve the desired beneficial effects. In one aspect, the amount of the peptide construct and/or conjugate to be used is at least about 1 µg peptide construct and/or conjugate/kg of the individual. In other aspects, the amount of the peptide construct and/or conjugate to be used is at least about 2 µg/kg, 3 µg/kg, 4 µg/kg, 5 µg/kg, 6 µg/kg, 7 µg/kg, 8 µg/kg, 9 µg/kg, 10 µg/kg, 11 µg/kg, 12 µg/kg, 13 µg/kg, 14 µg/kg, 15 µg/kg, 16 µg/kg, 17 µg/kg, 18 µg/kg, 19 µg/kg, 20 µg/kg, 21 µg/kg, 22 µg/kg, 23 µg/kg, 24 µg/kg, 25 µg/kg, 26 µg/kg, 27 µg/kg, 28 µg/kg, 29 µg/kg, or 30 µg/kg. In other aspects, the amount of the peptide construct and/or conjugate to be used is at least about 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg or 100 µg/kg. In other aspects, the amount of the peptide construct and/or conjugate to be used is about 1 µg/kg, 2 µg/kg, 3 µg/kg, 4 µg/kg, 5 µg/kg, 6 µg/kg, 7 µg/kg, 8 µg/kg, 9 µg/kg, 10 µg/kg, 11 µg/kg, 12 µg/kg, 13 µg/kg, 14 µg/kg, 15 µg/kg, 16 µg/kg, 17 µg/kg, 18 µg/kg, 19 µg/kg, 20 µg/kg, 21 µg/kg, 22 µg/kg, 23 µg/kg, 24 µg/kg, 25 µg/kg, 26 µg/kg, 27 µg/kg, 28 µg/kg, 29 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg or 100 µg peptide construct and/or conjugate/kg of the individual. In other aspects, the amount of the conjugate to be used is at most about 1 µg/kg, 2 µg/kg, 3 µg/kg, 4 µg/kg, 5 µg/kg, 6 µg/kg, 7 µg/kg, 8 µg/kg, 9 µg/kg, 10 µg/kg, 11 µg/kg, 12 µg/kg, 13 µg/kg, 14 µg/kg, 15 µg/kg, 16 µg/kg, 17 µg/kg, 18 µg/kg, 19 µg/kg, 20 µg/kg, 21 µg/kg, 22 µg/kg, 23 µg/kg, 24 µg/kg, 25 µg/kg, 26 µg/kg, 27 µg/kg, 28 µg/kg, 29 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg or 100 µg conjugate/kg of the individual. In other aspects, the invention provides for a dosage of range of any of the values given above. For example, the lower limit of the dosage range can be about 1 µg/kg, 2 µg/kg, 3 µg/kg, 4 µg/kg, 5 µg/kg, 6 µg/kg, 7 µg/kg, 8 µg/kg, 9 µg/kg, 10 µg/kg, 11 µg/kg, 12 µg/kg, 13 µg/kg, 14 µg/kg, 15 µg/kg, 16 µg/kg, 17 µg/kg, 18 µg/kg, 19 µg/kg, 20 µg/kg, 21 µg/kg, 22 µg/kg, 23 µg/kg, 24 µg/kg, 25 µg/kg, 26 µg/kg, 27 µg/kg, 28 µg/kg, 29 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg while the upper limit of the dosage range can be 2 µg/kg, 3 µg/kg, 4 µg/kg, 5 µg/kg, 6 µg/kg, 7 µg/kg, 8 µg/kg, 9 µg/kg, 10 µg/kg, 11 µg/kg, 12/µg/kg, 13 µg/kg, 14 µg/kg, 15 µg/kg, 16 µg/kg, 17 µg/kg, 18 µg/kg, 19 µg/kg, 20 µg/kg, 21 µg/kg, 22 µg/kg, 23 µg/kg, 24 µg/kg, 25 µg/kg, 26 µg/kg, 27 µg/kg, 28 µg/kg, 29 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg or 100 µg/kg.

Exemplary dosing frequencies for the administration of the peptide constructs include, but are not limited to, daily, every two days, every three days, every four days, every five days, every six days, weekly without break, weekly for three out of four weeks, once every three weeks, once every two weeks, or two out of three weeks. In some embodiments, the composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 14 days, 13 days, 12 days, 11 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

The amount of the peptide construct and/or conjugate administered to an individual in need thereof can be determined by various factors, such as the type of cancer, the biological and/or physiological response from the individual receiving the peptide therapeutic and other factors known to one of skill in the art. As such, the amount of the peptide construct and/or conjugate to be administered can be adjusted accordingly to achieve the desired beneficial effects. In one aspect, the amount of the peptide construct and/or conjugate to be used is at least about 1 µg peptide construct and/or conjugate/kg of the individual. In other aspects, the amount of the peptide construct and/or conjugate to be used is at least about 2 µg/kg, 3 µg/kg, 4 µg/kg, 5 µg/kg, 6 µg/kg, 7 µg/kg, 8 µg/kg, 9 µg/kg, 10 µg/kg, 11 µg/kg, 12 µg/kg, 13 µg/kg, 14 µg/kg, 15 µg/kg, 16 µg/kg, 17 µg/kg, 18 µg/kg, 19 µg/kg, 20 µg/kg, 21 µg/kg, 22 µg/kg, 23 µg/kg, 24 µg/kg, 25 µg/kg, 26 µg/kg, 27 µg/kg, 28 µg/kg, 29 µg/kg, or 30 µg/kg. In other aspects, the amount of the peptide construct and/or conjugate to be used is at least about 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg or 100 µg/kg. In other aspects, the amount of the peptide construct and/or conjugate to be used is about 1 µg/kg, 2 µg/kg, 3 µg/kg, 4 µg/kg, 5 µg/kg, 6 µg/kg, 7 µg/kg, 8 µg/kg, 9 µg/kg, 10 µg/kg, 11 µg/kg, 12 µg/kg, 13 µg/kg, 14 µg/kg, 15 µg/kg, 16 µg/kg, 17 µg/kg, 18 µg/kg, 19 µg/kg, 20 µg/kg, 21 µg/kg, 22 µg/kg, 23 µg/kg, 24 µg/kg, 25 µg/kg, 26 µg/kg, 27 µg/kg, 28 µg/kg, 29 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg or 100 µg peptide construct and/or conjugate/kg of the individual.

In other aspects, the amount of the conjugate to be used is at most about 1 µg/kg, 2 µg/kg, 3 µg/kg, 4 µg/kg, 5 µg/kg, 6 µg/kg, 7 µg/kg, 8 µg/kg, 9 µg/kg, 10 µg/kg, 11 µg/kg, 12 µg/kg, 13 µg/kg, 14 µg/kg, 15 µg/kg, 16 µg/kg, 17 µg/kg, 18 µg/kg, 19 µg/kg, 20 µg/kg, 21 µg/kg, 22 µg/kg, 23 µg/kg, 24 µg/kg, 25 µg/kg, 26 µg/kg, 27 µg/kg, 28 µg/kg, 29 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg or 100 µg conjugate/kg of the individual. In other aspects, the invention provides for a dosage of range of any of the values given above. For example, the lower limit of the dosage range can be about 1 µg/kg, 2 µg/kg, 3 µg/kg, 4 µg/kg, 5 µg/kg, 6 µg/kg, 7 µg/kg, 8 µg/kg, 9 µg/kg, 10 µg/kg, 11 µg/kg, 12 µg/kg, 13 µg/kg, 14 µg/kg, 15 µg/kg, 16 µg/kg, 17 µg/kg, 18 µg/kg, 19 µg/kg, 20 µg/kg, 21 µg/kg, 22 µg/kg, 23 µg/kg, 24 µg/kg, 25 µg/kg, 26 µg/kg, 27 µg/kg, 28 µg/kg, 29 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg while the upper limit of the dosage range can be 2 µg/kg, 3 µg/kg, 4 µg/kg, 5 µg/kg, 6 µg/kg, 7 µg/kg, 8 µg/kg, 9 µg/kg, 10 µg/kg, 11 µg/kg, 12 µg/kg, 13 µg/kg, 14 µg/kg, 15 µg/kg, 16 µg/kg, 17 µg/kg, 18 µg/kg, 19 µg/kg, 20 µg/kg, 21 µg/kg, 22 µg/kg, 23 µg/kg, 24 µg/kg, 25 µg/kg, 26 µg/kg, 27 µg/kg, 28 µg/kg, 29 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg or 100 µg/kg. Exemplary dosing frequencies for the administration of the peptide constructs include, but are not limited to, daily, every two days, every three days, every four days, every five days, every six days, weekly without break, weekly for three out of four weeks, once every three weeks, once every two weeks, or two out of three weeks. In some embodiments, the composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 14 days, 13 days, 12 days, 11 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

In some embodiments, the dosing frequency is once every two days for one time, two times, three times, four times, five times, six times, seven times, eight times, nine times, ten times, and eleven times. In some embodiments, the dosing frequency is once every two days for five times. The administration of the composition can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months. The dosing frequency of the composition may be adjusted over the course of the treatment based on the judgment of the administering physician.

Additional Exemplary Embodiments

The present application in some embodiments provides a peptide construct comprising a cell penetrating peptide and an inhibitory peptide that interferes with the interaction between E1A and CtBP.

In some embodiments according to (or as applied to) any of the embodiments above, the peptide construct is a fusion peptide.

In some embodiments according to (or as applied to) any of the embodiments above, the inhibitory peptide comprises $PX_1X_2X_3X_4$ (SEQ ID NO:128), wherein $X_1$ is a hydrophobic residue, $X_2$ is a residue that preserves hydrogen bonding with CtBP, $X_3$ is a hydrophobic residue, and $X_4$ is a residue that preserves hydrogen bonding with CtBP.

In some embodiments according to (or as applied to) any of the embodiments above, the inhibitory peptide comprises $PX_1X_2X_3X_4$ (SEQ ID NO:129), wherein $X_1$ is L, V, I, M, Q, or E, $X_2$ is D or N, $X_3$ is L or I, and $X_4$ is S, C, T, V or A.

In some embodiments according to (or as applied to) any of the embodiments above, the inhibitory peptide comprises $PX_1DLS$ (SEQ ID NO:2).

In some embodiments according to (or as applied to) any of the embodiments above, the inhibitory peptide comprises $PX_1DLSX_2K$ (SEQ ID NO:6).

In some embodiments according to (or as applied to) any of the embodiments above, inhibitory peptide comprises SEQ ID NO:1.

In some embodiments according to (or as applied to) any of the embodiments above, inhibitory peptide comprises SEQ ID NO:132.

In some embodiments according to (or as applied to) any of the embodiments above, inhibitory peptide comprises SEQ ID NO:133.

In some embodiments according to (or as applied to) any of the embodiments above, inhibitory peptide comprises SEQ ID NO:134.

In some embodiments according to (or as applied to) any of the embodiments above, the binding affinity of the inhibitory peptide to CtBP is the same or higher than that of SEQ ID NO:1.

In some embodiments according to (or as applied to) any of the embodiments above, the inhibitory peptide comprises no more than about 25 amino acids.

In some embodiments according to (or as applied to) any of the embodiments above, the inhibitory peptide comprises no more than about 15 amino acids.

In some embodiments according to (or as applied to) any of the embodiments above, the peptide construct comprises SEQ ID NO:127.

In some embodiments according to (or as applied to) any of the embodiments above, the peptide construct comprises SEQ ID NO:137.

In some embodiments according to (or as applied to) any of the embodiments above, the peptide construct is modified for conjugation to a carrier molecule.

In some embodiments according to (or as applied to) any of the embodiments above, the cell penetrating peptide is an amphipathic peptide or anionic peptide.

In some embodiments according to (or as applied to) any of the embodiments above, the cell penetrating peptide is a cationic peptide.

In some embodiments according to (or as applied to) any of the embodiments above, the cell penetrating peptide is selected from the group consisting of Tat, pAntp, Arg9, p1s1, and Pep1.

In some embodiments according to (or as applied to) any of the embodiments above, the cell penetrating peptide is directly fused to the inhibitory peptide.

In some embodiments according to (or as applied to) any of the embodiments above, the cell penetrating peptide is fused to the inhibitory peptide via a peptide linker.

In some embodiments according to (or as applied to) any of the embodiments above, the cell penetrating peptide is fused to the N-terminus of the inhibitory peptide.

In some embodiments according to (or as applied to) any of the embodiments above, the cell penetrating peptide is fused to the C-terminus of the inhibitory peptide.

The present application in some embodiments provides a pharmaceutical composition comprising a peptide construct described above.

The present application in some embodiments provides a conjugate comprising a peptide construct described above and a carrier molecule.

In some embodiments according to (or as applied to) any of the embodiments above, the carrier molecule is PEG.

The present application in some embodiments provides a pharmaceutical composition comprising a conjugate described above.

The present application in some embodiments provides a method of inhibiting cell proliferation in an individual comprising administering to the individual an effective amount of a pharmaceutical composition described above.

The present application in some embodiments provides a method of treating cancer in an individual comprising administering to the individual an effective amount of a pharmaceutical composition described above.

In some embodiments according to (or as applied to) any of the embodiments above, the cancer is cancer having a p53 mutation.

The present application in some embodiments provides a method of treating an inflammatory disease (such as psoriasis) in an individual comprising administering to the individual an effective amount of a pharmaceutical composition described above.

The present application in some embodiments provides a method of inhibiting inflammation in an individual comprising administering to the individual an effective amount of a pharmaceutical composition described above.

The present application in some embodiments provides a method of treating psoriasis (such as psoriasis volgaris) in an individual comprising administering to the individual an effective amount of a pharmaceutical composition described above.

In some embodiments according to (or as applied to) any of the embodiments above, the pharmaceutical composition is administered intravenously, intratumorally, subcutaneously, orally, and topically.

EXAMPLES

The invention is illustrated by the following examples which are not intended to be limiting in any way.

Example 1: CtBP is Overexpressed in Cancer

Methods and Materials

The ability of peptides to inhibit CtBP binding can be monitored by two biochemical assays. An AlphaScreen assay (Perkin-Elmer) was developed that is capable of detecting the CtBP-E1A interaction. Purified GST-E1A and 6xHis-CtBP are incubated with glutathione-conjugated donor beads and nickel-chelated acceptor beads respectively. The interaction between CtBP and E1A brings the donor and acceptor beads in close proximity, which produces a fluorescence signal after laser excitation and can be detected using the EnVision plate reader. A peptide that inhibits this interaction will limit the proximity of the beads and thus a loss in fluorescence signal will occur. In addition to the alphascreen, a fluorescence polarization based assay with a fluorescein-labeled 14mer E1A peptide (EPGQ-PLDLSCKRPR (SEQ ID NO: 1)) was also developed. Purified 6xHis-CtBP is incubated with the fluorescein-labeled E1A peptide and changes in the polarization value of the labeled peptide are detected using the EnVision plate reader. A decrease in peptide binding to CtBP can be detected by an increase in polarization, and used to monitor peptide inhibition. IC50 values of designed peptides can be determined using either of these assays through the addition of increasing amounts in each well and monitoring the degree of inhibition of the CtBP-E1A interaction.

Genome-wide mRNA expression changes in HNSCC cells upon CtBP knockdown were profiled. Fadu, a human HNSCC line, was purchased from ATCC and cultured in DMEM with 10% FBS. To knockdown CtBP, cells were treated with siRNA against human CtBP from Dharmacon using Lipofectamine 2000 (Invitrogen) for 48 hours, then harvested. Western blotting was performed using CtBP antibody (Millipore) to confirm the knockdown of CtBP. Total RNA was isolated using TRIzol (Invitrogen) as previously described (Zhang et al., 2006). mRNA was isolated using oligo-dT magnetic beads and sheared to 100-150 bp fragment. mRNA libraries were constructed following the Illumina RNA-seq protocol and sequenced on a GAIIx at the UC Denver Sequencing Facility. The differentially expressed genes were used for pathway enrichment analysis using NIH-DAVID and the KEGG pathway definitions (Huang da et al., 2009; Kanehisa et al., 2010).

All animal experiments were performed with the approval of IACUC at University of Colorado Denver.

Total RNA was isolated using TRIzol (Invitrogen) as previously described (Zhang et al., 2006). One hundred nanograms of RNA from each sample were subjected to qRT-PCR (ThermoFisher). An 18S probe was used as an internal control. Each sample was examined in triplicate. Relative RNA expression levels were determined by normalizing with internal controls, the values were calculated using the comparative Ct method.

Results

CtBP is overexpressed in multiple human cancers, starting at the hyperplasia stage. CtBP is an important regulator of embryonic development and its expression level is low or undetectable in many adult tissues (Furusawa et al., 1999; Deng et al., 2010; Hildebrand and Soriano, 2002). FIG. 1 shows that CtBP is re-expressed in a number of cancers, including lung and breast cancers. In invasive ductal breast cancer, positive nuclear CtBP staining was found in 92% of cases. In contrast, only 4% of normal breast tissue stained positive for CtBP (Deng et al., 2011). FIGS. 1A-C show that similar upregulation of CtBP was found in HNSCC (Head and Neck Squamous Cell Carcinoma), starting at the hyperplasia stage. Moreover, CtBP expression in human cancers transcriptionally represses the well-known tumor suppressors Brca 1 and E-cadherin (Deng et al., 2011; Deng et al., 2010), consistent with the metastatic characteristics initially identified for CtBP (Boyd et al., 1993). These data suggest CtBP1 is up-regulated early during cancer development and likely contributes to both cancer initiation and development. Furthermore, when CtBP was expressed in the non-transformed human mammary epithelial cells to mimic the CtBP overexpression found in human cancers, cell migration and resistance to radiation/chemo reagents were increased by CtBP expression (data not shown). Therefore, inhibition of CtBP may serve as a therapeutic approach for multiple cancer types.

Example 2: CtBP Knockdown is Sufficient to Suppress Tumorigenesis in Vivo

Figure 2:
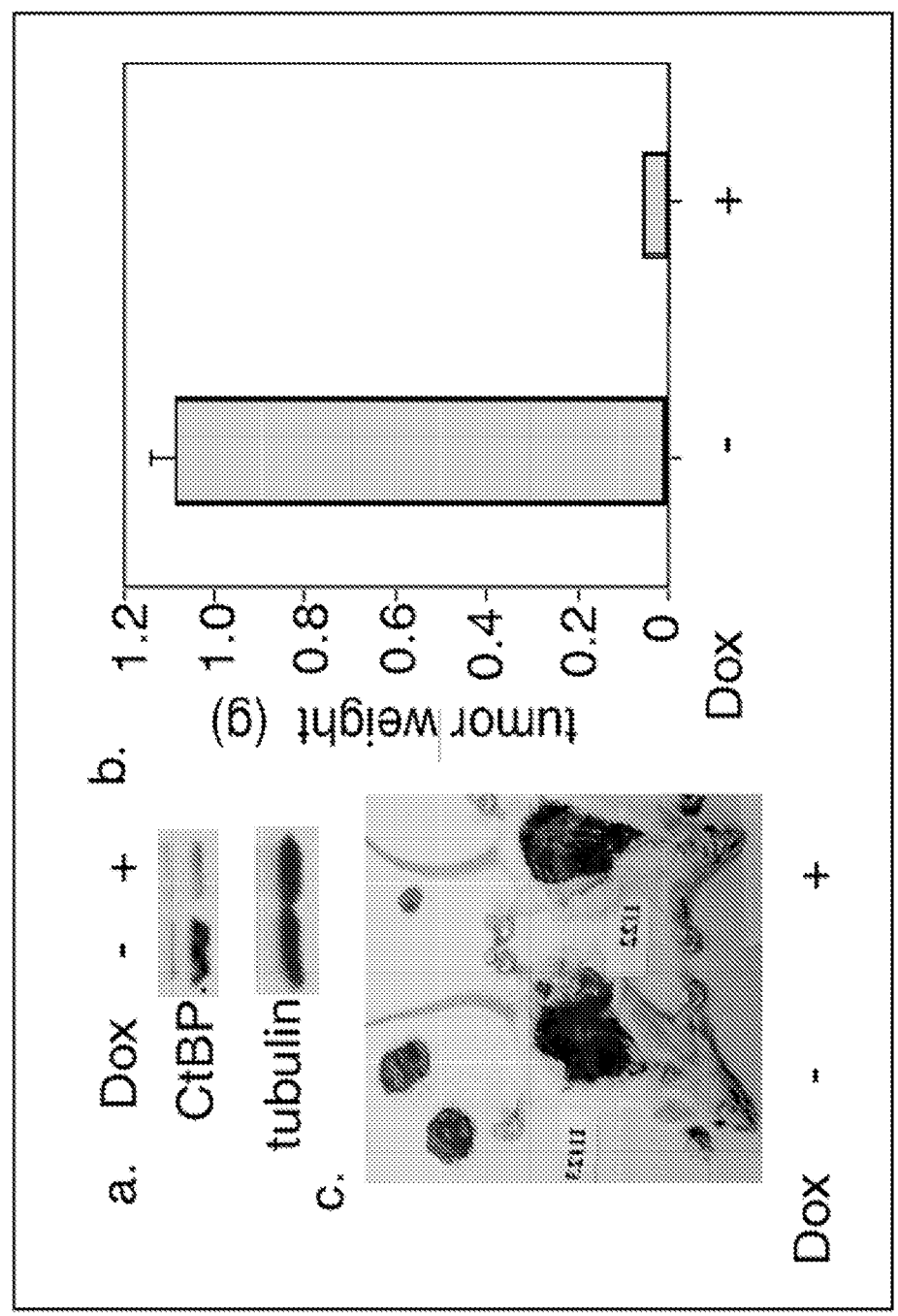
FIG. 2A-C shows the effect of CtBP knockdown on tumor growth.

Previous studies have shown that CtBP-null Ras-transformed cells are less tumorigenic (Grooteclaes et al., 2003), consistent with their increased sensitivity to pro-apoptotic stimuli. In order to directly evaluate the role of CtBP in human tumorigenesis in vivo, a tet-inducible siRNA targeting CtBP was constructed and stable clones were established in the human non-small cell carcinoma cell line H1299. Inclusion of Doxylcycline at 10 μg/mL in the tissue culture medium induced knockdown of CtBP proteins (FIG. 8) and triggered apoptosis (data not shown). Next, H1299 cells harboring the CtBP siRNA-expressing construct were inoculated to SCID mice subcutaneously. Briefly, $1 \times 10^6$ cells in 0.1 mL DMEM were injected in the left hind flanks of 6-month-old female CB17SC-RFM SCID mice. The mice were randomly divided into two groups of 10 mice per group. The treatment group received Doxylcycline (1 mg/mL in drinking water) right after tumor inoculation, whereas the control group received no treatment. Tumor diameters were measured every 5 days and tumors were weighed after necropsy. FIGS. 2B and 2C show that whereas sizable tumors developed in the control group, Doxylcycline-induced siRNA to CtBP dramatically reduced the tumor growth of H1299 xenografts. This data further supports inhibition of CtBP as a therapeutic approach for cancer therapy.

Example 3: Cell Penetrating Peptide (CPP)-E1A Functions as a CtBP Blocker

To further pursue novel drugs that inhibit CtBP-mediated pathological alterations, we designed peptide inhibitors (i.e., high-throughput screening was used to identify small molecule inhibitors) of the CtBP and E1A interaction. Such inhibitors should also inhibit the interaction between CtBP and its transcriptional partners because they share the same binding motif as E1A.

Figure 3:
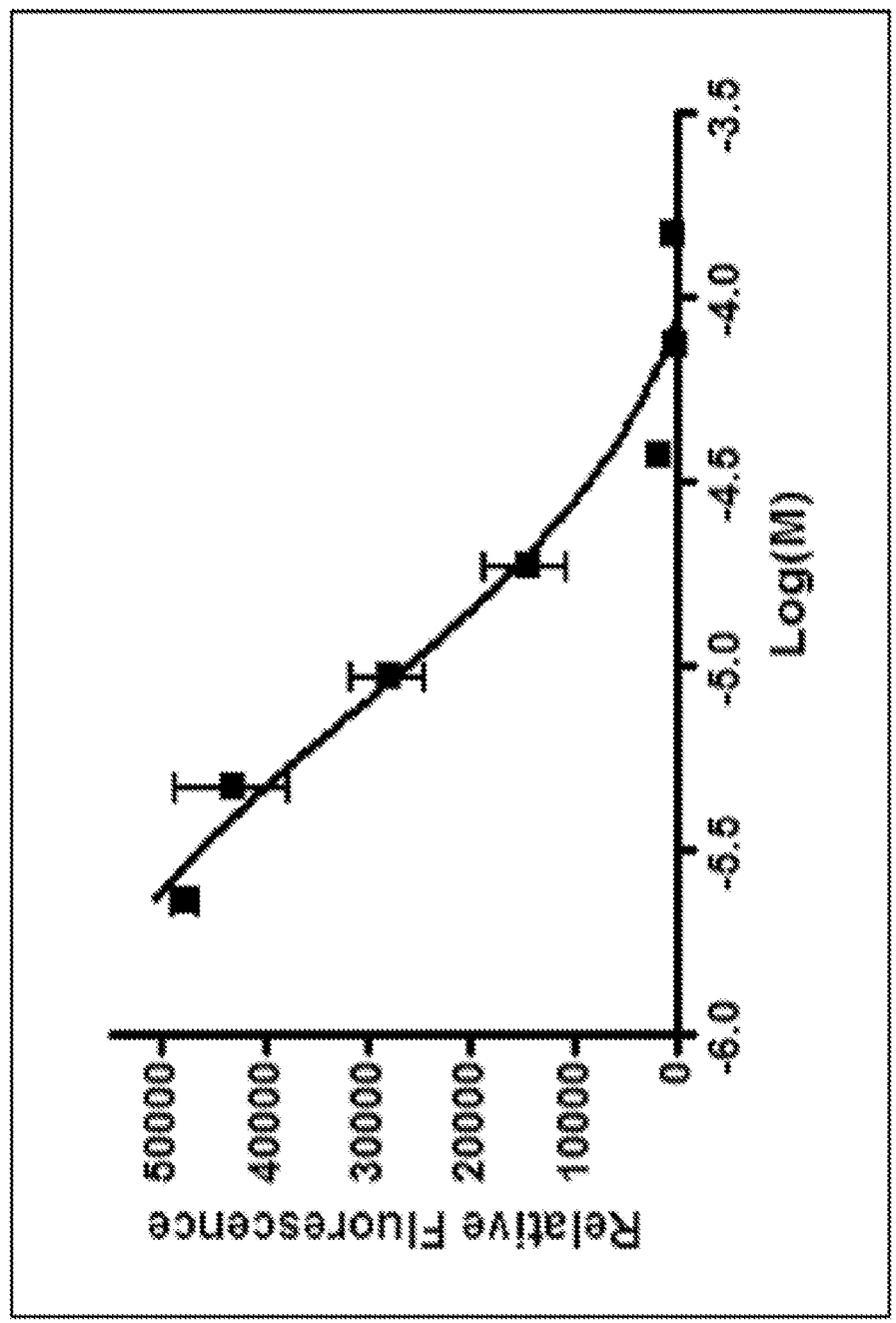
FIG. 3 shows a graph indicating that the Tat-E1A-flag peptide inhibits the CtBP/E1A interaction with an $IC_{50}$ of ~7.7 μM.
Figure 4:
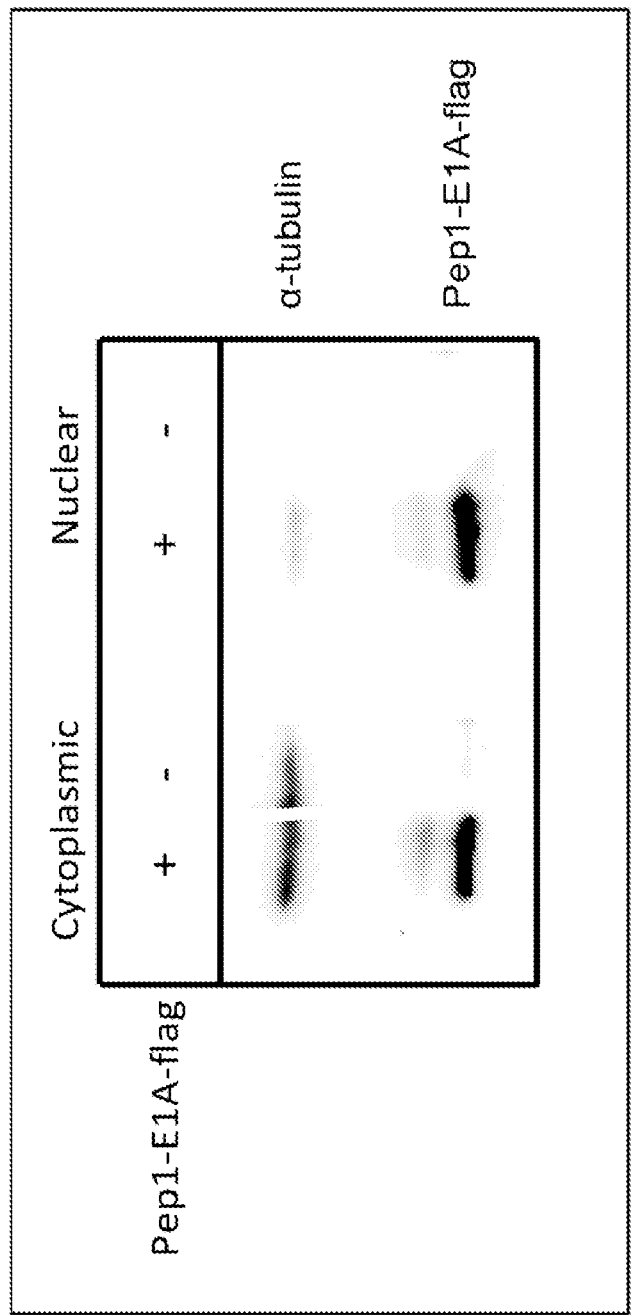
FIG. 4 shows a Western blot analysis of Pep1-E1A-flag treated cells revealing that Pep1-E1A-flag protein can enter the cytoplasm and the nucleus of H1299 cells. The same membrane was probed for α-tubulin, which is mainly localized in the cytoplasm.

The peptides Tat-E1A-flag (SEQ ID NO: 110) and Pep1-E1A-flag (SEQ ID NO: 113) were expressed and purified from *E. coli*. The purified Tat-E1A-flag peptide inhibited the CtBP/E1A interaction with an IC50 of ~7.7 µM, as shown in FIG. 3. H1299 cells were incubated with the Pep1-E1A-flag peptide (i.e., CPP-E1A-flag peptide), the cells were separated into cytoplasmic and nuclear fractions, and the presence of the CPP-E1A-flag peptide was probed using an anti-flag antibody in a Western blot. FIG. 4 shows an example of the Western blot of Pep1-E1A-flag treated cells, demonstrating that the CPP-E1A-flag peptide enters both the cytoplasm and the nucleus.

Figure 5:
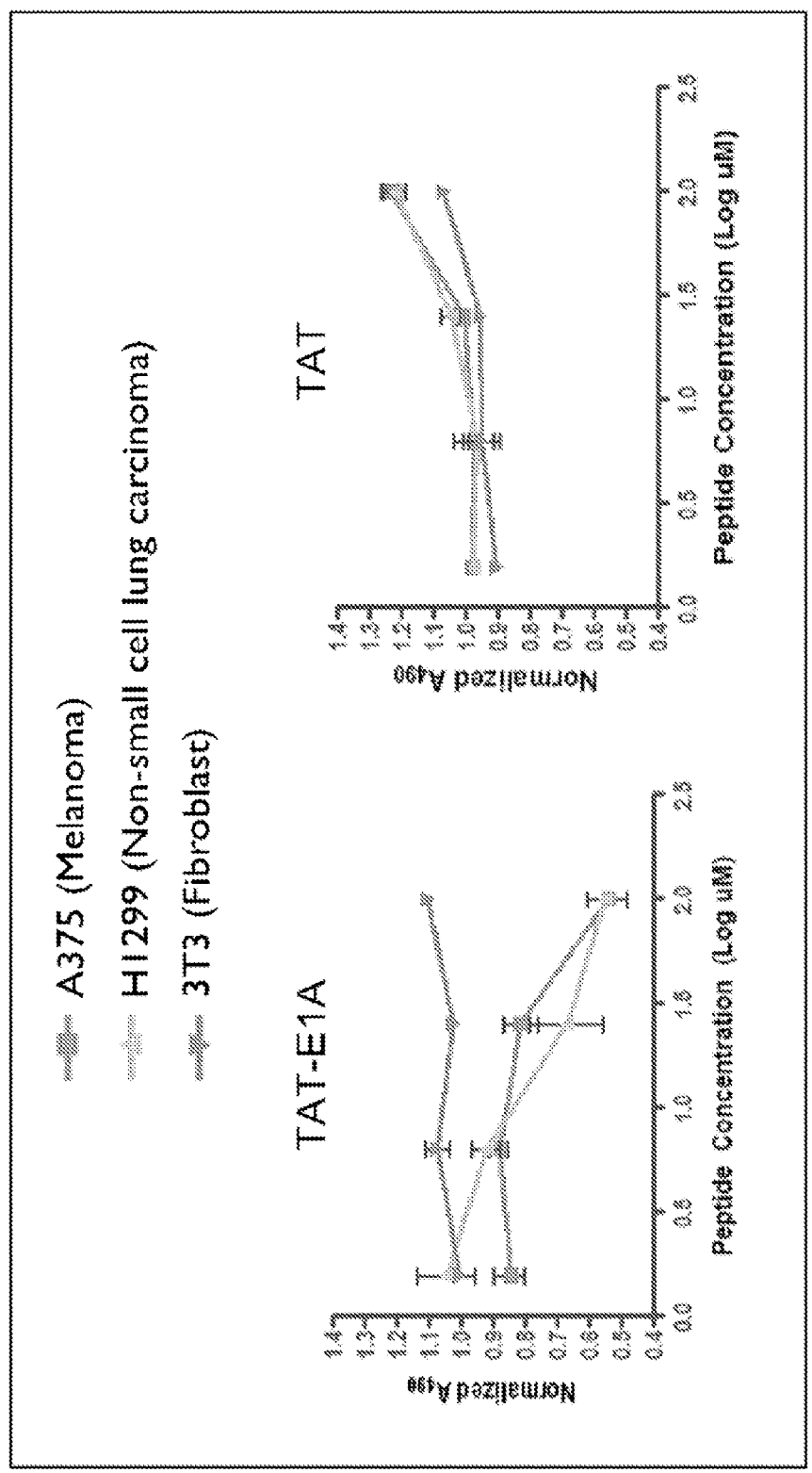
FIG. 5 shows a series of graphs revealing that the Tat-E1A peptide reduces the viability of CtBP overexpressing cancer cells A375 and H1299, but does not affect normal fibroblast 3T3 cells. Tat alone has no effect on these cells.

Next, the effect of Tat-E1A on cell viability using A375 derived from melanoma cells and H1299 derived from non-small cell lung carcinoma, both of which overexpress CtBP, as well as 3T3, which does not significantly overexpress CtBP, was examined. FIG. 5 shows that Tat-E1A reduces the viability of A375 and H1299 cells but does not affect 3T3 cells. The Tat peptide alone has no effect on these cells.

Figure 6:
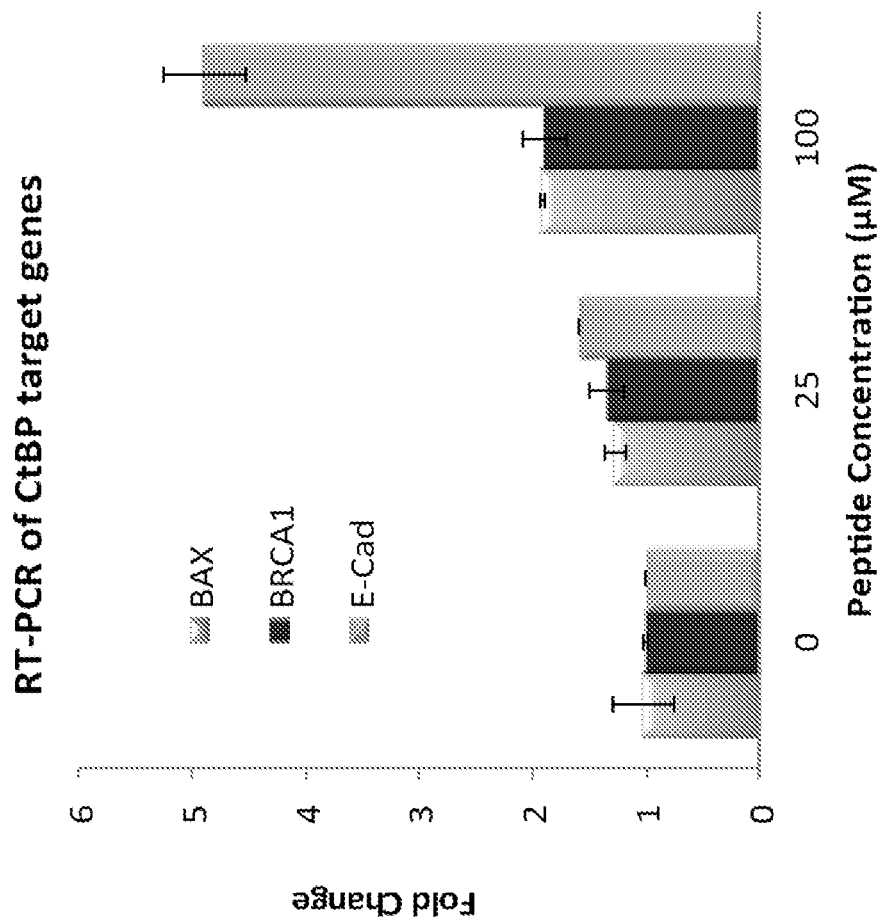
FIG. 6 shows a graph indicating that the Tat-E1A peptide relieves the suppression of CtBP target genes in H1299 cells.

Subsequently, the transcription levels of the endogenous CtBP target genes BAX, BRCA1, and E-Cadherin in Tat-E1A treated H1299 cells were evaluated using real-time PCR. As shown in FIG. 6, increasing concentrations of Tat-E1A peptide demonstrated a dose-dependent alleviation of CtBP-mediated suppression of these genes, suggesting that the Tat-E1A peptide inhibits the interaction between CtBP and these transcription factor partners.

Figure 7:
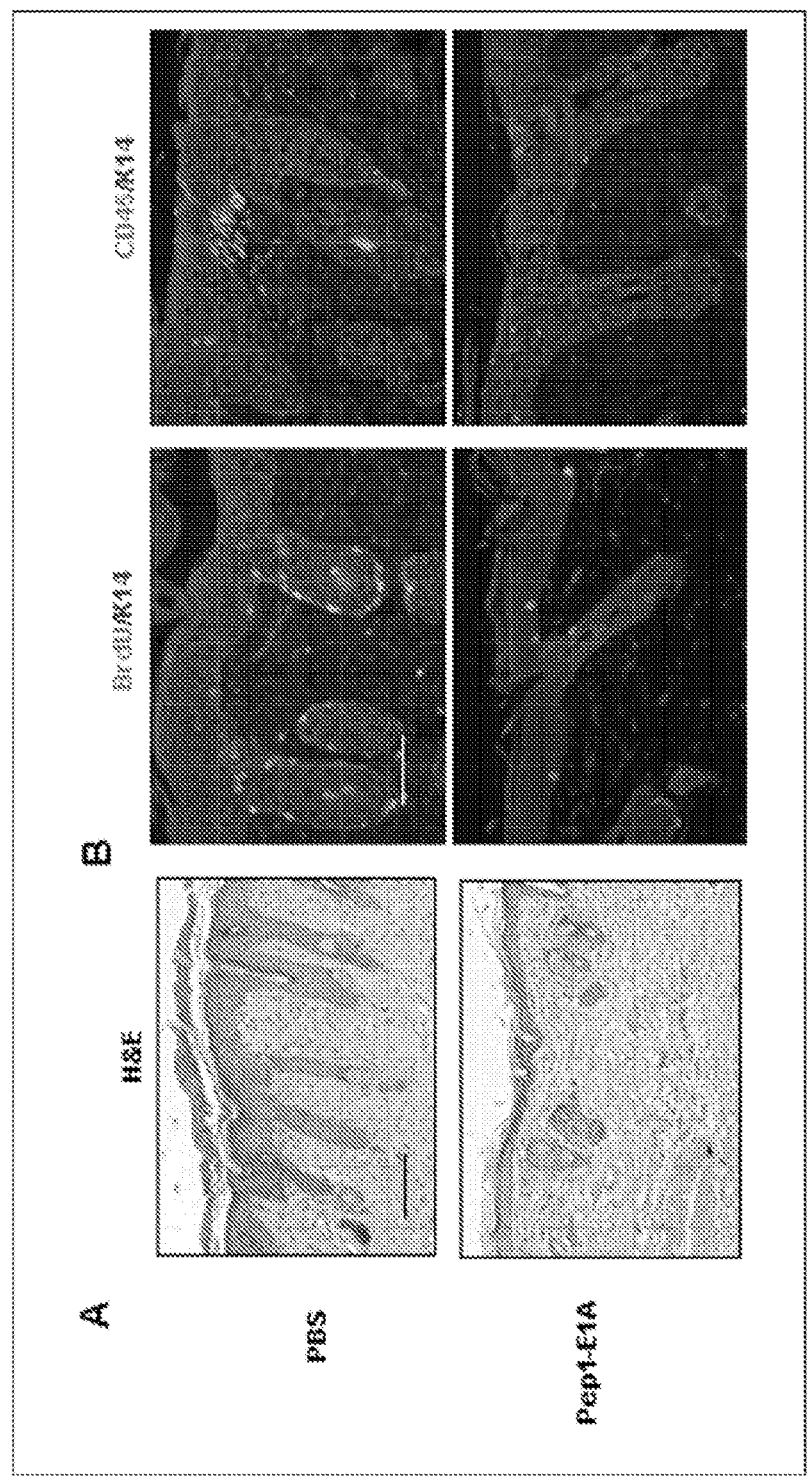
FIG. 7A-B shows the effect of Pep1-E1A on an IMQ-based psoriasis model.

Example 4: Pep1-E1A Reduces Proliferation and Inflammation in a Psoriasis Model To further evaluate the therapeutic effect of the CPP-E1A peptide, an IMQ-based psoriasis model was adopted and the efficacy of the CPP-E1A peptide was evaluated. Pep1-E1A treatment largely reduced the psoriasis-like phenotype when the Pep1-E1A peptide was either injected subcutaneously, as shown in FIG. 7, or applied on the skin (data not shown). The PBS-control group displayed inflamed scaly skin lesions resembling plaque type psoriasis following IMQ-induction. Mice treated with Pep1-E1A showed resistance to the IMQ-induction of psoriasis, as depicted in FIG. 7A.

To elucidate the molecular mechanisms for the Pep1-E1A blocker, H&E and immunostaining for proliferative and inflammatory markers was performed. As shown in FIG. 7B, Pep1-E1A treatment largely reduced the BrdU incorporation, suggesting that blocking CtBP1 decreases the overproliferation seen in psoriasis. FIG. 7B also shows that prominent inflammation, as revealed by CD45 staining and observed in IMQ-induced mice skin, was largely prevented by Pep1-E1A treatment. These data demonstrate that blocking CtBP1 function is effective in combating proliferating and inflammatory diseases.

Example 5: Phage Display Screening to Identify High Affinity CtBP Binding Peptides A short peptide (14 residues) with a desired random sequence is cloned into an M13KE gene III cloning vector of the Ph.D.™ Phage Display System (New England Biolabs). This cloning vector is a modified phage (M13) that can be propagated in bacteria to obtain a starting phage library with peptides displayed at the N-termini of gene II coat protein on phage surfaces. Purified CtBP is biotinylated following New England Biolab's standard biotinylation procedure, and immobilized onto petri dishes coated with streptavidin. The resulting phage library is incubated with CtBP and phages that do not bind are washed away.

Phages that bind CtBP are eluted, propagated, and subjected to one or more rounds of selection (i.e., another 3-5 rounds of selection). After the final round of selection, the gene encoding the peptide is sequenced to obtain the sequence of the peptide that binds tightly.

Multiple amino acid sequences may appear at positions outside the conserved peptide motif. The most frequently occurring amino acids in these positions are used to design the peptides that bind CtBP with the highest affinity. The affinity of these new peptides is compared to the original 14mer E1A peptide (SEQ ID NO:1) by comparing the IC50 of these peptides in inhibiting the CtBP/E1A protein interaction in a competition assay. The peptide identified from phage display that competes with the CtBP/E1A protein interaction better than the original 14mer E1A peptide is selected and conjugated to the cell penetrating peptide of the present invention. The peptides used in the assay described herein are provided in Table 3. Also provided in Table 3 are 1050 for selected peptides.

TABLE 3

| Peptide Name | SEQ ID NO: | Amino Acid Sequence | IC50 value (uM) |
|---|---|---|---|
| Wild-type | 1 | EPGQPLDLSCKRPR | 7.26 |
| K239Q | 19 | EPGQPLDLSCQRPR | 11.97 |
| K239A | 108 | EPGQPLDLSCARPR | 21.85 |
| K239-Acetylated | 109 | EPGQPLDLSC(Ac)KRPR | 26.62 |
| Tat-E1A fusion | 110 | GRKKRRQRRRPPQLEEPGQPLDLSCKRPRDYKDDDDK | 1.7 |
| Tat-E1A-Flag (LS-EL) | 111 | GRKKRRQRRRPPQLEEPGQPLDELCKRPRDYKDDDDK | >200 |
| Tat-E1A-Flag (K239Q) | 112 | GRKKRRQRRRPPQLEEPGQPLDLSCQRPRDYKDDDDK | 7.7 |
| Pep1-E1A-Flag | 113 | KETWWETWWTEWSQPKKKRKVLEEPGQPLDLSCKRPRDYKDDDDK | 26.62 |
| Pep1-E1A-Flag (LS-EL) | 114 | KETWWETWWTEWSQPKKKRKVLEEPGQPLDELCKRPRDYKDDDDK | |
| Pep1-E1A-Flag (K239Q) | 115 | KETWWETWWTEWSQPKKKRKVLEEPGQPLDELCQRPRDYKDDDDK | |
| Tat-E1A-Flag GSHM | 116 | GSHMGRKKRRQRRRPPQLEEPGQPLDLSCKRPRDYKDDDDK | |
| Tat-E1A-Flag (LS-EL) GSHM | 117 | GSHMGRKKRRQRRRPPQLEEPGQPLDELCKRPRDYKDDDDK | |
| Tat-E1A-Flag (K239Q) GSHM | 118 | GSHMGRKKRRQRRRPPQLEEPGQPLDLSCQRPRDYKDDDDK | |
| Pep1-E1A-Flag GSHM | 119 | GSHMKETWWETWWTEWSQPKKKRKVLEEPGQPLDLSCKRPRDYKDDDDK | |
| Pep1-E1A-Flag (LS-EL) GSHM | 120 | GSHMKETWWETWWTEWSQPKKKRKVLEEPGQPLDELCKRPRDYKDDDDK | |

TABLE 3-continued

| Peptide Name | SEQ ID NO: | Amino Acid Sequence | IC50 value (uM) |
|---|---|---|---|
| Pep1-E1A-Flag (K239Q) GSHM | 121 | GSHMKETWWETWWTEWSQP KKKRKVLEEPGQPLDELCQ RPRDYKDDDDK | |
| Pep1-E1A-Flag (K239Q) v.1 | 126 | KETWWETWWTEWSQPKKKR KVLEEPGQPLDLSCQRPRD YKDDDDK | |
| Pep1-E1A-Flag (K239Q) GSHM v.1 | 127 | GSHMKETWWETWWTEWSQP KKKRKVLEEPGQPLDLSCQ RPRDYKDDDDK | |

Example 6: Use of mRNA Display Technology to Identify Cell-Penetrating Peptides Specific to Cancer A DNA library encoding random peptides is in vitro transcribed and linked to puromycin through a DNA linker, which enables the generation of an mRNA-puromycin-peptide fusion upon in vitro translation. This mRNA-peptide fusion is incubated with specific cell lines (e.g., non-small cell lung cancer cell lineH1299, breast cancer cell line MCf 7, melanoma cell line A375, colon cancer cell line IIT-29, or others), extensively washed, and cell-penetrating peptides are recovered through RT-PCR and sequencing of the mRNAs. Rounds of selection generate cell penetrating peptides that enter cells with high efficiency. Cell-penetrating peptides are screened as described in Kondo et al. (2012) *Nat Commun.* 3: 951.

Example 7: Peptide Assay for 1050 Binding

The ability of peptides to inhibit CtBP binding can be monitored by two biochemical assays. An AlphaScreen assay (Perkin-Elmer) was developed that is capable of detecting the CtBP-E1A interaction. Purified GST-E1A and 6xHis-CtBP are incubated with glutathione-conjugated donor beads and nickel-chelated acceptor beads respectively. The interaction between CtBP and E1A brings the donor and acceptor beads in close proximity, which produces a fluorescence signal after laser excitation and can be detected using the EnVision plate reader. A peptide that inhibits this interaction will limit the proximity of the beads and thus a loss in fluorescence signal will occur. In addition to the alphascreen, a fluorescence polarization based assay with a fluorescein-labeled 14mer E1A peptide (EPGQ-PLDLSCKRPR (SEQ ID NO: 1)) was also developed. Purified 6xHis-CtBP is incubated with the fluorescein-labeled E1A peptide and changes in the polarization value of the labeled peptide are detected using the EnVision plate reader. A decrease in peptide binding to CtBP can be detected by an increase in polarization, and used to monitor peptide inhibition. IC50 values of designed peptides can be determined using either of these assays through the addition of increasing amounts in each well and monitoring the degree of inhibition of the CtBP-E1A interaction. The peptides used in the assay described herein are provided in Table 4. Also provided in Table 4 are IC50 for selected peptides.

TABLE 4

| Peptide Name | SEQ ID NO: | Amino Acid Sequence | IC50 value (uM) |
|---|---|---|---|
| Wild-type | 1 | EPGQPLDLSCKRPR | 7.26 |
| K239Q | 19 | EPGQPLDLSCQRPR | 11.97 |
| K239A | 108 | EPGQPLDLSCARPR | 21.85 |
| K239-Acetylated | 109 | EPGQPLDLSC(Ac)KRPR | 26.62 |
| Tat-E1A fusion | 110 | GRKKRRQRRRPPQLEEPGQ PLDLSCKRPRDYKDDDDK | 1.7 |
| Tat-E1A Flag (LS-EL) | 111 | GRKKRRQRRRPPQLEEPGQ PLDELCKRPRDYKDDDDK | >200 |
| Tat-E1A Flag (K239Q) | 112 | GRKKRRQRRRPPQLEEPGQ PLDLSCQRPRDYKDDDDK | 7.7 |
| Pep1-E1A-Flag | 113 | KETWWETWWTEWSQPKKKR KVLEEPGQPLDLSCKRPRD YKDDDDK | 26.62 |
| Pep1-E1A-Flag (LS-EL) | 114 | KETWWETWWTEWSQPKKKR KVLEEPGQPLDELCKRPRD YKDDDDK | |
| Pep1-E1A-Flag (K239Q) | 115 | KETWWETWWTEWSQPKKKR KVLEEPGQPLDELCQRPRD YKDDDDK | |
| Tat-E1A Flag GSHM | 116 | GSHMGRKKRRQRRRPPQLE EPGQPLDLSCKRPRDYKDD DDK | |
| Tat-E1A Flag (LS-EL) GSHM | 117 | GSHMGRKKRRQRRRPPQLE EPGQPLDELCKRPRDYKDD DDK | |
| Tat-E1A Flag (K239Q) GSHM | 118 | GSHMGRKKRRQRRRPPQLE EPGQPLDLSCQRPRDYKDD DDK | |
| Pep1-E1A-Flag GSHM | 119 | GSHMKETWWETWWTEWSQP KKKRKVLEEPGQPLDLSCK RPRDYKDDDDK | |
| Pep1-E1A-Flag (LS-EL) GSHM | 120 | GSHMKETWWETWWTEWSQP KKKRKVLEEPGQPLDELCK RPRDYKDDDDK | |
| Pep1-E1A-Flag (K239Q) GSHM | 121 | GSHMKETWWETWWTEWSQP KKKRKVLEEPGQPLDELCQ RPRDYKDDDDK | |
| Pep1-E1A-Flag (K239Q) v.1 | 126 | KETWWETWWTEWSQPKKKR KVLEEPGQPLDLSCQRPRD YKDDDDK | |
| Pep1-E1A-Flag (K239Q) GSHM v.1 | 127 | GSHMKETWWETWWTEWSQP KKKRKVLEEPGQPLDLSCQ RPRDYKDDDDK | |

Additional peptides were tested for in vitro inhibitory potency (Table 5). For Kd determination, FITC-labeled peptide (FITC-peptide) was incubated with varying concentrations of CtBP. The fluorescence polarization values of the FITC-peptide were measured and plotted against CtBP concentration to determine Kd of the FITC-peptide with CtBP using the Prism program. The peptide EQTVPVDLSVARPR (SEQ ID NO:132) demonstrated an improved Kd of 2.2 µM as compared to the peptide EPGQPLDLSCKRPR (SEQ ID NO:1) which had a Kd of 4.3 µM (Table 5). For IC50 determination, a fluorescence polarization assay was utilized. A FITC-labeled 14mer peptide was incubated with CtBP which produced relatively high fluorescence polarization values. Increasing concentrations of unlabeled peptide were added to compete with the FITC-labeled peptide, leading to a decreased fluorescence polarization value. An IC50 was calculated to represent the concentration of the unlabeled peptide that resulted in 50% reduction of the fluorescence polarization value. The peptide EPGQPLSLSCKRPR (SEQ ID NO:135) did not inhibit CtBP even though it only differed from the peptide EPGQPLDLSCKRPR (SEQ ID NO:1) at one residue in the middle of the recognition motif. The peptide PTDEPLNLSLKRPR (SEQ ID NO:134) demonstrated an improved IC50 of 4.4 µM as compared to the peptide EPGQPLDLSCKRPR (SEQ ID NO:1) which had an IC50 of 6.0 µM (Table 5).

TABLE 5

Peptides tested for in vitro inhibitory potency

| SEQ ID NO: | Peptide sequence | IC50 (µM) | Kd (µM) |
|---|---|---|---|
| 1 | EPGQ PLDLS CKRPR | 6.0 | 4.3 |
| 132 | EQTV PVDLS VARPR |  | 2.2 |
| 133 | GGDG PLDLC CRKRP | 18.8 |  |
| 134 | PTDE PLNLS LKRPR | 4.4 |  |
| 135 | EPGQ PLSLS CKRPR | no inhibition |  |

Example 8: CtBP1 Transactivates TGF-β

Methods and Materials
mRNA-seq

Genome-wide mRNA expression changes in HNSCC cells upon CtBP1 knockdown were profiled. Fadu, a human HNSCC line, was purchased from ATCC and cultured in DMEM with 10% FBS. To knockdown CtBP1, cells were treated with siRNA against human CtBP1 from Dharmacon using Lipofectamine 2000 (Invitrogen) for 48 hours, then harvested. Western blotting was performed using CtBP1 antibody (Millipore) to confirm the knockdown of CtBP1. Total RNA was isolated using TRIzol (Invitrogen) as previously described (Zhang et al., 2006). mRNA was isolated using oligo-dT magnetic beads and sheared to 100-150 bp fragment. mRNA libraries were constructed following the Illumina RNA-seq protocol and sequenced on a GAIIx at the UC Denver Sequencing Facility. The differentially expressed genes were used for pathway enrichment analysis using NIH-DAVID and the KEGG pathway definitions (Huang da et al., 2009; Kanehisa et al., 2010).

Generation and Identification of K5.CtBP1 Mice

All animal experiments were performed with the approval of IACUC at University of Colorado Denver. The ~1.4 kb full-length wild-type human CtBP1 cDNA was inserted into the K5 expression vector (He et al., 2002). The K5.CtBP1 transgenic mice were generated with the B6D2 strain by microinjection of the transgene into the pronuclei of mouse embryos. Mice were genotyped by PCR analysis of tail DNA utilizing primers specific for BK5 (tctgataggcagcctg-cacc (SEQ ID NO: 167)) and CtBP1 (atcccagctgctgtggaagg (SEQ ID NO: 168)). Throughout this study, all transgenic mice were heterozygous; all wild type mice were littermates, and at least three independent analyses were performed for each assay, using three to five samples in each group.

Human Samples

Psoriasis and case-matched normal skin tissue samples were surgically resected between the years 2007 and 2009 from consenting patients at the Department of Dermatology, University of Colorado Denver under an Institutional Review Board approved protocol. Human skin biopsy specimens were taken from lesions of patients with chronic plaque-type psoriasis and normal skin of healthy donors.

Tissue Histology, Immunofluorescence, and Immunohistochemistry

Skin histology was visualized with hematoxylin and eosin (H&E) staining Immunofluorescence and immunohistochemistry were performed on frozen and paraffin-embedded sections as previously described (Wang et al., 1999) Immunofluorescence was performed using antibodies against CD45, CD4, CD31 (BD Biosciences); Ly-6G (eBioscience); F4/80 (Caltag Laboratories); ALK1 (R&D Systems); pSmad2 (Cell Signaling); and Keratin 14 (Fitzgerald). The antibodies used in immunohistochemistry included CtBP1 (Millipore), and TGF-β1 (R&D Systems). Biotinylated secondary antibodies were used in conjunction with an avidin-peroxidase reagent (VECTASTAIN®) and visualized using diaminobenzidine (Sigma).

qRT-PCR

Total RNA was isolated using TRIzol (Invitrogen) as previously described (Zhang et al., 2006). One hundred nanograms of RNA from each sample were subjected to qRT-PCR (ThermoFisher). An 18S probe was used as an internal control. Each sample was examined in triplicate. Relative RNA expression levels were determined by normalizing with internal controls, the values were calculated using the comparative Ct method.

In Vivo Knockdown by Delivery siRNA to Mouse Skin

A biodegradable polymer PEI F25-LMW (polyethylenimines, F25 low molecular weight, Sigma) was used as a delivery vehicle, preventing degradation and increasing cellular uptake of siRNA in vivo without noticeable toxicity (Hobel et al., 2010). TGF-β1 siRNA from Dharmacon mixed with PEI F25-LMW was injected into K5.CtBP1 skin twice/week for 3 weeks.

Cell Culture and Transfections

Fadu, a human HNSCC line, was purchased from ATCC and cultured in DMEM with 10% FBS. To knockdown CtBP1, cells were treated with siRNA against human CtBP1 from Dharmacon using Lipofectamine 2000 (Invitrogen) for 48 hours, and harvested. Western blotting was performed as previously described (Zhang et al., 2003).

Chromatin Immunoprecipitation (ChIP) and Luciferase Reporter Assay

Figure 8:
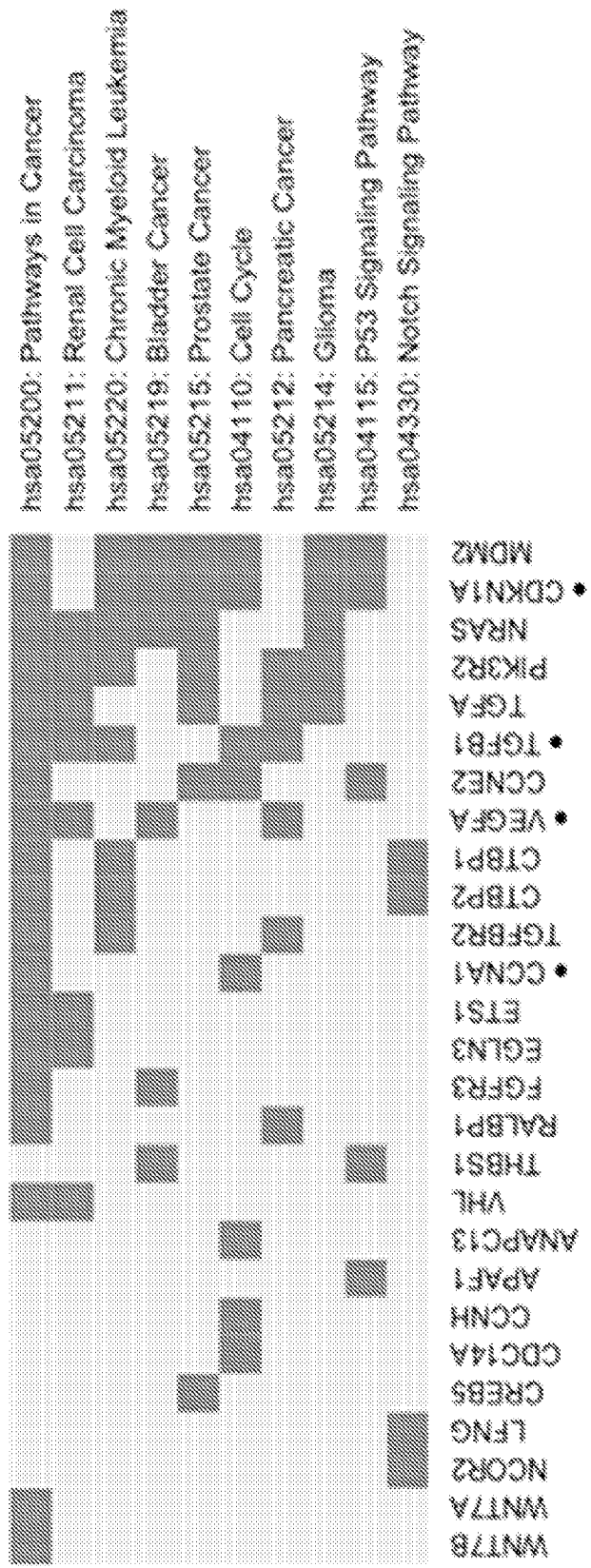
FIG. 8 shows a graph revealing that CtBP1 knockdown downregulates the TGF-β1 signaling pathway. Dark grey blocks represent the presence of CtBP target genes in the indicated pathways; components of the TGF-β1 pathway are indicated with a bullet point.

Fadu cells were used for ChIP assay with an anti-CtBP1 antibody and normal rabbit IgG as described previously (Zhang et al., 2006). Sequential ChIPs were carried out using an anti-CtBP1 antibody following the first ChIP with an anti-c-Jun antibody (Abcam) or an anti-Sp1 antibody (Santa Cruz) (Deng et al., 2010; Hoot et al., 2010). Primer sets spanning the TGF-β1 promoter were used to q-PCR-amplify the ChIP sample. The pGL4.26 TGF-β1 promoter luciferase reporter plasmid was generated by cloning a PCR-amplified 633 bp fragment of the TGF-β1 promoter into the KpnI and BglII sites of pGL4.26 vector (Promega). TGF-β1 promoter-specific primers used were 5'-ggggtac-cACCTTGTTTCC-3' (forward, -strand, SEQ ID NO: 169) and 5'-gaagatctCTCCTCCCCGC-3' (reverse, +strand, SEQ ID NO: 170). Site-directed mutagenesis was performed to generate the mutation at the distal AP-1 site (mt1: TGACTCT to TGgtTCT), the proximal AP-1 site (mt2: TGTCTCA to gtTCTCA), or the SP1 site (mt3: GCCCGCC to GCCtaCC). An empty renilla luciferase vector (pGL4.79) was used for normalization. Fadu cells were co-transfected with the reporters and siRNA to CtBP1 for 48 hr and luciferase activity was measured (Zhang et al., 2002). Scrambled siRNA or empty plasmid was used for controls.
Results Genome-wide mRNA-seq analysis was performed in Fadu cells with and without CtBP1 knockdown. Upon CtBP1 knockdown, 102 genes were up-regulated while 200 genes were down-regulated with a two fold cutoff. Genes with significant changes were used for pathway enrichment analysis using NIH-DAVID (Huang da et al., 2009) and the KEGG pathway definitions (Kanehisa et al., 2010). The TGF-β1 signaling pathway was identified in the signaling pathways highly regulated by CtBP1, as shown in FIG. 8. In contrast to the conventional transcriptional repressive role of CtBP1, FIG. 10A shows that TGF-β1 and the canonical mediators for TGF-β1 signaling were up-regulated by CtBP1, and thus abrogated by CtBP1 knockdown.

Consistent with mRNA changes observed during CtBP1 knockdown, the luciferase activity of the TGF-β1 promoter decreased by 60% with CtBP1 siRNA (FIG. 10B), suggesting that CtBP1 regulates TGF-β1 transcription via its promoter. As a central mediator for cell growth, inflammation, and angiogenesis, transcriptional regulation of TGF-β1 has attracted intensive study and the regulatory sites at its promoter are well characterized. We asked if CtBP1 could form an active transcription complex at the TGF-β1 promoter via the previously identified AP-1 sites and the Sp1 site, which are critical for TGF-β1 activation (Kim et al., 1989; Weigert et al., 2000). To determine if these cis-elements mediate TGF-β1 activation by CtBP1, the AP-1 sites and Sp1 site were individually mutated. As shown in FIG. 10B, the mutation at the proximal AP-1 site or the Sp1 site did not affect the TGF-β1 promoter-driven luciferase reporter activity, but the mutation in the distal AP-1 site attenuated the TGF-β1 promoter-driven luciferase reporter activity. FIG. 10B shows that the expression level of the TGF-β1 promoter-driven luciferase reporter with the mutated distal AP-1 site is similar to the expression level of the wild type promoter-driven luciferase reporter with the CtBP1 knockdown in Fadu cells, suggesting that CtBP1 regulates TGF-β1 through the distal AP-1 site.

To determine whether CtBP1 plays a direct role in the regulation of TGF-β1 gene, chromatin immunoprecipitation (ChIP) was performed to see if CtBP1 is recruited to the TGF-β1 promoter. As shown in the top panel of FIG. 10C, immunoprecipitation of the cross-linked chromatin with the antibody specific for CtBP1 revealed that CtBP1 bound the TGF-β1 promoter in Fadu cells. Furthermore, sequential ChIP using an anti-c-Jun antibody and then an anti-CtBP1 antibody revealed that CtBP1 binds to the TGF-β1 promoter through c-Jun (FIG. 10C, bottom panel). This finding supports participation of the AP-1 site in CtBP1-mediated activation. In contrast, the middle panel of FIG. 10C shows that no CtBP1 binding to the TGF-β1 promoter via Sp1 was observed using sequential ChIP with an anti-Sp1 antibody, followed by an anti-CtBP1 antibody.

Figure 11:
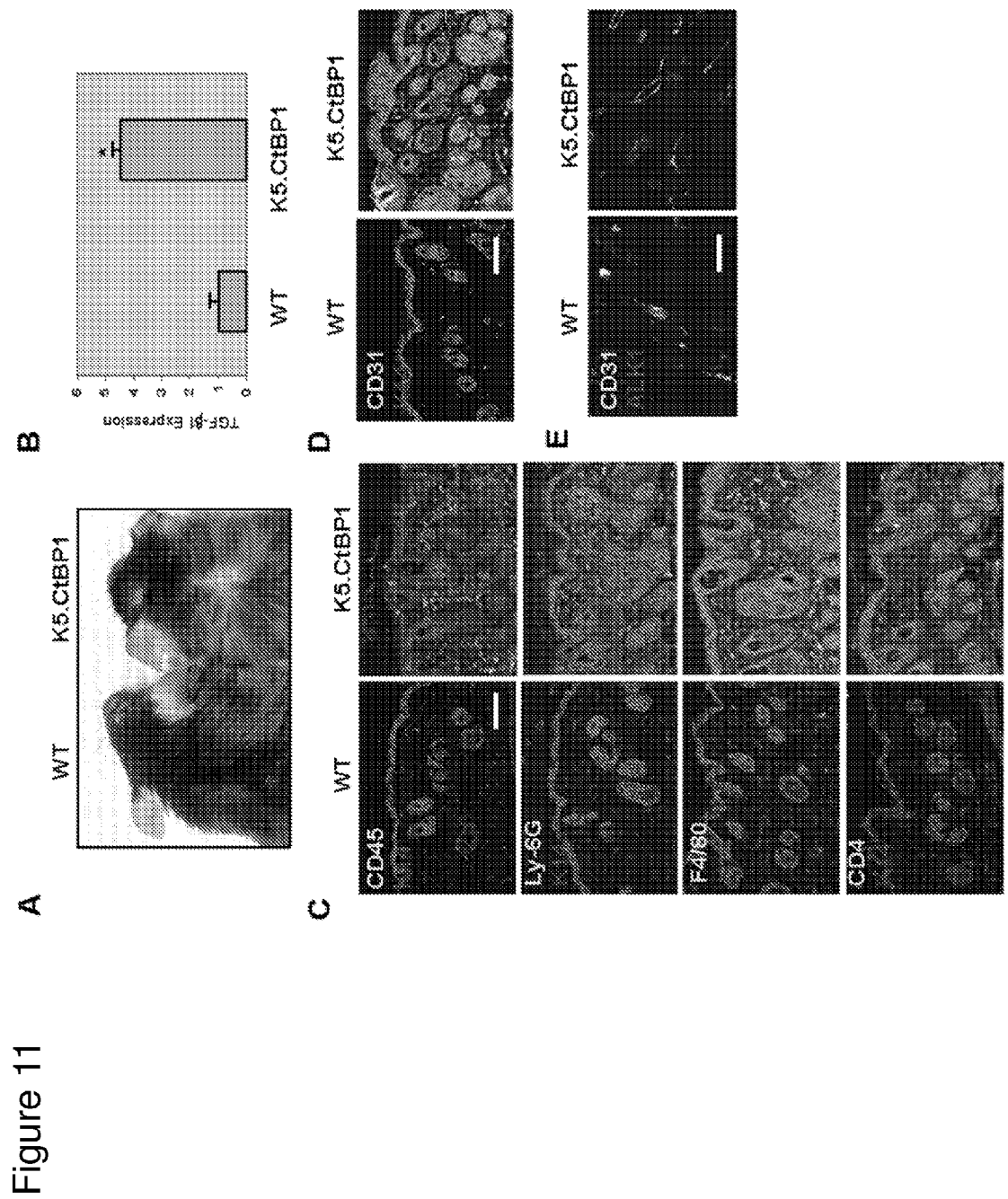
FIG. 11A-E shows increased inflammation and angiogenesis in K5.CtBP1 transgenic skin.

Example 9: CtBP1 Overexpression Causes Inflammation and Increases Angiogenesis Associated with Enhanced TGF-β1 Signaling Both CtBP1 and TGF-β1 are expressed at very low levels in most adult tissue, making it difficult to use CtBP1 knockout mice to assess whether CtBP1 mediated TGF-β1 activation has functional consequences. Therefore, K5.CtBP1 transgenic mice were generated by inserting human CtBP1 cDNA (99% amino acid homology to mouse CtBP1 protein) into a K5 vector (He et al., 2002). When CtBP1 transgene expression levels were 3-fold higher than endogenous CtBP1 levels in skin (FIG. 12B), K5.CtBP1 mice displayed an inflammatory phenotype (FIG. 11A). Consistent with the results from the genome-wide expression analysis and cell based assays, TGF-β1 mRNA was found to be up-regulated by the CtBP1 transgene in mouse skin, as shown in FIG. 11B. Histopathology shows that K5.CtBP1 skin contains numerous infiltrated leukocytes and increased vessel numbers (data not shown). Therefore, tissue sections were stained with CD45 antibody, confirming the presence of leukocytes in transgenic epidermis and dermis but very few in wild type skin (FIG. 11C). To further identify infiltrating leukocyte subtypes in CtBP1-transgenic skin, antibodies specific for leukocyte subtype markers were used. K5.CtBP1-transgenic epidermis and dermis contained Ly-6G positive granulocytes, as shown in FIG. 11C Staining with an F4/80 antibody showed that K5.CtBP1 dermis contained macrophages and CD4$^+$ T cells were present in K5.CtBP1 dermis (FIG. 11C).

K5.CtBP1 transgenic skin also exhibited increased angiogenesis, confirmed by immunofluorescence staining with the endothelial marker CD31, as shown in FIG. 11D. Furthermore, the endothelial-specific type I TGF-β1 receptor ALK1, only expressed during the active phase of TGF-β1-mediated angiogenesis (Goumans et al., 2003; Goumans et al., 2002), was increased in CtBP1-transgenic skin (FIG. 11E). These results suggest that activated TGF-β1 signaling in the stroma contributes to increased inflammation and angiogenesis in K5.CtBP1 skin.

Figure 12:
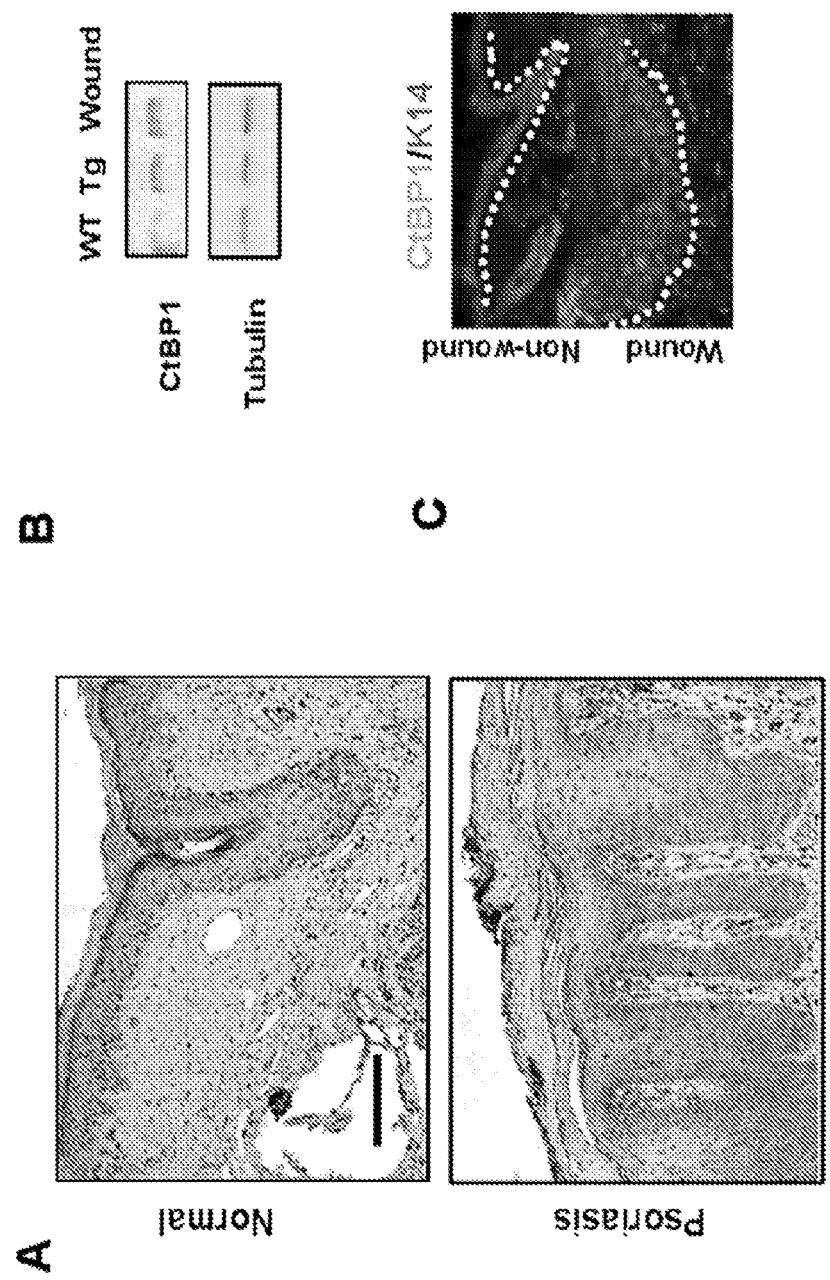
FIG. 12A-C shows pathogenesis associated with CtBP1 overexpression.

Example 10: CtBP1 is Overexpressed in Psoriasis Lesions and the Inflammatory Phase of Wound Healing in Mouse Skin If CtBP1 transactivates TGF-β1 in vivo, CtBP1 would be expected to be elevated in parallel with TGF-β1 overexpression under some pathological conditions. It has been shown that TGF-β1 is overexpressed in human psoriasis (Flisiak et al., 2008; Nockowski et al., 2004). Skin biopsies from healthy volunteers and psoriasis patients were examined. All 10 psoriasis samples displayed uniform nuclear CtBP1 staining in the epidermis, as shown in FIG. 12A. Cells with CtBP1 positive nuclei were also detected in infiltrated leukocytes between rete ridges. In contrast, all 10 normal skin samples showed only sporadic CtBP1-positive cells in the epidermis and stroma (FIG. 12A). Next, CtBP1 expression in mouse skin wounds was examined, in which TGF-β1 is elevated at the acute inflammation phase (Li et al., 2004). A 6-mm punch biopsy induced CtBP1 expression 3-4 fold higher than non-wounded skin on day 3 after wounding, shown in FIG. 12B, when TGF-β1 is at its peak level during wound healing (Li et al., 2004) Immunofluorescence showed nuclear CtBP1 staining primarily in the migrating tongue behind the leading edge and in the wound stroma (FIG. 12C). These data suggest that CtBP1 plays a role in the inflammatory response and that CtBP1 overexpression may contribute to pathological conditions such as psoriasis and chronic inflammation.

Figure 13:
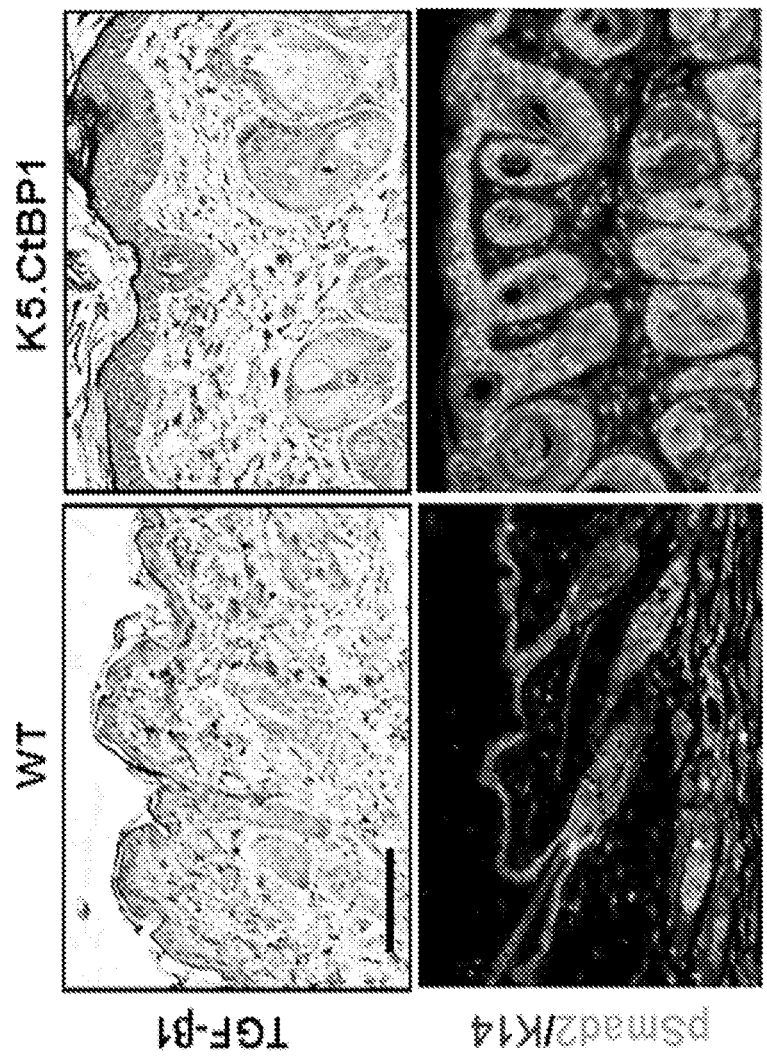
FIG. 13 shows increased TGF-β1 signaling in K5.CtBP1 skin. Immunohistochemistry imaging of TGF-β1 (counterstained with hematoxylin) and immunofluorescence staining of phosphorylated Smad2 (counterstained with a red K14 antibody).

Example 11: TGF-β1 Signaling is Responsible for Inflammation and Angiogenesis in K5.CtBP1 Skin K5.CtBP1 skin displayed increased TGF-β1 Signaling. The top panel of FIG. 13 shows that the TGF-β1 protein was barely detectable in wild type skin, but increased in both the epidermis and stroma of K5.CtBP1 skin. Nuclear staining of phosphorylated Smad2 (pSmad2), a surrogate marker for activated TGF-β1 signaling, was also more prominent in transgenic epidermis and stroma than in wildtype skin (FIG. 13, bottom panel).

To determine whether TGF-β1 activation is required for inflammation and angiogenesis in K5.CtBP1 skin, in vivo knockdown of TGF-β1 by delivery of TGF-β1 siRNA to CtBP1 transgenic skin was performed. The biodegradable polymer PEI F25-LMW (polyethylenimines, F25 low molecular weight, Sigma) was used as a delivery vehicle, preventing degradation and increasing cellular uptake of siRNA in vivo without noticeable toxicity (Hobel et al., 2010). TGF-β1 siRNA mixed with PEI F25-LMW was injected into K5.CtBP1 skin twice per week for 3 weeks to knockdown TGF-β1.

Figure 14:
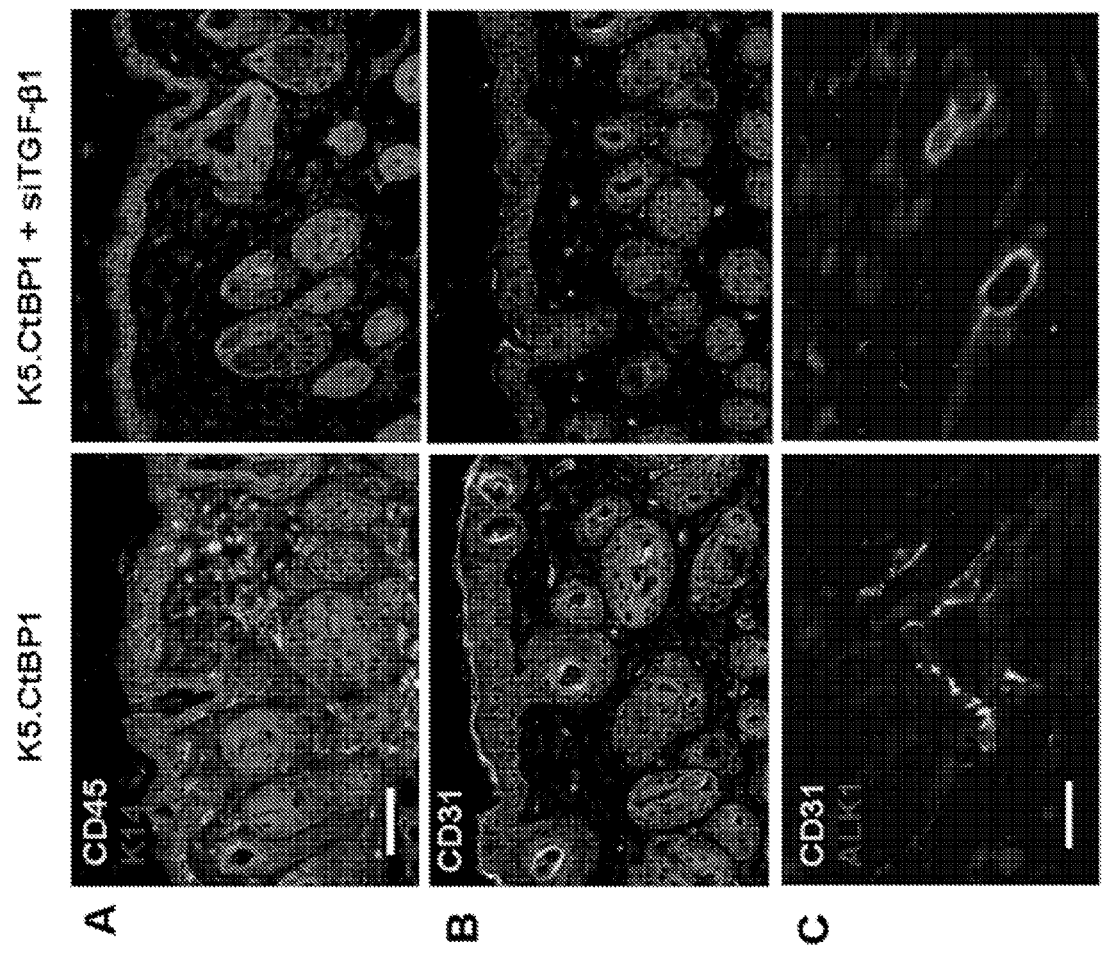
FIG. 14A-C shows TGF-β1-mediated inflammation and angiogenesis in K5.CtBP1 transgenic mice Immunofluorescence images of CD45 (green, FIG. 14A), CD31 (green, FIG. 14B), and ALK1 (red, FIG. 14C). Sections in FIG. 14A and FIG. 14B were counterstained with a K14 (red) antibody. Sections in FIG. 14C were counterstained with a CD31 (green) antibody.

FIG. 14A shows that inflammation, as shown by CD45 staining, was consequently significantly decreased by TGF-β1 siRNA-treatment in K5.CtBP1 skin. In addition, CD31$^+$ vessels (FIG. 14B) and ALK1-positive vessels (FIG. 14C) were decreased. These data suggest that TGF-β1 up-regulation is the key mediator of CtBP1's effect on inflammation and angiogenesis.

Figure 15:
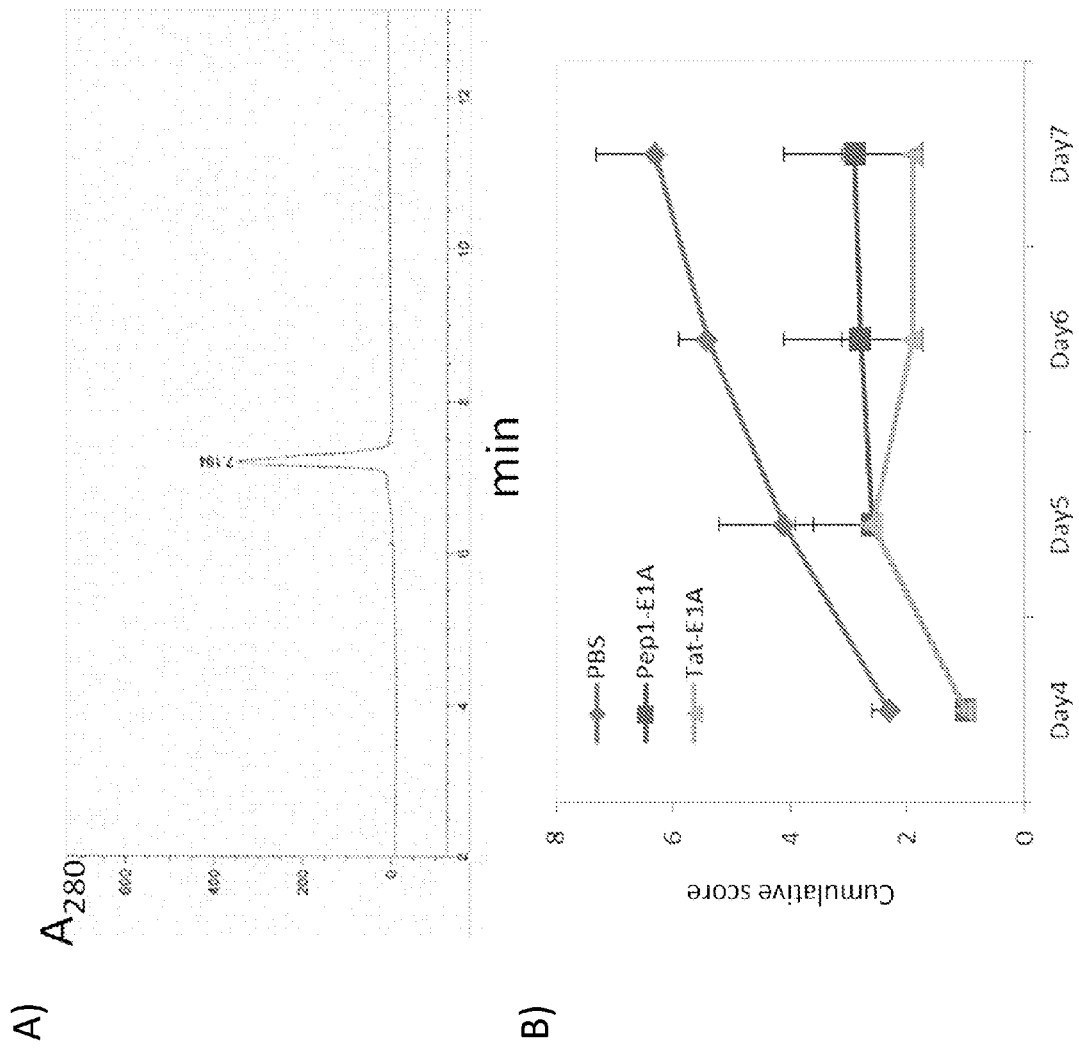
FIG. 15A-B) shows treatment of psoriasis with a Pep1-E1A peptide and a Tat-E1A peptide.

Example 12: Treatment of Psoriasis by Interfering with the Interaction Between E1A and CtBP To evaluate the therapeutic effect of the E1A derived peptide EQTVPVDLSVARPR (SEQ ID NO:132) that demonstrated high affinity to CtBP1 (Kd=2.2 uM), a Tat-fusion peptide was synthesized and purified by HPLC (FIG. 15A). The Tat-E1A peptide was evaluated in an IMQ-based psoriasis model and the efficacy of the Tat-E1A peptide (GRK-KRRQRRRPPQGGEQTVPVDLSVARPRGL; SEQ ID NO:137) conjugated to FITC was compared to a Pep1-E1A peptide (GSHMKETWWETWWTEWSQPKKKRKV-LEEPGQPLDLSCQRPRDYKDDDDK; SEQ ID NO:127). Tat-E1A peptide treatment significantly reduced the psoriasis-like phenotype when the Tat-E1A peptide was subcutaneously applied on the skin (FIG. 15B). The PBS treated control group (FIG. 15, diamond) displayed inflamed scaly skin lesions resembling plaque type psoriasis following IMQ-induction. Mice treated with either the Pep-E1A peptide (FIG. 15B, square) or the Tat-E1A peptide (FIG. 15B, triangle) showed resistance to IMQ-induction of psoriasis.

The invention claimed is:

1. A method of treating psoriasis in an individual, the method comprising administering to the individual an effective amount of a peptide comprising the amino acid sequence of SEQ ID NO:23 (KETWWETWWTEWSQPKKKRKVLEEPGQPLDLSCKRPR).

2. A method of reducing inflammation in an individual suffering from psoriasis, the method comprising administering to the individual an effective amount of a peptide comprising the amino acid sequence of SEQ ID NO:23 (KETWWETWWTEWSQPKKKRKVLEEPGQPLDLSCKRPR).

3. The method of claim 1, wherein the peptide is administered intravenously, subcutaneously, orally, or topically to the individual.

4. The method of claim 1, wherein the peptide is formulated in a pharmaceutically acceptable composition.

5. The method of claim 2, wherein the peptide is administered intravenously, subcutaneously, orally, or topically to the individual.

6. The method of claim 2, wherein the peptide is formulated in a pharmaceutically acceptable composition.

* * * * *

UNITED STATES PATENT AND TRADEMARK OFFICE
CERTIFICATE OF CORRECTION

Page 1 of 1

PATENT NO. : 9,683,025 B2
APPLICATION NO. : 14/775643
DATED : June 20, 2017
INVENTOR(S) : Qinghong Zhang et al.

It is certified that error appears in the above-identified patent and that said Letters Patent is hereby corrected as shown below:

In the Specification

In Column 1, Lines 20-22, please replace the paragraph immediately following the heading, STATEMENT REGARDING FEDERALLY SPONSORED RESEARCH OR DEVELOPMENT, as follows:

-- This invention was made with government support under grant numbers CA115468, DA033982 and CA079998, awarded by the National Institutes of Health. The government has certain rights in the invention. --

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 170

<210> SEQ ID NO 1
<211> LENGTH: 14
<212> TYPE: PRT
<213> ORGANISM: Artificial Sequence
<220> FEATURE:
<223> OTHER INFORMATION: Synthetic Construct

<400> SEQUENCE: 1

Glu Pro Gly Gln Pro Leu Asp Leu Ser Cys Lys Arg Pro Arg
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Any Amino Acid

<400> SEQUENCE: 2

Pro Xaa Asp Leu Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct

<400> SEQUENCE: 3
```

Pro Leu Asp Leu Ser
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 6
<223> OTHER INFORMATION: Xaa = Any Amino Acid
<220> FEATURE:
<221> NAME/KEY: VARIANT
<222> LOCATION: 7
<223> OTHER INFORMATION: Xaa = any amino acid having a bulky side chain

<400> SEQUENCE: 4

Pro Xaa Asp Leu Ser Xaa Xaa
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 6
<223> OTHER INFORMATION: Xaa = Any Amino Acid
<220> FEATURE:
<221> NAME/KEY: VARIANT
<222> LOCATION: 7
<223> OTHER INFORMATION: Xaa = R or K

<400> SEQUENCE: 5

Pro Xaa Asp Leu Ser Xaa Xaa
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 6
<223> OTHER INFORMATION: Xaa = Any Amino Acid

<400> SEQUENCE: 6

Pro Xaa Asp Leu Ser Xaa Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 6
<223> OTHER INFORMATION: Xaa = Any Amino Acid

<400> SEQUENCE: 7

Pro Xaa Asp Leu Ser Xaa Gln
1               5

```
<210> SEQ ID NO 8
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 7
<223> OTHER INFORMATION: Xaa = any amino acid having a bulky side chain

<400> SEQUENCE: 8

Pro Leu Asp Leu Ser Xaa Xaa
 1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 7
<223> OTHER INFORMATION: Xaa = R or K

<400> SEQUENCE: 9

Pro Leu Asp Leu Ser Xaa Xaa
 1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Any Amino Acid

<400> SEQUENCE: 10

Pro Leu Asp Leu Ser Xaa Lys
 1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Any Amino Acid

<400> SEQUENCE: 11

Pro Leu Asp Leu Ser Xaa Gln
 1               5

<210> SEQ ID NO 12
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 12

Pro Leu Asp Leu Ser Cys Lys
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct

<400> SEQUENCE: 13

Pro Leu Asp Leu Ser Cys Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Pro Leu Asp Leu Ser Cys Gln
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

<400> SEQUENCE: 15

Pro Leu Asp Leu Ser Cys Lys Arg Pro Arg
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Pro Leu Asp Leu Ser Cys Arg Pro Arg
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Pro Leu Asp Leu Ser Cys Gln Arg Pro Arg
1               5                   10

<210> SEQ ID NO 18
<211> LENGTH: 14
<212> TYPE: PRT
```

```
<213> ORGANISM: Artificial Sequence
<220> FEATURE:
<223> OTHER INFORMATION: Synthetic Construct

<400> SEQUENCE: 18

Glu Pro Gly Gln Pro Leu Asp Leu Ser Cys Arg Pro Arg Pro
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Synthetic Construct

<400> SEQUENCE: 19

Glu Pro Gly Gln Pro Leu Asp Leu Ser Cys Gln Arg Pro Arg
1               5                   10

<210> SEQ ID NO 20
<211> LENGTH: 29
<212> TYPE: PRT
<213> ORGANISM: Artificial Sequence
<220> FEATURE:
<223> OTHER INFORMATION: Synthetic Construct

<400> SEQUENCE: 20

Gly Arg Lys Lys Arg Arg Gln Arg Arg Pro Pro Gln Leu Glu Glu
1               5                   10                  15

Pro Gly Gln Pro Leu Asp Leu Ser Cys Lys Arg Pro Arg
            20                  25

<210> SEQ ID NO 21
<211> LENGTH: 29
<212> TYPE: PRT
<213> ORGANISM: Artificial Sequence
<220> FEATURE:
<223> OTHER INFORMATION: Synthetic Construct

<400> SEQUENCE: 21

Gly Arg Lys Lys Arg Arg Gln Arg Arg Pro Pro Gln Leu Glu Glu
1               5                   10                  15

Pro Gly Gln Pro Leu Asp Glu Leu Cys Lys Arg Pro Arg
            20                  25

<210> SEQ ID NO 22
<211> LENGTH: 29
<212> TYPE: PRT
<213> ORGANISM: Artificial Sequence
<220> FEATURE:
<223> OTHER INFORMATION: Synthetic Construct

<400> SEQUENCE: 22

Gly Arg Lys Lys Arg Arg Gln Arg Arg Pro Pro Gln Leu Glu Glu
1               5                   10                  15

Pro Gly Gln Pro Leu Asp Leu Ser Cys Gln Arg Pro Arg
            20                  25

<210> SEQ ID NO 23
<211> LENGTH: 37
<212> TYPE: PRT
<213> ORGANISM: Artificial Sequence
<220> FEATURE:
<223> OTHER INFORMATION: Synthetic Construct

<400> SEQUENCE: 23
```

```
Lys Glu Thr Trp Trp Glu Thr Trp Trp Thr Glu Trp Ser Gln Pro Lys
1               5                   10                  15

Lys Lys Arg Lys Val Leu Glu Glu Pro Gly Gln Pro Leu Asp Leu Ser
                20                  25                  30

Cys Lys Arg Pro Arg
        35

<210> SEQ ID NO 24
<211> LENGTH: 37
<212> TYPE: PRT
<213> ORGANISM: Artificial Sequence
<220> FEATURE:
<223> OTHER INFORMATION: Synthetic Construct

<400> SEQUENCE: 24

Lys Glu Thr Trp Trp Glu Thr Trp Trp Thr Glu Trp Ser Gln Pro Lys
1               5                   10                  15

Lys Lys Arg Lys Val Leu Glu Glu Pro Gly Gln Pro Leu Asp Glu Leu
                20                  25                  30

Cys Lys Arg Pro Arg
        35

<210> SEQ ID NO 25
<211> LENGTH: 37
<212> TYPE: PRT
<213> ORGANISM: Artificial Sequence
<220> FEATURE:
<223> OTHER INFORMATION: Synthetic Construct

<400> SEQUENCE: 25

Lys Glu Thr Trp Trp Glu Thr Trp Trp Thr Glu Trp Ser Gln Pro Lys
1               5                   10                  15

Lys Lys Arg Lys Val Leu Glu Glu Pro Gly Gln Pro Leu Asp Glu Leu
                20                  25                  30

Cys Gln Arg Pro Arg
        35

<210> SEQ ID NO 26
<211> LENGTH: 33
<212> TYPE: PRT
<213> ORGANISM: Artificial Sequence
<220> FEATURE:
<223> OTHER INFORMATION: Synthetic Construct

<400> SEQUENCE: 26

Gly Ser His Met Gly Arg Lys Lys Arg Arg Gln Arg Arg Pro Pro
1               5                   10                  15

Gln Leu Glu Glu Pro Gly Gln Pro Leu Asp Leu Ser Cys Lys Arg Pro
                20                  25                  30

Arg

<210> SEQ ID NO 27
<211> LENGTH: 33
<212> TYPE: PRT
<213> ORGANISM: Artificial Sequence
<220> FEATURE:
<223> OTHER INFORMATION: Synthetic Construct

<400> SEQUENCE: 27

Gly Ser His Met Gly Arg Lys Lys Arg Arg Gln Arg Arg Pro Pro
1               5                   10                  15
```

Gln Leu Glu Glu Pro Gly Gln Pro Leu Asp Glu Leu Cys Lys Arg Pro
            20                  25                  30

Arg

<210> SEQ ID NO 28
<211> LENGTH: 33
<212> TYPE: PRT
<213> ORGANISM: Artificial Sequence
<220> FEATURE:
<223> OTHER INFORMATION: Synthetic Construct

<400> SEQUENCE: 28

Gly Ser His Met Gly Arg Lys Lys Arg Gln Arg Arg Pro Pro
1               5                   10                  15

Gln Leu Glu Glu Pro Gly Gln Pro Leu Asp Leu Ser Cys Gln Arg Pro
            20                  25                  30

Arg

<210> SEQ ID NO 29
<211> LENGTH: 41
<212> TYPE: PRT
<213> ORGANISM: Artificial Sequence
<220> FEATURE:
<223> OTHER INFORMATION: Synthetic Construct

<400> SEQUENCE: 29

Gly Ser His Met Lys Glu Thr Trp Trp Glu Thr Trp Trp Thr Glu Trp
1               5                   10                  15

Ser Gln Pro Lys Lys Lys Arg Lys Val Leu Glu Glu Pro Gly Gln Pro
            20                  25                  30

Leu Asp Leu Ser Cys Lys Arg Pro Arg
        35                  40

<210> SEQ ID NO 30
<211> LENGTH: 41
<212> TYPE: PRT
<213> ORGANISM: Artificial Sequence
<220> FEATURE:
<223> OTHER INFORMATION: Synthetic Construct

<400> SEQUENCE: 30

Gly Ser His Met Lys Glu Thr Trp Trp Glu Thr Trp Trp Thr Glu Trp
1               5                   10                  15

Ser Gln Pro Lys Lys Lys Arg Lys Val Leu Glu Glu Pro Gly Gln Pro
            20                  25                  30

Leu Asp Glu Leu Cys Lys Arg Pro Arg
        35                  40

<210> SEQ ID NO 31
<211> LENGTH: 41
<212> TYPE: PRT
<213> ORGANISM: Artificial Sequence
<220> FEATURE:
<223> OTHER INFORMATION: Synthetic Construct

<400> SEQUENCE: 31

Gly Ser His Met Lys Glu Thr Trp Trp Glu Thr Trp Trp Thr Glu Trp
1               5                   10                  15

Ser Gln Pro Lys Lys Lys Arg Lys Val Leu Glu Glu Pro Gly Gln Pro
            20                  25                  30

Leu Asp Glu Leu Cys Gln Arg Pro Arg
        35                  40

<210> SEQ ID NO 32
<211> LENGTH: 21
<212> TYPE: PRT
<213> ORGANISM: Artificial Sequence
<220> FEATURE:
<223> OTHER INFORMATION: Synthetic Construct

<400> SEQUENCE: 32

Thr Arg Ser Ser Arg Ala Gly Leu Gln Phe Pro Val Gly Arg Val His
1               5                   10                  15

Arg Leu Leu Arg Lys
            20

<210> SEQ ID NO 33
<211> LENGTH: 16
<212> TYPE: PRT
<213> ORGANISM: Artificial Sequence
<220> FEATURE:
<223> OTHER INFORMATION: Synthetic Construct

<400> SEQUENCE: 33

Arg Lys Lys Arg Arg Glu Ser Arg Lys Lys Arg Arg Arg Glu Ser
1               5                   10                  15

<210> SEQ ID NO 34
<211> LENGTH: 17
<212> TYPE: PRT
<213> ORGANISM: Artificial Sequence
<220> FEATURE:
<223> OTHER INFORMATION: Synthetic Construct

<400> SEQUENCE: 34

Gly Arg Pro Arg Glu Ser Gly Lys Lys Arg Lys Arg Lys Arg Leu Lys
1               5                   10                  15

Pro

<210> SEQ ID NO 35
<211> LENGTH: 15
<212> TYPE: PRT
<213> ORGANISM: Artificial Sequence
<220> FEATURE:
<223> OTHER INFORMATION: Synthetic Construct

<400> SEQUENCE: 35

Gly Lys Arg Lys Lys Lys Gly Lys Leu Gly Lys Lys Arg Asp Pro
1               5                   10                  15

<210> SEQ ID NO 36
<211> LENGTH: 17
<212> TYPE: PRT
<213> ORGANISM: Artificial Sequence
<220> FEATURE:
<223> OTHER INFORMATION: Synthetic Construct

<400> SEQUENCE: 36

Gly Lys Arg Lys Lys Lys Gly Lys Leu Gly Lys Lys Arg Pro Arg Ser
1               5                   10                  15

Arg

<210> SEQ ID NO 37
<211> LENGTH: 18
<212> TYPE: PRT
<213> ORGANISM: Artificial Sequence
<220> FEATURE:

<223> OTHER INFORMATION: Synthetic Construct

<400> SEQUENCE: 37

Arg Lys Lys Arg Arg Arg Glu Ser Arg Arg Ala Arg Arg Ser Pro Arg
1               5                   10                  15

His Leu

<210> SEQ ID NO 38
<211> LENGTH: 19
<212> TYPE: PRT
<213> ORGANISM: Artificial Sequence
<220> FEATURE:
<223> OTHER INFORMATION: Synthetic Construct

<400> SEQUENCE: 38

Ser Arg Arg Ala Arg Arg Ser Pro Arg Glu Ser Gly Lys Lys Arg Lys
1               5                   10                  15

Arg Lys Arg

<210> SEQ ID NO 39
<211> LENGTH: 19
<212> TYPE: PRT
<213> ORGANISM: Artificial Sequence
<220> FEATURE:
<223> OTHER INFORMATION: Synthetic Construct

<400> SEQUENCE: 39

Val Lys Arg Gly Leu Lys Leu Arg His Val Arg Pro Arg Val Thr Arg
1               5                   10                  15

Met Asp Val

<210> SEQ ID NO 40
<211> LENGTH: 18
<212> TYPE: PRT
<213> ORGANISM: Artificial Sequence
<220> FEATURE:
<223> OTHER INFORMATION: Synthetic Construct

<400> SEQUENCE: 40

Val Lys Arg Gly Leu Lys Leu Arg His Val Arg Pro Arg Val Thr Arg
1               5                   10                  15

Asp Val

<210> SEQ ID NO 41
<211> LENGTH: 14
<212> TYPE: PRT
<213> ORGANISM: Artificial Sequence
<220> FEATURE:
<223> OTHER INFORMATION: Synthetic Construct

<400> SEQUENCE: 41

Ser Arg Arg Ala Arg Arg Ser Pro Arg His Leu Gly Ser Gly
1               5                   10

<210> SEQ ID NO 42
<211> LENGTH: 16
<212> TYPE: PRT
<213> ORGANISM: Artificial Sequence
<220> FEATURE:
<223> OTHER INFORMATION: Synthetic Construct

<400> SEQUENCE: 42

Leu Arg Arg Glu Arg Gln Ser Arg Leu Arg Arg Glu Arg Gln Ser Arg
1               5                   10                  15

<210> SEQ ID NO 43
<211> LENGTH: 22
<212> TYPE: PRT
<213> ORGANISM: Artificial Sequence
<220> FEATURE:
<223> OTHER INFORMATION: Synthetic Construct

<400> SEQUENCE: 43

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 44
<211> LENGTH: 30
<212> TYPE: PRT
<213> ORGANISM: Artificial Sequence
<220> FEATURE:
<223> OTHER INFORMATION: Synthetic Construct

<400> SEQUENCE: 44

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 45

<400> SEQUENCE: 45

000

<210> SEQ ID NO 46
<211> LENGTH: 21
<212> TYPE: PRT
<213> ORGANISM: Artificial Sequence
<220> FEATURE:
<223> OTHER INFORMATION: Synthetic Construct

<400> SEQUENCE: 46

Lys Gly Ser Trp Tyr Ser Met Arg Lys Met Ser Met Lys Ile Arg Pro
1               5                   10                  15

Phe Phe Pro Gln Gln
            20

<210> SEQ ID NO 47
<211> LENGTH: 20
<212> TYPE: PRT
<213> ORGANISM: Artificial Sequence
<220> FEATURE:
<223> OTHER INFORMATION: Synthetic Construct

<400> SEQUENCE: 47

Lys Thr Arg Tyr Tyr Ser Met Lys Lys Thr Thr Met Lys Ile Ile Pro
1               5                   10                  15

Phe Asn Arg Leu
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic Construct

<400> SEQUENCE: 48

Arg Gly Ala Asp Tyr Ser Leu Arg Ala Val Arg Met Lys Ile Arg Pro
1               5                   10                  15

Leu Val Thr Gln
            20

<210> SEQ ID NO 49
<211> LENGTH: 24
<212> TYPE: PRT
<213> ORGANISM: Artificial Sequence
<220> FEATURE:
<223> OTHER INFORMATION: Synthetic Construct

<400> SEQUENCE: 49

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 50
<211> LENGTH: 12
<212> TYPE: PRT
<213> ORGANISM: Artificial Sequence
<220> FEATURE:
<223> OTHER INFORMATION: Synthetic Construct

<400> SEQUENCE: 50

Thr Ser Pro Leu Asn Ile His Asn Gly Gln Lys Leu
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic Construct

<400> SEQUENCE: 51

Asn Ser Ala Ala Phe Glu Asp Leu Arg Val Leu Ser
1               5                   10

<210> SEQ ID NO 52
<211> LENGTH: 30
<212> TYPE: PRT
<213> ORGANISM: Artificial Sequence
<220> FEATURE:
<223> OTHER INFORMATION: Synthetic Construct

<400> SEQUENCE: 52

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 53
<211> LENGTH: 16
<212> TYPE: PRT
<213> ORGANISM: Artificial Sequence
<220> FEATURE:
<223> OTHER INFORMATION: Synthetic Construct

<400> SEQUENCE: 53

Ala Ala Val Ala Leu Leu Pro Ala Val Leu Leu Ala Leu Leu Ala Pro
1               5                   10                  15

```
<210> SEQ ID NO 54
<211> LENGTH: 10
<212> TYPE: PRT
<213> ORGANISM: Artificial Sequence
<220> FEATURE:
<223> OTHER INFORMATION: Synthetic Construct

<400> SEQUENCE: 54

Val Pro Met Leu Lys Pro Met Leu Lys Glu
1               5                   10

<210> SEQ ID NO 55
<211> LENGTH: 18
<212> TYPE: PRT
<213> ORGANISM: Artificial Sequence
<220> FEATURE:
<223> OTHER INFORMATION: Synthetic Construct

<400> SEQUENCE: 55

Lys Leu Ala Leu Lys Leu Ala Leu Lys Ala Leu Lys Ala Ala Leu Lys
1               5                   10                  15

Leu Ala

<210> SEQ ID NO 56
<211> LENGTH: 27
<212> TYPE: PRT
<213> ORGANISM: Artificial Sequence
<220> FEATURE:
<223> OTHER INFORMATION: Synthetic Construct

<400> SEQUENCE: 56

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 57
<211> LENGTH: 16
<212> TYPE: PRT
<213> ORGANISM: Artificial Sequence
<220> FEATURE:
<223> OTHER INFORMATION: Synthetic Construct

<400> SEQUENCE: 57

Ala Ala Val Ala Leu Leu Pro Ala Val Leu Leu Ala Leu Leu Ala Pro
1               5                   10                  15

<210> SEQ ID NO 58
<211> LENGTH: 9
<212> TYPE: PRT
<213> ORGANISM: Artificial Sequence
<220> FEATURE:
<223> OTHER INFORMATION: Synthetic Construct

<400> SEQUENCE: 58

Val Gln Arg Lys Arg Gln Lys Leu Met
1               5

<210> SEQ ID NO 59
<211> LENGTH: 16
<212> TYPE: PRT
<213> ORGANISM: Artificial Sequence
<220> FEATURE:
<223> OTHER INFORMATION: Synthetic Construct
```

```
<400> SEQUENCE: 59

Arg Gln Ile Lys Ile Trp Phe Gln Asn Arg Arg Met Lys Trp Lys Lys
1               5                   10                  15

<210> SEQ ID NO 60
<211> LENGTH: 21
<212> TYPE: PRT
<213> ORGANISM: Artificial Sequence
<220> FEATURE:
<223> OTHER INFORMATION: Synthetic Construct

<400> SEQUENCE: 60

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 61
<211> LENGTH: 15
<212> TYPE: PRT
<213> ORGANISM: Artificial Sequence
<220> FEATURE:
<223> OTHER INFORMATION: Synthetic Construct

<400> SEQUENCE: 61

Ser Asp Leu Trp Glu Met Met Met Val Ser Leu Ala Cys Gln Tyr
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Synthetic Construct

<400> SEQUENCE: 62

Arg Gln Ile Lys Ile Trp Phe Gln Asn Arg Arg Met Lys Trp Lys Lys
1               5                   10                  15

<210> SEQ ID NO 63
<211> LENGTH: 7
<212> TYPE: PRT
<213> ORGANISM: Artificial Sequence
<220> FEATURE:
<223> OTHER INFORMATION: Synthetic Construct

<400> SEQUENCE: 63

Arg Arg Met Lys Trp Lys Lys
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic Construct

<400> SEQUENCE: 64

Arg Arg Arg Arg Arg Arg Arg
1               5

<210> SEQ ID NO 65
<211> LENGTH: 9
<212> TYPE: PRT
<213> ORGANISM: Artificial Sequence
<220> FEATURE:
```

```
<223> OTHER INFORMATION: Synthetic Construct

<400> SEQUENCE: 65

Arg Arg Arg Arg Arg Arg Arg Arg Arg
1               5

<210> SEQ ID NO 66
<211> LENGTH: 16
<212> TYPE: PRT
<213> ORGANISM: Artificial Sequence
<220> FEATURE:
<223> OTHER INFORMATION: Synthetic Construct

<400> SEQUENCE: 66

Arg Val Ile Arg Val Trp Phe Gln Asn Lys Arg Cys Lys Asp Lys Lys
1               5                   10                  15

<210> SEQ ID NO 67
<211> LENGTH: 28
<212> TYPE: PRT
<213> ORGANISM: Artificial Sequence
<220> FEATURE:
<223> OTHER INFORMATION: Synthetic Construct

<400> SEQUENCE: 67

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 68
<211> LENGTH: 18
<212> TYPE: PRT
<213> ORGANISM: Artificial Sequence
<220> FEATURE:
<223> OTHER INFORMATION: Synthetic Construct

<400> SEQUENCE: 68

Leu Leu Ile Ile Leu Arg Arg Arg Ile Arg Lys Gln Ala His Ala His
1               5                   10                  15

Ser Lys

<210> SEQ ID NO 69
<211> LENGTH: 18
<212> TYPE: PRT
<213> ORGANISM: Artificial Sequence
<220> FEATURE:
<223> OTHER INFORMATION: Synthetic Construct

<400> SEQUENCE: 69

Val Arg Leu Pro Pro Pro Val Arg Leu Pro Pro Pro Val Arg Leu Pro
1               5                   10                  15

Pro Pro

<210> SEQ ID NO 70
<211> LENGTH: 7
<212> TYPE: PRT
<213> ORGANISM: Artificial Sequence
<220> FEATURE:
<223> OTHER INFORMATION: Synthetic Construct

<400> SEQUENCE: 70

Pro Lys Lys Lys Arg Lys Val
1               5
```

```
<210> SEQ ID NO 71
<211> LENGTH: 18
<212> TYPE: PRT
<213> ORGANISM: Artificial Sequence
<220> FEATURE:
<223> OTHER INFORMATION: Synthetic Construct

<400> SEQUENCE: 71

Arg Gly Gly Arg Leu Ser Tyr Ser Arg Arg Phe Ser Thr Ser Thr
1               5                   10                  15

Gly Arg

<210> SEQ ID NO 72
<211> LENGTH: 10
<212> TYPE: PRT
<213> ORGANISM: Artificial Sequence
<220> FEATURE:
<223> OTHER INFORMATION: Synthetic Construct

<400> SEQUENCE: 72

Arg Arg Leu Ser Tyr Ser Arg Arg Arg Phe
1               5                   10

<210> SEQ ID NO 73
<211> LENGTH: 17
<212> TYPE: PRT
<213> ORGANISM: Artificial Sequence
<220> FEATURE:
<223> OTHER INFORMATION: Synthetic Construct

<400> SEQUENCE: 73

Ala Trp Ser Phe Arg Val Ser Tyr Arg Gly Ile Ser Tyr Arg Ser
1               5                   10                  15

Arg

<210> SEQ ID NO 74
<211> LENGTH: 14
<212> TYPE: PRT
<213> ORGANISM: Artificial Sequence
<220> FEATURE:
<223> OTHER INFORMATION: Synthetic Construct

<400> SEQUENCE: 74

Tyr Gly Arg Lys Lys Arg Arg Gln Arg Arg Pro Pro Gln
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Synthetic Construct

<400> SEQUENCE: 75

Gly Arg Lys Lys Arg Arg Gln Arg Arg Pro Pro Gln
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Synthetic Construct

<400> SEQUENCE: 76
```

```
Gly Arg Lys Lys Arg Gln Arg Arg Pro Pro Gln Gln
1               5                   10
```

<210> SEQ ID NO 77
<211> LENGTH: 11
<212> TYPE: PRT
<213> ORGANISM: Artificial Sequence
<220> FEATURE:
<223> OTHER INFORMATION: Synthetic Construct

<400> SEQUENCE: 77

```
Tyr Gly Arg Lys Lys Arg Arg Gln Arg Arg Arg
1               5                   10
```

<210> SEQ ID NO 78
<211> LENGTH: 9
<212> TYPE: PRT
<213> ORGANISM: Artificial Sequence
<220> FEATURE:
<223> OTHER INFORMATION: Synthetic Construct

<400> SEQUENCE: 78

```
Arg Lys Lys Arg Arg Gln Arg Arg Arg
1               5
```

<210> SEQ ID NO 79
<211> LENGTH: 27
<212> TYPE: PRT
<213> ORGANISM: Artificial Sequence
<220> FEATURE:
<223> OTHER INFORMATION: Synthetic Construct

<400> SEQUENCE: 79

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 80
<211> LENGTH: 21
<212> TYPE: PRT
<213> ORGANISM: Artificial Sequence
<220> FEATURE:
<223> OTHER INFORMATION: Synthetic Construct

<400> SEQUENCE: 80

```
Ala Gly Tyr Leu Leu Gly Lys Ile Asn Leu Lys Ala Leu Ala Ala Leu
1               5                   10                  15

Ala Lys Lys Ile Leu
            20
```

<210> SEQ ID NO 81
<211> LENGTH: 12
<212> TYPE: PRT
<213> ORGANISM: Artificial Sequence
<220> FEATURE:
<223> OTHER INFORMATION: Synthetic Construct

<400> SEQUENCE: 81

```
Gly Trp Thr Leu Asn Ser Ala Gly Tyr Leu Leu Gly
1               5                   10
```

<210> SEQ ID NO 82
<211> LENGTH: 34
<212> TYPE: PRT
<213> ORGANISM: Artificial Sequence

```
<220> FEATURE:
<223> OTHER INFORMATION: Synthetic Construct

<400> SEQUENCE: 82

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Asp

<210> SEQ ID NO 83
<211> LENGTH: 26
<212> TYPE: PRT
<213> ORGANISM: Artificial Sequence
<220> FEATURE:
<223> OTHER INFORMATION: Synthetic Construct

<400> SEQUENCE: 83

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 84
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = L, M, Q, or I

<400> SEQUENCE: 84

Pro Xaa Asp Leu Ser
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = L, M, Q, or I
<220> FEATURE:
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 7
<223> OTHER INFORMATION: Xaa = any amino acid having a bulky side chain

<400> SEQUENCE: 85

Pro Xaa Asp Leu Ser Xaa Xaa
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: VARIANT
<222> LOCATION: 2
<223> OTHER INFORMATION: Xaa = L, M, Q or I
<220> FEATURE:
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 7
<223> OTHER INFORMATION: Xaa = R or K

<400> SEQUENCE: 86

Pro Xaa Asp Leu Ser Xaa Xaa
 1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = L, M, Q, or I
<220> FEATURE:
<221> NAME/KEY: VARIANT
<222> LOCATION: 6
<223> OTHER INFORMATION: Xaa = Any Amino Acid

<400> SEQUENCE: 87

Pro Xaa Asp Leu Ser Xaa Lys
 1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = L, M, Q, or I
<220> FEATURE:
<221> NAME/KEY: VARIANT
<222> LOCATION: 6
<223> OTHER INFORMATION: Xaa = Any Amino Acid

<400> SEQUENCE: 88

Pro Xaa Asp Leu Ser Xaa Gln
 1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 6
<223> OTHER INFORMATION: Xaa = C, M, L, or K
<220> FEATURE:
<221> NAME/KEY: VARIANT
<222> LOCATION: 7
<223> OTHER INFORMATION: Xaa = any amino acid having a bulky side chain
```

```
<400> SEQUENCE: 89

Pro Xaa Asp Leu Ser Xaa Xaa
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 6
<223> OTHER INFORMATION: Xaa = C, M, L, or K
<220> FEATURE:
<221> NAME/KEY: VARIANT
<222> LOCATION: 7
<223> OTHER INFORMATION: Xaa = R or K

<400> SEQUENCE: 90

Pro Xaa Asp Leu Ser Xaa Xaa
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 6
<223> OTHER INFORMATION: Xaa = C, M, L, or K

<400> SEQUENCE: 91

Pro Xaa Asp Leu Ser Xaa Lys
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 6
<223> OTHER INFORMATION: Xaa = C, M, L, or K

<400> SEQUENCE: 92

Pro Xaa Asp Leu Ser Xaa Gln
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: VARIANT
<222> LOCATION: 2
<223> OTHER INFORMATION: Xaa = L, M, Q, or I
<220> FEATURE:
<221> NAME/KEY: VARIANT
<222> LOCATION: 6
<223> OTHER INFORMATION: Xaa = C, M, L, or K
<220> FEATURE:
<221> NAME/KEY: VARIANT
<222> LOCATION: 7
<223> OTHER INFORMATION: Xaa = any amino acid having a bulky side chain

<400> SEQUENCE: 93

Pro Xaa Asp Leu Ser Xaa Xaa
  1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = L, M, Q, or I
<220> FEATURE:
<221> NAME/KEY: VARIANT
<222> LOCATION: 6
<223> OTHER INFORMATION: Xaa = C, M, L, or K
<220> FEATURE:
<221> NAME/KEY: VARIANT
<222> LOCATION: 7
<223> OTHER INFORMATION: Xaa = R or K

<400> SEQUENCE: 94

Pro Xaa Asp Leu Ser Xaa Xaa
  1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = L, M, Q, or I
<220> FEATURE:
<221> NAME/KEY: VARIANT
<222> LOCATION: 6
<223> OTHER INFORMATION: Xaa = C, M, L, or K

<400> SEQUENCE: 95

Pro Xaa Asp Leu Ser Xaa Lys
  1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = L, M, Q, or I
<220> FEATURE:
<221> NAME/KEY: VARIANT
<222> LOCATION: 6
<223> OTHER INFORMATION: Xaa = C, M, L, or K
```

<400> SEQUENCE: 96

Pro Xaa Asp Leu Ser Xaa Gln
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 7
<223> OTHER INFORMATION: Xaa = any amino acid having a bulky side chain

<400> SEQUENCE: 97

Pro Leu Asp Leu Ser Xaa Xaa
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 7
<223> OTHER INFORMATION: Xaa = R or K

<400> SEQUENCE: 98

Pro Leu Asp Leu Ser Xaa Xaa
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Any Amino Acid

<400> SEQUENCE: 99

Pro Leu Asp Leu Ser Xaa Lys
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Any Amino Acid

<400> SEQUENCE: 100

Pro Leu Asp Leu Ser Xaa Gln
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = C, M, L, or K
<220> FEATURE:
<221> NAME/KEY: VARIANT
<222> LOCATION: 7
<223> OTHER INFORMATION: Xaa = any amino acid having a bulky side chain

<400> SEQUENCE: 101

Pro Leu Asp Leu Ser Xaa Xaa
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = C, M, L, or K
<220> FEATURE:
<221> NAME/KEY: VARIANT
<222> LOCATION: 7
<223> OTHER INFORMATION: Xaa = R or K

<400> SEQUENCE: 102

Pro Leu Asp Leu Ser Xaa Xaa
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = C, M, L, or K

<400> SEQUENCE: 103

Pro Leu Asp Leu Ser Xaa Lys
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = C, M, L, or K

<400> SEQUENCE: 104

Pro Leu Asp Leu Ser Xaa Gln
1               5

```
<210> SEQ ID NO 105
<211> LENGTH: 13
<212> TYPE: PRT
<213> ORGANISM: Artificial Sequence
<220> FEATURE:
<223> OTHER INFORMATION: Synthetic Construct

<400> SEQUENCE: 105

Glu Pro Gly Gln Pro Leu Asp Leu Ser Cys Arg Pro Arg
 1               5                  10

<210> SEQ ID NO 106
<211> LENGTH: 2
<212> TYPE: PRT
<213> ORGANISM: Artificial Sequence
<220> FEATURE:
<223> OTHER INFORMATION: Synthetic Construct

<400> SEQUENCE: 106

Leu Glu
 1

<210> SEQ ID NO 107
<211> LENGTH: 3
<212> TYPE: PRT
<213> ORGANISM: Artificial Sequence
<220> FEATURE:
<223> OTHER INFORMATION: Synthetic Construct

<400> SEQUENCE: 107

Gly Gly Gly
 1

<210> SEQ ID NO 108
<211> LENGTH: 14
<212> TYPE: PRT
<213> ORGANISM: Artificial Sequence
<220> FEATURE:
<223> OTHER INFORMATION: Synthetic Construct

<400> SEQUENCE: 108

Glu Pro Gly Gln Pro Leu Asp Leu Ser Cys Ala Arg Pro Arg
 1               5                  10

<210> SEQ ID NO 109
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 11
<223> OTHER INFORMATION: Xaa = Acetylated Lys

<400> SEQUENCE: 109

Glu Pro Gly Gln Pro Leu Asp Leu Ser Cys Xaa Arg Pro Arg
 1               5                  10

<210> SEQ ID NO 110
<211> LENGTH: 37
<212> TYPE: PRT
<213> ORGANISM: Artificial Sequence
<220> FEATURE:
<223> OTHER INFORMATION: Synthetic Construct

<400> SEQUENCE: 110
```

Gly Arg Lys Lys Arg Arg Gln Arg Arg Pro Pro Gln Leu Glu Glu
1               5                   10                  15

Pro Gly Gln Pro Leu Asp Leu Ser Cys Lys Arg Pro Asp Tyr Lys
            20                  25                  30

Asp Asp Asp Asp Lys
        35

<210> SEQ ID NO 111
<211> LENGTH: 37
<212> TYPE: PRT
<213> ORGANISM: Artificial Sequence
<220> FEATURE:
<223> OTHER INFORMATION: Synthetic Construct

<400> SEQUENCE: 111

Gly Arg Lys Lys Arg Arg Gln Arg Arg Pro Pro Gln Leu Glu Glu
1               5                   10                  15

Pro Gly Gln Pro Leu Asp Glu Leu Cys Lys Arg Pro Arg Asp Tyr Lys
            20                  25                  30

Asp Asp Asp Asp Lys
        35

<210> SEQ ID NO 112
<211> LENGTH: 37
<212> TYPE: PRT
<213> ORGANISM: Artificial Sequence
<220> FEATURE:
<223> OTHER INFORMATION: Synthetic Construct

<400> SEQUENCE: 112

Gly Arg Lys Lys Arg Arg Gln Arg Arg Pro Pro Gln Leu Glu Glu
1               5                   10                  15

Pro Gly Gln Pro Leu Asp Leu Ser Cys Gln Arg Pro Arg Asp Tyr Lys
            20                  25                  30

Asp Asp Asp Asp Lys
        35

<210> SEQ ID NO 113
<211> LENGTH: 45
<212> TYPE: PRT
<213> ORGANISM: Artificial Sequence
<220> FEATURE:
<223> OTHER INFORMATION: Synthetic Construct

<400> SEQUENCE: 113

Lys Glu Thr Trp Trp Glu Thr Trp Trp Thr Glu Trp Ser Gln Pro Lys
1               5                   10                  15

Lys Lys Arg Lys Val Leu Glu Glu Pro Gly Gln Pro Leu Asp Leu Ser
            20                  25                  30

Cys Lys Arg Pro Arg Asp Tyr Lys Asp Asp Asp Asp Lys
        35                  40                  45

<210> SEQ ID NO 114
<211> LENGTH: 45
<212> TYPE: PRT
<213> ORGANISM: Artificial Sequence
<220> FEATURE:
<223> OTHER INFORMATION: Synthetic Construct

<400> SEQUENCE: 114

Lys Glu Thr Trp Trp Glu Thr Trp Trp Thr Glu Trp Ser Gln Pro Lys
1               5                   10                  15

```
Lys Lys Arg Lys Val Leu Glu Glu Pro Gly Gln Pro Leu Asp Glu Leu
            20                  25                  30

Cys Lys Arg Pro Arg Asp Tyr Lys Asp Asp Asp Lys
        35                  40                  45

<210> SEQ ID NO 115
<211> LENGTH: 45
<212> TYPE: PRT
<213> ORGANISM: Artificial Sequence
<220> FEATURE:
<223> OTHER INFORMATION: Synthetic Construct

<400> SEQUENCE: 115

Lys Glu Thr Trp Trp Glu Thr Trp Trp Thr Glu Trp Ser Gln Pro Lys
1               5                   10                  15

Lys Lys Arg Lys Val Leu Glu Glu Pro Gly Gln Pro Leu Asp Glu Leu
            20                  25                  30

Cys Gln Arg Pro Arg Asp Tyr Lys Asp Asp Asp Lys
        35                  40                  45

<210> SEQ ID NO 116
<211> LENGTH: 41
<212> TYPE: PRT
<213> ORGANISM: Artificial Sequence
<220> FEATURE:
<223> OTHER INFORMATION: Synthetic Construct

<400> SEQUENCE: 116

Gly Ser His Met Gly Arg Lys Lys Arg Arg Gln Arg Arg Arg Pro Pro
1               5                   10                  15

Gln Leu Glu Glu Pro Gly Gln Pro Leu Asp Leu Ser Cys Lys Arg Pro
            20                  25                  30

Arg Asp Tyr Lys Asp Asp Asp Lys
        35                  40

<210> SEQ ID NO 117
<211> LENGTH: 41
<212> TYPE: PRT
<213> ORGANISM: Artificial Sequence
<220> FEATURE:
<223> OTHER INFORMATION: Synthetic Construct

<400> SEQUENCE: 117

Gly Ser His Met Gly Arg Lys Lys Arg Arg Gln Arg Arg Arg Pro Pro
1               5                   10                  15

Gln Leu Glu Glu Pro Gly Gln Pro Leu Asp Glu Leu Cys Lys Arg Pro
            20                  25                  30

Arg Asp Tyr Lys Asp Asp Asp Lys
        35                  40

<210> SEQ ID NO 118
<211> LENGTH: 41
<212> TYPE: PRT
<213> ORGANISM: Artificial Sequence
<220> FEATURE:
<223> OTHER INFORMATION: Synthetic Construct

<400> SEQUENCE: 118

Gly Ser His Met Gly Arg Lys Lys Arg Arg Gln Arg Arg Arg Pro Pro
1               5                   10                  15

Gln Leu Glu Glu Pro Gly Gln Pro Leu Asp Leu Ser Cys Gln Arg Pro
            20                  25                  30
```

Arg Asp Tyr Lys Asp Asp Asp Lys
        35                  40

<210> SEQ ID NO 119
<211> LENGTH: 49
<212> TYPE: PRT
<213> ORGANISM: Artificial Sequence
<220> FEATURE:
<223> OTHER INFORMATION: Synthetic Construct

<400> SEQUENCE: 119

Gly Ser His Met Lys Glu Thr Trp Trp Glu Thr Trp Trp Thr Glu Trp
1               5                   10                  15

Ser Gln Pro Lys Lys Lys Arg Lys Val Leu Glu Glu Pro Gly Gln Pro
            20                  25                  30

Leu Asp Leu Ser Cys Lys Arg Pro Arg Asp Tyr Lys Asp Asp Asp Asp
        35                  40                  45

Lys

<210> SEQ ID NO 120
<211> LENGTH: 49
<212> TYPE: PRT
<213> ORGANISM: Artificial Sequence
<220> FEATURE:
<223> OTHER INFORMATION: Synthetic Construct

<400> SEQUENCE: 120

Gly Ser His Met Lys Glu Thr Trp Trp Glu Thr Trp Trp Thr Glu Trp
1               5                   10                  15

Ser Gln Pro Lys Lys Lys Arg Lys Val Leu Glu Glu Pro Gly Gln Pro
            20                  25                  30

Leu Asp Glu Leu Cys Lys Arg Pro Arg Asp Tyr Lys Asp Asp Asp Asp
        35                  40                  45

Lys

<210> SEQ ID NO 121
<211> LENGTH: 49
<212> TYPE: PRT
<213> ORGANISM: Artificial Sequence
<220> FEATURE:
<223> OTHER INFORMATION: Synthetic Construct

<400> SEQUENCE: 121

Gly Ser His Met Lys Glu Thr Trp Trp Glu Thr Trp Trp Thr Glu Trp
1               5                   10                  15

Ser Gln Pro Lys Lys Lys Arg Lys Val Leu Glu Glu Pro Gly Gln Pro
            20                  25                  30

Leu Asp Glu Leu Cys Gln Arg Pro Arg Asp Tyr Lys Asp Asp Asp Asp
        35                  40                  45

Lys

<210> SEQ ID NO 122
<211> LENGTH: 10
<212> TYPE: PRT
<213> ORGANISM: Artificial Sequence
<220> FEATURE:
<223> OTHER INFORMATION: Synthetic Construct

<400> SEQUENCE: 122

Pro Leu Asp Leu Ser Cys Arg Arg Pro Arg
1               5                   10

```
<210> SEQ ID NO 123
<211> LENGTH: 14
<212> TYPE: PRT
<213> ORGANISM: Artificial Sequence
<220> FEATURE:
<223> OTHER INFORMATION: Synthetic Construct

<400> SEQUENCE: 123

Glu Pro Gly Gln Pro Leu Asp Leu Ser Cys Arg Arg Pro Arg
1               5                   10

<210> SEQ ID NO 124
<211> LENGTH: 37
<212> TYPE: PRT
<213> ORGANISM: Artificial Sequence
<220> FEATURE:
<223> OTHER INFORMATION: Synthetic Construct

<400> SEQUENCE: 124

Lys Glu Thr Trp Trp Glu Thr Trp Trp Thr Glu Trp Ser Gln Pro Lys
1               5                   10                  15

Lys Lys Arg Lys Val Leu Glu Glu Pro Gly Gln Pro Leu Asp Leu Ser
            20                  25                  30

Cys Gln Arg Pro Arg
        35

<210> SEQ ID NO 125
<211> LENGTH: 41
<212> TYPE: PRT
<213> ORGANISM: Artificial Sequence
<220> FEATURE:
<223> OTHER INFORMATION: Synthetic Construct

<400> SEQUENCE: 125

Gly Ser His Met Lys Glu Thr Trp Trp Glu Thr Trp Trp Thr Glu Trp
1               5                   10                  15

Ser Gln Pro Lys Lys Lys Arg Lys Val Leu Glu Glu Pro Gly Gln Pro
            20                  25                  30

Leu Asp Leu Ser Cys Gln Arg Pro Arg
        35                  40

<210> SEQ ID NO 126
<211> LENGTH: 45
<212> TYPE: PRT
<213> ORGANISM: Artificial Sequence
<220> FEATURE:
<223> OTHER INFORMATION: Synthetic Construct

<400> SEQUENCE: 126

Lys Glu Thr Trp Trp Glu Thr Trp Trp Thr Glu Trp Ser Gln Pro Lys
1               5                   10                  15

Lys Lys Arg Lys Val Leu Glu Glu Pro Gly Gln Pro Leu Asp Leu Ser
            20                  25                  30

Cys Gln Arg Pro Arg Asp Tyr Lys Asp Asp Asp Lys
        35                  40                  45

<210> SEQ ID NO 127
<211> LENGTH: 49
<212> TYPE: PRT
<213> ORGANISM: Artificial Sequence
<220> FEATURE:
<223> OTHER INFORMATION: Synthetic Construct

<400> SEQUENCE: 127
```

```
Gly Ser His Met Lys Glu Thr Trp Trp Glu Thr Trp Thr Glu Trp
1               5                   10                  15

Ser Gln Pro Lys Lys Arg Lys Val Leu Glu Glu Pro Gly Gln Pro
                20                  25                  30

Leu Asp Leu Ser Cys Gln Arg Pro Arg Asp Tyr Lys Asp Asp Asp
        35                  40                  45

Lys

<210> SEQ ID NO 128
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = a hydrophobic residue
<220> FEATURE:
<221> NAME/KEY: VARIANT
<222> LOCATION: 3
<223> OTHER INFORMATION: Xaa = a residue that preserves hydrogen bonding
      with CtBP
<220> FEATURE:
<221> NAME/KEY: VARIANT
<222> LOCATION: 4
<223> OTHER INFORMATION: Xaa = a hydrophobic residue
<220> FEATURE:
<221> NAME/KEY: VARIANT
<222> LOCATION: 5
<223> OTHER INFORMATION: Xaa = a residue that preserves hydrogen bonding
      with CtBP

<400> SEQUENCE: 128

Pro Xaa Xaa Xaa Xaa
1               5

<210> SEQ ID NO 129
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = L, V, I, M, Q, or E
<220> FEATURE:
<221> NAME/KEY: VARIANT
<222> LOCATION: 3
<223> OTHER INFORMATION: Xaa = D or N
<220> FEATURE:
<221> NAME/KEY: VARIANT
<222> LOCATION: 4
<223> OTHER INFORMATION: Xaa = L or I
<220> FEATURE:
<221> NAME/KEY: VARIANT
<222> LOCATION: 5
<223> OTHER INFORMATION: Xaa = S, C, T, V or A

<400> SEQUENCE: 129

Pro Xaa Xaa Xaa Xaa
1               5

<210> SEQ ID NO 130
<211> LENGTH: 14
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: VARIANT
<222> LOCATION: 1
<223> OTHER INFORMATION: Xaa = E, G, P, A or V
<220> FEATURE:
<221> NAME/KEY: VARIANT
<222> LOCATION: 2
<223> OTHER INFORMATION: Xaa = P, Q, G, S, T, V or M
<220> FEATURE:
<221> NAME/KEY: VARIANT
<222> LOCATION: 3
<223> OTHER INFORMATION: Xaa = G, T, D, E or N
<220> FEATURE:
<221> NAME/KEY: VARIANT
<222> LOCATION: 4
<223> OTHER INFORMATION: Xaa = Q, V, E or G
<220> FEATURE:
<221> NAME/KEY: VARIANT
<222> LOCATION: 6
<223> OTHER INFORMATION: Xaa = a hydrophobic residue
<220> FEATURE:
<221> NAME/KEY: VARIANT
<222> LOCATION: 7
<223> OTHER INFORMATION: Xaa = a residue that preserves hydrogen bonding
      with CtBP
<220> FEATURE:
<221> NAME/KEY: VARIANT
<222> LOCATION: 8
<223> OTHER INFORMATION: Xaa = a hydrophobic residue
<220> FEATURE:
<221> NAME/KEY: VARIANT
<222> LOCATION: 9
<223> OTHER INFORMATION: Xaa = a residue that preserves hydrogen bonding
      with CtBP
<220> FEATURE:
<221> NAME/KEY: VARIANT
<222> LOCATION: 10
<223> OTHER INFORMATION: Xaa = C, M, L, K, V or T
<220> FEATURE:
<221> NAME/KEY: VARIANT
<222> LOCATION: 11
<223> OTHER INFORMATION: Xaa = K, A or R
<220> FEATURE:
<221> NAME/KEY: VARIANT
<222> LOCATION: 12
<223> OTHER INFORMATION: Xaa = R, T, H, P, K or C
<220> FEATURE:
<221> NAME/KEY: VARIANT
<222> LOCATION: 13
<223> OTHER INFORMATION: Xaa = P, S, G, R or L
<220> FEATURE:
<221> NAME/KEY: VARIANT
<222> LOCATION: 14
<223> OTHER INFORMATION: Xaa = R, K, P, T, L or S

<400> SEQUENCE: 130

Xaa Xaa Xaa Xaa Pro Xaa Xaa Xaa Xaa Xaa Xaa Xaa Xaa Xaa
 1               5                  10

<210> SEQ ID NO 131
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = E, G, P, A or V
<220> FEATURE:
<221> NAME/KEY: VARIANT
<222> LOCATION: 2
<223> OTHER INFORMATION: Xaa = P, Q, G, S, T, V or M
<220> FEATURE:
<221> NAME/KEY: VARIANT
<222> LOCATION: 3
<223> OTHER INFORMATION: Xaa = G, T, D, E or N
```

```
<220> FEATURE:
<221> NAME/KEY: VARIANT
<222> LOCATION: 4
<223> OTHER INFORMATION: Xaa = Q, V, E or G
<220> FEATURE:
<221> NAME/KEY: VARIANT
<222> LOCATION: 6
<223> OTHER INFORMATION: Xaa = L, V, I, M, Q or E
<220> FEATURE:
<221> NAME/KEY: VARIANT
<222> LOCATION: 7
<223> OTHER INFORMATION: Xaa = D or N
<220> FEATURE:
<221> NAME/KEY: VARIANT
<222> LOCATION: 8
<223> OTHER INFORMATION: Xaa = L or I
<220> FEATURE:
<221> NAME/KEY: VARIANT
<222> LOCATION: 9
<223> OTHER INFORMATION: Xaa = S, C, T, V or A
<220> FEATURE:
<221> NAME/KEY: VARIANT
<222> LOCATION: 10
<223> OTHER INFORMATION: Xaa = C, M, L, K, V or T
<220> FEATURE:
<221> NAME/KEY: VARIANT
<222> LOCATION: 11
<223> OTHER INFORMATION: Xaa = K, A or R
<220> FEATURE:
<221> NAME/KEY: VARIANT
<222> LOCATION: 12
<223> OTHER INFORMATION: Xaa = R, T, H, P, K or C
<220> FEATURE:
<221> NAME/KEY: VARIANT
<222> LOCATION: 13
<223> OTHER INFORMATION: Xaa = P, S, G, R or L
<220> FEATURE:
<221> NAME/KEY: VARIANT
<222> LOCATION: 14
<223> OTHER INFORMATION: Xaa = R, K, P, T, L or S

<400> SEQUENCE: 131

Xaa Xaa Xaa Xaa Pro Xaa Xaa Xaa Xaa Xaa Xaa Xaa Xaa Xaa
 1               5                  10

<210> SEQ ID NO 132
<211> LENGTH: 14
<212> TYPE: PRT
<213> ORGANISM: Artificial Sequence
<220> FEATURE:
<223> OTHER INFORMATION: Synthetic Construct

<400> SEQUENCE: 132

Glu Gln Thr Val Pro Val Asp Leu Ser Val Ala Arg Pro Arg
 1               5                  10

<210> SEQ ID NO 133
<211> LENGTH: 14
<212> TYPE: PRT
<213> ORGANISM: Artificial Sequence
<220> FEATURE:
<223> OTHER INFORMATION: Synthetic Construct

<400> SEQUENCE: 133

Gly Gly Asp Gly Pro Leu Asp Leu Cys Cys Arg Lys Arg Pro
 1               5                  10

<210> SEQ ID NO 134
<211> LENGTH: 14
<212> TYPE: PRT
<213> ORGANISM: Artificial Sequence
<220> FEATURE:
<223> OTHER INFORMATION: Synthetic Construct
```

<400> SEQUENCE: 134

Pro Thr Asp Glu Pro Leu Asn Leu Ser Leu Lys Arg Pro Arg
1               5                   10

<210> SEQ ID NO 135
<211> LENGTH: 14
<212> TYPE: PRT
<213> ORGANISM: Artificial Sequence
<220> FEATURE:
<223> OTHER INFORMATION: Synthetic Construct

<400> SEQUENCE: 135

Glu Pro Gly Gln Pro Leu Ser Leu Ser Cys Lys Arg Pro Arg
1               5                   10

<210> SEQ ID NO 136
<211> LENGTH: 243
<212> TYPE: PRT
<213> ORGANISM: Human adenovirus C

<400> SEQUENCE: 136

Met Arg His Ile Ile Cys His Gly Gly Val Ile Thr Glu Glu Met Ala
1               5                   10                  15

Ala Ser Leu Leu Asp Gln Leu Ile Glu Val Leu Ala Asp Asn Leu
            20                  25                  30

Pro Pro Pro Ser His Phe Glu Pro Thr Leu His Glu Leu Tyr Asp
        35                  40                  45

Leu Asp Val Thr Ala Pro Glu Asp Pro Asn Glu Glu Ala Val Ser Gln
50                  55                  60

Ile Phe Pro Glu Ser Val Met Leu Ala Val Gln Glu Gly Ile Asp Leu
65                  70                  75                  80

Phe Thr Phe Pro Pro Ala Pro Gly Ser Pro Glu Pro Pro His Leu Ser
                85                  90                  95

Arg Gln Pro Glu Gln Pro Glu Gln Arg Ala Leu Gly Pro Val Ser Met
            100                 105                 110

Pro Asn Leu Val Pro Glu Val Ile Asp Leu Thr Cys His Glu Ala Gly
        115                 120                 125

Phe Pro Pro Ser Asp Asp Glu Asp Glu Glu Gly Pro Val Ser Glu Pro
130                 135                 140

Glu Pro Glu Pro Glu Pro Glu Pro Ala Arg Pro Thr Arg Arg
145                 150                 155                 160

Pro Lys Leu Val Pro Ala Ile Leu Arg Arg Pro Thr Ser Pro Val Ser
                165                 170                 175

Arg Glu Cys Asn Ser Ser Thr Asp Ser Cys Asp Ser Gly Pro Ser Asn
            180                 185                 190

Thr Pro Pro Glu Ile His Pro Val Val Pro Leu Cys Pro Ile Lys Pro
        195                 200                 205

Val Ala Val Arg Val Gly Gly Arg Arg Gln Ala Val Glu Cys Ile Glu
    210                 215                 220

Asp Leu Leu Asn Glu Ser Gly Gln Pro Leu Asp Leu Ser Cys Lys Arg
225                 230                 235                 240

Pro Arg Pro

<210> SEQ ID NO 137
<211> LENGTH: 31
<212> TYPE: PRT
<213> ORGANISM: Artificial Sequence

```
<220> FEATURE:
<223> OTHER INFORMATION: Synthetic Construct

<400> SEQUENCE: 137

Gly Arg Lys Lys Arg Arg Gln Arg Arg Pro Pro Gln Gly Gly Glu
 1               5                  10                  15

Gln Thr Val Pro Val Asp Leu Ser Val Ala Arg Pro Arg Gly Leu
             20                  25                  30

<210> SEQ ID NO 138
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Q, V, E or G
<220> FEATURE:
<221> NAME/KEY: VARIANT
<222> LOCATION: 3
<223> OTHER INFORMATION: Xaa = a hydrophobic residue
<220> FEATURE:
<221> NAME/KEY: VARIANT
<222> LOCATION: 4
<223> OTHER INFORMATION: Xaa = a residue that preserves hydrogen bonding
      with CtBP
<220> FEATURE:
<221> NAME/KEY: VARIANT
<222> LOCATION: 5
<223> OTHER INFORMATION: Xaa = a hydrophobic residue
<220> FEATURE:
<221> NAME/KEY: VARIANT
<222> LOCATION: 6
<223> OTHER INFORMATION: Xaa = a residue that preserves hydrogen bonding
      with CtBP

<400> SEQUENCE: 138

Xaa Pro Xaa Xaa Xaa Xaa
 1               5

<210> SEQ ID NO 139
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Q, V, E or G
<220> FEATURE:
<221> NAME/KEY: VARIANT
<222> LOCATION: 3
<223> OTHER INFORMATION: Xaa = L, V, I, M, Q or E
<220> FEATURE:
<221> NAME/KEY: VARIANT
<222> LOCATION: 4
<223> OTHER INFORMATION: Xaa = D or N
<220> FEATURE:
<221> NAME/KEY: VARIANT
<222> LOCATION: 5
<223> OTHER INFORMATION: Xaa = L or I
<220> FEATURE:
<221> NAME/KEY: VARIANT
<222> LOCATION: 6
<223> OTHER INFORMATION: Xaa = S, C, T, V or A

<400> SEQUENCE: 139

Xaa Pro Xaa Xaa Xaa Xaa
 1               5
```

```
<210> SEQ ID NO 140
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = G, T, D, E or N
<220> FEATURE:
<221> NAME/KEY: VARIANT
<222> LOCATION: 2
<223> OTHER INFORMATION: Xaa = Q, V, E or G
<220> FEATURE:
<221> NAME/KEY: VARIANT
<222> LOCATION: 4
<223> OTHER INFORMATION: Xaa = a hydrophobic residue
<220> FEATURE:
<221> NAME/KEY: VARIANT
<222> LOCATION: 5
<223> OTHER INFORMATION: Xaa = a residue that preserves hydrogen bonding
      with CtBP
<220> FEATURE:
<221> NAME/KEY: VARIANT
<222> LOCATION: 6
<223> OTHER INFORMATION: Xaa = a hydrophobic residue
<220> FEATURE:
<221> NAME/KEY: VARIANT
<222> LOCATION: 7
<223> OTHER INFORMATION: Xaa = a residue that preserves hydrogen bonding
      with CtBP

<400> SEQUENCE: 140

Xaa Xaa Pro Xaa Xaa Xaa Xaa
 1               5

<210> SEQ ID NO 141
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = G, T, D, E or N
<220> FEATURE:
<221> NAME/KEY: VARIANT
<222> LOCATION: 2
<223> OTHER INFORMATION: Xaa = Q, V, E or G
<220> FEATURE:
<221> NAME/KEY: VARIANT
<222> LOCATION: 4
<223> OTHER INFORMATION: Xaa = L, V, I, M, Q or E
<220> FEATURE:
<221> NAME/KEY: VARIANT
<222> LOCATION: 5
<223> OTHER INFORMATION: Xaa = D or N
<220> FEATURE:
<221> NAME/KEY: VARIANT
<222> LOCATION: 6
<223> OTHER INFORMATION: Xaa = L or I
<220> FEATURE:
<221> NAME/KEY: VARIANT
<222> LOCATION: 7
<223> OTHER INFORMATION: Xaa = S, C, T, V or A

<400> SEQUENCE: 141

Xaa Xaa Pro Xaa Xaa Xaa Xaa
 1               5

<210> SEQ ID NO 142
<211> LENGTH: 8
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = P, Q, G, S, T, V or M
<220> FEATURE:
<221> NAME/KEY: VARIANT
<222> LOCATION: 2
<223> OTHER INFORMATION: Xaa = G, T, D, E or N
<220> FEATURE:
<221> NAME/KEY: VARIANT
<222> LOCATION: 3
<223> OTHER INFORMATION: Xaa = Q, V, E or G
<220> FEATURE:
<221> NAME/KEY: VARIANT
<222> LOCATION: 5
<223> OTHER INFORMATION: Xaa = a hydrophobic residue
<220> FEATURE:
<221> NAME/KEY: VARIANT
<222> LOCATION: 6
<223> OTHER INFORMATION: Xaa = a residue that preserves hydrogen bonding
      with CtBP
<220> FEATURE:
<221> NAME/KEY: VARIANT
<222> LOCATION: 7
<223> OTHER INFORMATION: Xaa = a hydrophobic residue
<220> FEATURE:
<221> NAME/KEY: VARIANT
<222> LOCATION: 8
<223> OTHER INFORMATION: Xaa = a residue that preserves hydrogen bonding
      with CtBP

<400> SEQUENCE: 142

Xaa Xaa Xaa Pro Xaa Xaa Xaa Xaa
 1               5

<210> SEQ ID NO 143
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = P, Q, G, S, T, V or M
<220> FEATURE:
<221> NAME/KEY: VARIANT
<222> LOCATION: 2
<223> OTHER INFORMATION: Xaa = G, T, D, E or N
<220> FEATURE:
<221> NAME/KEY: VARIANT
<222> LOCATION: 3
<223> OTHER INFORMATION: Xaa = Q, V, E or G
<220> FEATURE:
<221> NAME/KEY: VARIANT
<222> LOCATION: 5
<223> OTHER INFORMATION: Xaa = L, V, I, M, Q or E
<220> FEATURE:
<221> NAME/KEY: VARIANT
<222> LOCATION: 6
<223> OTHER INFORMATION: Xaa = D or N
<220> FEATURE:
<221> NAME/KEY: VARIANT
<222> LOCATION: 7
<223> OTHER INFORMATION: Xaa = L or I
<220> FEATURE:
<221> NAME/KEY: VARIANT
<222> LOCATION: 8
<223> OTHER INFORMATION: Xaa = S, C, T, V or A

<400> SEQUENCE: 143

Xaa Xaa Xaa Pro Xaa Xaa Xaa Xaa
```

-continued

```
  1               5

<210> SEQ ID NO 144
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = E, G, P, A or V
<220> FEATURE:
<221> NAME/KEY: VARIANT
<222> LOCATION: 2
<223> OTHER INFORMATION: Xaa = P, Q, G, S, T, V or M
<220> FEATURE:
<221> NAME/KEY: VARIANT
<222> LOCATION: 3
<223> OTHER INFORMATION: Xaa = G, T, D, E or N
<220> FEATURE:
<221> NAME/KEY: VARIANT
<222> LOCATION: 4
<223> OTHER INFORMATION: Xaa = Q, V, E or G
<220> FEATURE:
<221> NAME/KEY: VARIANT
<222> LOCATION: 6
<223> OTHER INFORMATION: Xaa = a hydrophobic residue
<220> FEATURE:
<221> NAME/KEY: VARIANT
<222> LOCATION: 7
<223> OTHER INFORMATION: Xaa = a residue that preserves hydrogen bonding
      with CtBP
<220> FEATURE:
<221> NAME/KEY: VARIANT
<222> LOCATION: 8
<223> OTHER INFORMATION: Xaa = a hydrophobic residue
<220> FEATURE:
<221> NAME/KEY: VARIANT
<222> LOCATION: 9
<223> OTHER INFORMATION: Xaa = a residue that preserves hydrogen bonding
      with CtBP

<400> SEQUENCE: 144

Xaa Xaa Xaa Xaa Pro Xaa Xaa Xaa Xaa
  1               5

<210> SEQ ID NO 145
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = E, G, P, A or V
<220> FEATURE:
<221> NAME/KEY: VARIANT
<222> LOCATION: 2
<223> OTHER INFORMATION: Xaa = P, Q, G, S, T, V or M
<220> FEATURE:
<221> NAME/KEY: VARIANT
<222> LOCATION: 3
<223> OTHER INFORMATION: Xaa = G, T, D, E or N
<220> FEATURE:
<221> NAME/KEY: VARIANT
<222> LOCATION: 4
<223> OTHER INFORMATION: Xaa = Q, V, E or G
<220> FEATURE:
<221> NAME/KEY: VARIANT
<222> LOCATION: 6
<223> OTHER INFORMATION: Xaa = L, V, I, M, Q or E
<220> FEATURE:
<221> NAME/KEY: VARIANT
<222> LOCATION: 7
```

-continued

```
<223> OTHER INFORMATION: Xaa = D or N
<220> FEATURE:
<221> NAME/KEY: VARIANT
<222> LOCATION: 8
<223> OTHER INFORMATION: Xaa = L or I
<220> FEATURE:
<221> NAME/KEY: VARIANT
<222> LOCATION: 9
<223> OTHER INFORMATION: Xaa = S, C, T, V or A

<400> SEQUENCE: 145

Xaa Xaa Xaa Xaa Pro Xaa Xaa Xaa Xaa
 1               5

<210> SEQ ID NO 146
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = a hydrophobic residue
<220> FEATURE:
<221> NAME/KEY: VARIANT
<222> LOCATION: 3
<223> OTHER INFORMATION: Xaa = a residue that preserves hydrogen bonding
      with CtBP
<220> FEATURE:
<221> NAME/KEY: VARIANT
<222> LOCATION: 4
<223> OTHER INFORMATION: Xaa = a hydrophobic residue
<220> FEATURE:
<221> NAME/KEY: VARIANT
<222> LOCATION: 5
<223> OTHER INFORMATION: Xaa = a residue that preserves hydrogen bonding
      with CtBP
<220> FEATURE:
<221> NAME/KEY: VARIANT
<222> LOCATION: 6
<223> OTHER INFORMATION: Xaa = C, M, L, K, V or T

<400> SEQUENCE: 146

Pro Xaa Xaa Xaa Xaa Xaa
 1               5

<210> SEQ ID NO 147
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = L, V, I, M, Q or E
<220> FEATURE:
<221> NAME/KEY: VARIANT
<222> LOCATION: 3
<223> OTHER INFORMATION: Xaa = D or N
<220> FEATURE:
<221> NAME/KEY: VARIANT
<222> LOCATION: 4
<223> OTHER INFORMATION: Xaa = L or I
<220> FEATURE:
<221> NAME/KEY: VARIANT
<222> LOCATION: 5
<223> OTHER INFORMATION: Xaa = S, C, T, V or A
<220> FEATURE:
<221> NAME/KEY: VARIANT
<222> LOCATION: 6
<223> OTHER INFORMATION: Xaa = C, M, L, K, V or T

<400> SEQUENCE: 147
```

Pro Xaa Xaa Xaa Xaa Xaa
1               5

<210> SEQ ID NO 148
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = a hydrophobic residue
<220> FEATURE:
<221> NAME/KEY: VARIANT
<222> LOCATION: 3
<223> OTHER INFORMATION: Xaa = a residue that preserves hydrogen bonding
      with CtBP
<220> FEATURE:
<221> NAME/KEY: VARIANT
<222> LOCATION: 4
<223> OTHER INFORMATION: Xaa = a hydrophobic residue
<220> FEATURE:
<221> NAME/KEY: VARIANT
<222> LOCATION: 5
<223> OTHER INFORMATION: Xaa = a residue that preserves hydrogen bonding
      with CtBP
<220> FEATURE:
<221> NAME/KEY: VARIANT
<222> LOCATION: 6
<223> OTHER INFORMATION: Xaa = C, M, L, K, V or T
<220> FEATURE:
<221> NAME/KEY: VARIANT
<222> LOCATION: 7
<223> OTHER INFORMATION: Xaa = K, A or R

<400> SEQUENCE: 148

Pro Xaa Xaa Xaa Xaa Xaa Xaa
1               5

<210> SEQ ID NO 149
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = L, V, I, M, Q or E
<220> FEATURE:
<221> NAME/KEY: VARIANT
<222> LOCATION: 3
<223> OTHER INFORMATION: Xaa = D or N
<220> FEATURE:
<221> NAME/KEY: VARIANT
<222> LOCATION: 4
<223> OTHER INFORMATION: Xaa = L or I
<220> FEATURE:
<221> NAME/KEY: VARIANT
<222> LOCATION: 5
<223> OTHER INFORMATION: Xaa = S, C, T, V or A
<220> FEATURE:
<221> NAME/KEY: VARIANT
<222> LOCATION: 6
<223> OTHER INFORMATION: Xaa = C, M, L, K, V or T
<220> FEATURE:
<221> NAME/KEY: VARIANT
<222> LOCATION: 7
<223> OTHER INFORMATION: Xaa = K, A or R

<400> SEQUENCE: 149

Pro Xaa Xaa Xaa Xaa Xaa Xaa
1               5

```
<210> SEQ ID NO 150
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = a hydrophobic residue
<220> FEATURE:
<221> NAME/KEY: VARIANT
<222> LOCATION: 3
<223> OTHER INFORMATION: Xaa = a residue that preserves hydrogen bonding
      with CtBP
<220> FEATURE:
<221> NAME/KEY: VARIANT
<222> LOCATION: 4
<223> OTHER INFORMATION: Xaa = a hydrophobic residue
<220> FEATURE:
<221> NAME/KEY: VARIANT
<222> LOCATION: 5
<223> OTHER INFORMATION: Xaa = a residue that preserves hydrogen bonding
      with CtBP
<220> FEATURE:
<221> NAME/KEY: VARIANT
<222> LOCATION: 6
<223> OTHER INFORMATION: Xaa = C, M, L, K, V or T
<220> FEATURE:
<221> NAME/KEY: VARIANT
<222> LOCATION: 7
<223> OTHER INFORMATION: Xaa = K, A or R
<220> FEATURE:
<221> NAME/KEY: VARIANT
<222> LOCATION: 8
<223> OTHER INFORMATION: Xaa = R, T, H, P, K or C

<400> SEQUENCE: 150

Pro Xaa Xaa Xaa Xaa Xaa Xaa Xaa
 1               5

<210> SEQ ID NO 151
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = L, V, I, M, Q or E
<220> FEATURE:
<221> NAME/KEY: VARIANT
<222> LOCATION: 3
<223> OTHER INFORMATION: Xaa = D or N
<220> FEATURE:
<221> NAME/KEY: VARIANT
<222> LOCATION: 4
<223> OTHER INFORMATION: Xaa = L or I
<220> FEATURE:
<221> NAME/KEY: VARIANT
<222> LOCATION: 5
<223> OTHER INFORMATION: Xaa = S, C, T, V or A
<220> FEATURE:
<221> NAME/KEY: VARIANT
<222> LOCATION: 6
<223> OTHER INFORMATION: Xaa = C, M, L, K, V or T
<220> FEATURE:
<221> NAME/KEY: VARIANT
<222> LOCATION: 7
<223> OTHER INFORMATION: Xaa = K, A or R
<220> FEATURE:
<221> NAME/KEY: VARIANT
<222> LOCATION: 8
<223> OTHER INFORMATION: Xaa = R, T, H, P, K or C
```

<400> SEQUENCE: 151

Pro Xaa Xaa Xaa Xaa Xaa Xaa Xaa
 1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = a hydrophobic residue
<220> FEATURE:
<221> NAME/KEY: VARIANT
<222> LOCATION: 3
<223> OTHER INFORMATION: Xaa = a residue that preserves hydrogen bonding
      with CtBP
<220> FEATURE:
<221> NAME/KEY: VARIANT
<222> LOCATION: 4
<223> OTHER INFORMATION: Xaa = a hydrophobic residue
<220> FEATURE:
<221> NAME/KEY: VARIANT
<222> LOCATION: 5
<223> OTHER INFORMATION: Xaa = a residue that preserves hydrogen bonding
      with CtBP
<220> FEATURE:
<221> NAME/KEY: VARIANT
<222> LOCATION: 6
<223> OTHER INFORMATION: Xaa = C, M, L, K, V or T
<220> FEATURE:
<221> NAME/KEY: VARIANT
<222> LOCATION: 7
<223> OTHER INFORMATION: Xaa = K, A or R
<220> FEATURE:
<221> NAME/KEY: VARIANT
<222> LOCATION: 8
<223> OTHER INFORMATION: Xaa = R, T, H, P, K or C
<220> FEATURE:
<221> NAME/KEY: VARIANT
<222> LOCATION: 9
<223> OTHER INFORMATION: Xaa = P, S, G, R or L

<400> SEQUENCE: 152

Pro Xaa Xaa Xaa Xaa Xaa Xaa Xaa Xaa
 1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = L, V, I, M, Q or E
<220> FEATURE:
<221> NAME/KEY: VARIANT
<222> LOCATION: 3
<223> OTHER INFORMATION: Xaa = D or N
<220> FEATURE:
<221> NAME/KEY: VARIANT
<222> LOCATION: 4
<223> OTHER INFORMATION: Xaa = L or I
<220> FEATURE:
<221> NAME/KEY: VARIANT
<222> LOCATION: 5
<223> OTHER INFORMATION: Xaa = S, C, T, V or A
<220> FEATURE:
<221> NAME/KEY: VARIANT
<222> LOCATION: 6

```
<223> OTHER INFORMATION: Xaa = C, M, L, K, V or T
<220> FEATURE:
<221> NAME/KEY: VARIANT
<222> LOCATION: 7
<223> OTHER INFORMATION: Xaa = K, A or R
<220> FEATURE:
<221> NAME/KEY: VARIANT
<222> LOCATION: 8
<223> OTHER INFORMATION: Xaa = R, T, H, P, K or C
<220> FEATURE:
<221> NAME/KEY: VARIANT
<222> LOCATION: 9
<223> OTHER INFORMATION: Xaa = P, S, G, R or L

<400> SEQUENCE: 153

Pro Xaa Xaa Xaa Xaa Xaa Xaa Xaa Xaa
 1               5

<210> SEQ ID NO 154
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = a hydrophobic residue
<220> FEATURE:
<221> NAME/KEY: VARIANT
<222> LOCATION: 3
<223> OTHER INFORMATION: Xaa = a residue that preserves hydrogen bonding
      with CtBP
<220> FEATURE:
<221> NAME/KEY: VARIANT
<222> LOCATION: 4
<223> OTHER INFORMATION: Xaa = a hydrophobic residue
<220> FEATURE:
<221> NAME/KEY: VARIANT
<222> LOCATION: 5
<223> OTHER INFORMATION: Xaa = a residue that preserves hydrogen bonding
      with CtBP
<220> FEATURE:
<221> NAME/KEY: VARIANT
<222> LOCATION: 6
<223> OTHER INFORMATION: Xaa = C, M, L, K, V or T
<220> FEATURE:
<221> NAME/KEY: VARIANT
<222> LOCATION: 7
<223> OTHER INFORMATION: Xaa = K, A or R
<220> FEATURE:
<221> NAME/KEY: VARIANT
<222> LOCATION: 8
<223> OTHER INFORMATION: Xaa = R, T, H, P, K or C
<220> FEATURE:
<221> NAME/KEY: VARIANT
<222> LOCATION: 9
<223> OTHER INFORMATION: Xaa = P, S, G, R or L
<220> FEATURE:
<221> NAME/KEY: VARIANT
<222> LOCATION: 10
<223> OTHER INFORMATION: Xaa = R, K, P, T, L or S

<400> SEQUENCE: 154

Pro Xaa Xaa Xaa Xaa Xaa Xaa Xaa Xaa Xaa
 1               5                  10

<210> SEQ ID NO 155
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
```

```
<222> LOCATION: 2
<223> OTHER INFORMATION: Xaa = L, V, I, M, Q or E
<220> FEATURE:
<221> NAME/KEY: VARIANT
<222> LOCATION: 3
<223> OTHER INFORMATION: Xaa = D or N
<220> FEATURE:
<221> NAME/KEY: VARIANT
<222> LOCATION: 4
<223> OTHER INFORMATION: Xaa = L or I
<220> FEATURE:
<221> NAME/KEY: VARIANT
<222> LOCATION: 5
<223> OTHER INFORMATION: Xaa = S, C, T, V or A
<220> FEATURE:
<221> NAME/KEY: VARIANT
<222> LOCATION: 6
<223> OTHER INFORMATION: Xaa = C, M, L, K, V or T
<220> FEATURE:
<221> NAME/KEY: VARIANT
<222> LOCATION: 7
<223> OTHER INFORMATION: Xaa = K, A or R
<220> FEATURE:
<221> NAME/KEY: VARIANT
<222> LOCATION: 8
<223> OTHER INFORMATION: Xaa = R, T, H, P, K or C
<220> FEATURE:
<221> NAME/KEY: VARIANT
<222> LOCATION: 9
<223> OTHER INFORMATION: Xaa = P, S, G, R or L
<220> FEATURE:
<221> NAME/KEY: VARIANT
<222> LOCATION: 10
<223> OTHER INFORMATION: Xaa = R, K, P, T, L or S

<400> SEQUENCE: 155

Pro Xaa Xaa Xaa Xaa Xaa Xaa Xaa Xaa Xaa
 1               5                  10

<210> SEQ ID NO 156
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Q, V, E or G
<220> FEATURE:
<221> NAME/KEY: VARIANT
<222> LOCATION: 3
<223> OTHER INFORMATION: Xaa = a hydrophobic residue
<220> FEATURE:
<221> NAME/KEY: VARIANT
<222> LOCATION: 4
<223> OTHER INFORMATION: Xaa = a residue that preserves hydrogen bonding
      with CtBP
<220> FEATURE:
<221> NAME/KEY: VARIANT
<222> LOCATION: 5
<223> OTHER INFORMATION: Xaa = a hydrophobic residue
<220> FEATURE:
<221> NAME/KEY: VARIANT
<222> LOCATION: 6
<223> OTHER INFORMATION: Xaa = a residue that preserves hydrogen bonding
      with CtBP
<220> FEATURE:
<221> NAME/KEY: VARIANT
<222> LOCATION: 7
<223> OTHER INFORMATION: Xaa = C, M, L, K, V or T

<400> SEQUENCE: 156

Xaa Pro Xaa Xaa Xaa Xaa Xaa
 1               5
```

```
<210> SEQ ID NO 157
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Q, V, E or G
<220> FEATURE:
<221> NAME/KEY: VARIANT
<222> LOCATION: 3
<223> OTHER INFORMATION: Xaa = L, V, I, M, Q or E
<220> FEATURE:
<221> NAME/KEY: VARIANT
<222> LOCATION: 4
<223> OTHER INFORMATION: Xaa = D or N
<220> FEATURE:
<221> NAME/KEY: VARIANT
<222> LOCATION: 5
<223> OTHER INFORMATION: Xaa = L or I
<220> FEATURE:
<221> NAME/KEY: VARIANT
<222> LOCATION: 6
<223> OTHER INFORMATION: Xaa = S, C, T, V or A
<220> FEATURE:
<221> NAME/KEY: VARIANT
<222> LOCATION: 7
<223> OTHER INFORMATION: Xaa = C, M, L, K, V or T

<400> SEQUENCE: 157

Xaa Pro Xaa Xaa Xaa Xaa Xaa
 1               5

<210> SEQ ID NO 158
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = G, T, D, E or N
<220> FEATURE:
<221> NAME/KEY: VARIANT
<222> LOCATION: 2
<223> OTHER INFORMATION: Xaa = Q, V, E or G
<220> FEATURE:
<221> NAME/KEY: VARIANT
<222> LOCATION: 4
<223> OTHER INFORMATION: Xaa = a hydrophobic residue
<220> FEATURE:
<221> NAME/KEY: VARIANT
<222> LOCATION: 5
<223> OTHER INFORMATION: Xaa = a residue that preserves hydrogen bonding
      with CtBP
<220> FEATURE:
<221> NAME/KEY: VARIANT
<222> LOCATION: 6
<223> OTHER INFORMATION: Xaa = a hydrophobic residue
<220> FEATURE:
<221> NAME/KEY: VARIANT
<222> LOCATION: 7
<223> OTHER INFORMATION: Xaa = a residue that preserves hydrogen bonding
      with CtBP
<220> FEATURE:
<221> NAME/KEY: VARIANT
<222> LOCATION: 8
<223> OTHER INFORMATION: Xaa = C, M, L, K, V or T
<220> FEATURE:
<221> NAME/KEY: VARIANT
<222> LOCATION: 9
<223> OTHER INFORMATION: Xaa = K, A or R
```

```
<400> SEQUENCE: 158

Xaa Xaa Pro Xaa Xaa Xaa Xaa Xaa Xaa
 1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = G, T, D, E or N
<220> FEATURE:
<221> NAME/KEY: VARIANT
<222> LOCATION: 2
<223> OTHER INFORMATION: Xaa = Q, V, E or G
<220> FEATURE:
<221> NAME/KEY: VARIANT
<222> LOCATION: 4
<223> OTHER INFORMATION: Xaa = L, V, I, M, Q or E
<220> FEATURE:
<221> NAME/KEY: VARIANT
<222> LOCATION: 5
<223> OTHER INFORMATION: Xaa = D or N
<220> FEATURE:
<221> NAME/KEY: VARIANT
<222> LOCATION: 6
<223> OTHER INFORMATION: Xaa = L or I
<220> FEATURE:
<221> NAME/KEY: VARIANT
<222> LOCATION: 7
<223> OTHER INFORMATION: Xaa = S, C, T, V or A
<220> FEATURE:
<221> NAME/KEY: VARIANT
<222> LOCATION: 8
<223> OTHER INFORMATION: Xaa = C, M, L, K, V or T
<220> FEATURE:
<221> NAME/KEY: VARIANT
<222> LOCATION: 9
<223> OTHER INFORMATION: Xaa = K, A or R

<400> SEQUENCE: 159

Xaa Xaa Pro Xaa Xaa Xaa Xaa Xaa Xaa
 1               5

<210> SEQ ID NO 160
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = P, Q, G, S, T, V or M
<220> FEATURE:
<221> NAME/KEY: VARIANT
<222> LOCATION: 2
<223> OTHER INFORMATION: Xaa = G, T, D, E or N
<220> FEATURE:
<221> NAME/KEY: VARIANT
<222> LOCATION: 3
<223> OTHER INFORMATION: Xaa = Q, V, E or G
<220> FEATURE:
<221> NAME/KEY: VARIANT
<222> LOCATION: 5
<223> OTHER INFORMATION: Xaa = a hydrophobic residue
<220> FEATURE:
<221> NAME/KEY: VARIANT
<222> LOCATION: 6
<223> OTHER INFORMATION: Xaa = a residue that preserves hydrogen bonding
      with CtBP
<220> FEATURE:
```

```
<221> NAME/KEY: VARIANT
<222> LOCATION: 7
<223> OTHER INFORMATION: Xaa = a hydrophobic residue
<220> FEATURE:
<221> NAME/KEY: VARIANT
<222> LOCATION: 8
<223> OTHER INFORMATION: Xaa = a residue that preserves hydrogen bonding
      with CtBP
<220> FEATURE:
<221> NAME/KEY: VARIANT
<222> LOCATION: 9
<223> OTHER INFORMATION: Xaa = C, M, L, K, V or T
<220> FEATURE:
<221> NAME/KEY: VARIANT
<222> LOCATION: 10
<223> OTHER INFORMATION: Xaa = K, A or R
<220> FEATURE:
<221> NAME/KEY: VARIANT
<222> LOCATION: 11
<223> OTHER INFORMATION: Xaa = R, T, H, P, K or C

<400> SEQUENCE: 160

Xaa Xaa Xaa Pro Xaa Xaa Xaa Xaa Xaa Xaa Xaa
 1               5                  10

<210> SEQ ID NO 161
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = P, Q, G, S, T, V or M
<220> FEATURE:
<221> NAME/KEY: VARIANT
<222> LOCATION: 2
<223> OTHER INFORMATION: Xaa = G, T, D, E or N
<220> FEATURE:
<221> NAME/KEY: VARIANT
<222> LOCATION: 3
<223> OTHER INFORMATION: Xaa = Q, V, E or G
<220> FEATURE:
<221> NAME/KEY: VARIANT
<222> LOCATION: 5
<223> OTHER INFORMATION: Xaa = L, V, I, M, Q or E
<220> FEATURE:
<221> NAME/KEY: VARIANT
<222> LOCATION: 6
<223> OTHER INFORMATION: Xaa = D or N
<220> FEATURE:
<221> NAME/KEY: VARIANT
<222> LOCATION: 7
<223> OTHER INFORMATION: Xaa = L or I
<220> FEATURE:
<221> NAME/KEY: VARIANT
<222> LOCATION: 8
<223> OTHER INFORMATION: Xaa = S, C, T, V or A
<220> FEATURE:
<221> NAME/KEY: VARIANT
<222> LOCATION: 9
<223> OTHER INFORMATION: Xaa = C, M, L, K, V or T
<220> FEATURE:
<221> NAME/KEY: VARIANT
<222> LOCATION: 10
<223> OTHER INFORMATION: Xaa = K, A or R
<220> FEATURE:
<221> NAME/KEY: VARIANT
<222> LOCATION: 11
<223> OTHER INFORMATION: Xaa = R, T, H, P, K or C

<400> SEQUENCE: 161

Xaa Xaa Xaa Pro Xaa Xaa Xaa Xaa Xaa Xaa Xaa
 1               5                  10
```

```
<210> SEQ ID NO 162
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = E, G, P, A or V
<220> FEATURE:
<221> NAME/KEY: VARIANT
<222> LOCATION: 2
<223> OTHER INFORMATION: Xaa = P, Q, G, S, T, V or M
<220> FEATURE:
<221> NAME/KEY: VARIANT
<222> LOCATION: 3
<223> OTHER INFORMATION: Xaa = G, T, D, E or N
<220> FEATURE:
<221> NAME/KEY: VARIANT
<222> LOCATION: 4
<223> OTHER INFORMATION: Xaa = Q, V, E or G
<220> FEATURE:
<221> NAME/KEY: VARIANT
<222> LOCATION: 6
<223> OTHER INFORMATION: Xaa = a hydrophobic residue
<220> FEATURE:
<221> NAME/KEY: VARIANT
<222> LOCATION: 7
<223> OTHER INFORMATION: Xaa = a residue that preserves hydrogen
      bonding with CtBP
<220> FEATURE:
<221> NAME/KEY: VARIANT
<222> LOCATION: 8
<223> OTHER INFORMATION: Xaa = a hydrophobic residue
<220> FEATURE:
<221> NAME/KEY: VARIANT
<222> LOCATION: 9
<223> OTHER INFORMATION: Xaa = a residue that preserves hydrogen
      bonding with CtBP
<220> FEATURE:
<221> NAME/KEY: VARIANT
<222> LOCATION: 10
<223> OTHER INFORMATION: Xaa = C, M, L, K, V or T
<220> FEATURE:
<221> NAME/KEY: VARIANT
<222> LOCATION: 11
<223> OTHER INFORMATION: Xaa = K, A or R
<220> FEATURE:
<221> NAME/KEY: VARIANT
<222> LOCATION: 12
<223> OTHER INFORMATION: Xaa = R, T, H, P, K or C
<220> FEATURE:
<221> NAME/KEY: VARIANT
<222> LOCATION: 13
<223> OTHER INFORMATION: Xaa = P, S, G, R or L

<400> SEQUENCE: 162

Xaa Xaa Xaa Xaa Pro Xaa Xaa Xaa Xaa Xaa Xaa Xaa Xaa
 1               5                  10

<210> SEQ ID NO 163
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = E, G, P, A or V
<220> FEATURE:
<221> NAME/KEY: VARIANT
<222> LOCATION: 2
<223> OTHER INFORMATION: Xaa = P, Q, G, S, T, V or M
<220> FEATURE:
```

```
<221> NAME/KEY: VARIANT
<222> LOCATION: 3
<223> OTHER INFORMATION: Xaa = G, T, D, E or N
<220> FEATURE:
<221> NAME/KEY: VARIANT
<222> LOCATION: 4
<223> OTHER INFORMATION: Xaa = Q, V, E or G
<220> FEATURE:
<221> NAME/KEY: VARIANT
<222> LOCATION: 6
<223> OTHER INFORMATION: Xaa = L, V, I, M, Q or E
<220> FEATURE:
<221> NAME/KEY: VARIANT
<222> LOCATION: 7
<223> OTHER INFORMATION: Xaa = D or N
<220> FEATURE:
<221> NAME/KEY: VARIANT
<222> LOCATION: 8
<223> OTHER INFORMATION: Xaa = L or I
<220> FEATURE:
<221> NAME/KEY: VARIANT
<222> LOCATION: 9
<223> OTHER INFORMATION: Xaa = S, C, T, V or A
<220> FEATURE:
<221> NAME/KEY: VARIANT
<222> LOCATION: 10
<223> OTHER INFORMATION: Xaa = C, M, L, K, V or T
<220> FEATURE:
<221> NAME/KEY: VARIANT
<222> LOCATION: 11
<223> OTHER INFORMATION: Xaa = K, A or R
<220> FEATURE:
<221> NAME/KEY: VARIANT
<222> LOCATION: 12
<223> OTHER INFORMATION: Xaa = R, T, H, P, K or C
<220> FEATURE:
<221> NAME/KEY: VARIANT
<222> LOCATION: 13
<223> OTHER INFORMATION: Xaa = P, S, G, R or L

<400> SEQUENCE: 163

Xaa Xaa Xaa Xaa Pro Xaa Xaa Xaa Xaa Xaa Xaa Xaa
 1               5                   10

<210> SEQ ID NO 164
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = E, G, P, A or V
<220> FEATURE:
<221> NAME/KEY: VARIANT
<222> LOCATION: 2
<223> OTHER INFORMATION: Xaa = P, Q, G, S, T, V or M
<220> FEATURE:
<221> NAME/KEY: VARIANT
<222> LOCATION: 3
<223> OTHER INFORMATION: Xaa = G, T, D, E or N
<220> FEATURE:
<221> NAME/KEY: VARIANT
<222> LOCATION: 4
<223> OTHER INFORMATION: Xaa = Q, V, E or G

<400> SEQUENCE: 164

Xaa Xaa Xaa Xaa
 1

<210> SEQ ID NO 165
<211> LENGTH: 4
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = C, M, L, K, V or T
<220> FEATURE:
<221> NAME/KEY: VARIANT
<222> LOCATION: 2
<223> OTHER INFORMATION: Xaa = K, A or R
<220> FEATURE:
<221> NAME/KEY: VARIANT
<222> LOCATION: 3
<223> OTHER INFORMATION: Xaa = R, T, H, P, K or C
<220> FEATURE:
<221> NAME/KEY: VARIANT
<222> LOCATION: 4
<223> OTHER INFORMATION: Xaa = P, S, G, R or L

<400> SEQUENCE: 165

Xaa Xaa Xaa Xaa
 1

<210> SEQ ID NO 166
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = C, M, L, K, V or T
<220> FEATURE:
<221> NAME/KEY: VARIANT
<222> LOCATION: 2
<223> OTHER INFORMATION: Xaa = K, A or R
<220> FEATURE:
<221> NAME/KEY: VARIANT
<222> LOCATION: 3
<223> OTHER INFORMATION: Xaa = R, T, H, P, K or C
<220> FEATURE:
<221> NAME/KEY: VARIANT
<222> LOCATION: 4
<223> OTHER INFORMATION: Xaa = P, S, G, R or L
<220> FEATURE:
<221> NAME/KEY: VARIANT
<222> LOCATION: 5
<223> OTHER INFORMATION: Xaa = R, K, P, T, L or S

<400> SEQUENCE: 166

Xaa Xaa Xaa Xaa Xaa
 1               5

<210> SEQ ID NO 167
<211> LENGTH: 20
<212> TYPE: DNA
<213> ORGANISM: Artificial Sequence
<220> FEATURE:
<223> OTHER INFORMATION: Synthetic contruct

<400> SEQUENCE: 167
tctgataggc agcctgcacc                                              20

<210> SEQ ID NO 168
<211> LENGTH: 20
<212> TYPE: DNA
<213> ORGANISM: Artificial Sequence
<220> FEATURE:
<223> OTHER INFORMATION: Synthetic contruct

<400> SEQUENCE: 168
```

```
atcccagctg ctgtggaagg                                              20

<210> SEQ ID NO 169
<211> LENGTH: 19
<212> TYPE: DNA
<213> ORGANISM: Artificial Sequence
<220> FEATURE:
<223> OTHER INFORMATION: Synthetic contruct

<400> SEQUENCE: 169
ggggtaccac cttgtttcc                                               19

<210> SEQ ID NO 170
<211> LENGTH: 19
<212> TYPE: DNA
<213> ORGANISM: Artificial Sequence
<220> FEATURE:
<223> OTHER INFORMATION: Synthetic contruct

<400> SEQUENCE: 170
gaagatctct cctcccgc                                                19
```